US012799486B2

(12) United States Patent
Gentile et al.

(10) Patent No.: US 12,799,486 B2
(45) Date of Patent: Nov. 17, 2026

(54) OLIGONUCLEOTIDES FOR PRNP MODULATION

(71) Applicants: UNIVERSITY OF MASSACHUSETTS, Westborough, MA (US); THE BROAD INSTITUTE, INC., Cambridge, MA (US)

(72) Inventors: Juliana Gentile, Cambridge, MA (US); Sonia Vallabh, Cambridge, MA (US); Eric Minikel, Cambridge, MA (US); Anastasia Khvorova, Westborough, MA (US); Zachary Kennedy, Worcester, MA (US); Ken Yamada, Westborough, MA (US)

(73) Assignees: UNIVERSITY OF MASSACHUSETTS, Westborough, MA (US); THE BROAD INSTITUTE, INC., Cambridge, MA (US)

( * ) Notice: Subject to any disclaimer, the term of this patent is extended or adjusted under 35 U.S.C. 154(b) by 0 days.

(21) Appl. No.: 19/355,121

(22) Filed: Oct. 10, 2025

(65) Prior Publication Data

US 2026/0035699 A1 Feb. 5, 2026

Related U.S. Application Data

(63) Continuation of application No. PCT/US2025/019501, filed on Mar. 12, 2025.
(Continued)

(51) Int. Cl.
*C12N 15/113* (2010.01)
*A61K 9/00* (2006.01)
(Continued)

(52) U.S. Cl.
CPC .......... *C12N 15/113* (2013.01); *A61K 9/0085* (2013.01); *A61K 31/712* (2013.01);
(Continued)

(58) Field of Classification Search
CPC .............. C12N 15/113; C12N 2310/11; C12N 2310/14; A61K 31/713
See application file for complete search history.

(56) References Cited

U.S. PATENT DOCUMENTS 5,684,143 A 11/1997 Grayaznov et al.
5,814,014 A 9/1998 Elsberry et al.
(Continued)

FOREIGN PATENT DOCUMENTS

WO WO 2017/030973 A1 2/2017
WO WO 2017/132669 A1 8/2017
(Continued)

OTHER PUBLICATIONS

Aviñó, Anna, et al. "Branched RNA: A New Architecture for RNA Interference." Journal of Nucleic Acids, vol. 2011, 2011, pp. 1-7, https://doi.org/10.4061/2011/586935. Accessed Feb. 12, 2026. (Year: 2011).*

(Continued)

*Primary Examiner* — Kimberly Chong
*Assistant Examiner* — Africa M Mcleod
(74) *Attorney, Agent, or Firm* — LATHROP GPM LLP; James H. Velema, Esq.

(57) ABSTRACT

This disclosure relates to novel PRNP targeting sequences. Novel PRNP targeting oligonucleotides for the treatment of neurodegenerative diseases are also provided.

5 Claims, 14 Drawing Sheets

Specification includes a Sequence Listing.

Related U.S. Application Data

(60) Provisional application No. 63/564,255, filed on Mar. 12, 2024.

(51) Int. Cl.
*A61K 31/712* (2006.01)
*A61K 31/7125* (2006.01)
*A61K 31/713* (2006.01)
*A61K 47/02* (2006.01)
*A61P 25/28* (2006.01)

(52) U.S. Cl.
CPC ........ *A61K 31/7125* (2013.01); *A61K 31/713* (2013.01); *A61K 47/02* (2013.01); *A61P 25/28* (2018.01); *C12N 2310/11* (2013.01); *C12N 2310/14* (2013.01); *C12N 2310/312* (2013.01); *C12N 2310/315* (2013.01); *C12N 2310/321* (2013.01); *C12N 2310/322* (2013.01); *C12N 2310/3519* (2013.01)

(56) References Cited

U.S. PATENT DOCUMENTS

| | | | |
|---|---|---|---|
| 5,858,988 A | 1/1999 | Wang | |
| 6,093,180 A | 7/2000 | Elsberry et al. | |
| 6,291,438 B1 | 9/2001 | Wang | |
| 7,459,547 B2 | 12/2008 | Zamore et al. | |
| 7,732,593 B2 | 6/2010 | Zamore et al. | |
| 7,750,144 B2 | 7/2010 | Zamore et al. | |
| 7,772,203 B2 | 8/2010 | Zamore et al. | |
| 8,304,530 B2 | 11/2012 | Zamore et al. | |
| 8,309,704 B2 | 11/2012 | Zamore et al. | |
| 8,309,705 B2 | 11/2012 | Zamore et al. | |
| 8,329,892 B2 | 12/2012 | Zamore et al. | |
| 8,431,544 B1 | 4/2013 | Agrawal et al. | |
| 2005/0220766 A1 | 10/2005 | Amalfitano et al. | |
| 2006/0078542 A1 | 4/2006 | Mah et al. | |
| 2007/0259827 A1 | 11/2007 | Aronin et al. | |
| 2008/0269149 A1 | 10/2008 | Bowles et al. | |
| 2010/0186103 A1 | 7/2010 | Gao et al. | |
| 2014/0296486 A1 | 10/2014 | Gao et al. | |
| 2020/0385740 A1 | 12/2020 | Khvorova et al. | |
| 2021/0317460 A1 | 10/2021 | Khvorova et al. | |
| 2022/0025366 A1 | 1/2022 | Freier et al. | |
| 2024/0287526 A1* | 8/2024 | Hassler | C12N 15/1138 |

FOREIGN PATENT DOCUMENTS

| | | | | |
|---|---|---|---|---|
| WO | WO 2018/031933 A2 | 2/2018 | | |
| WO | WO-2021173984 A2 * | 9/2021 | | C12N 15/1138 |
| WO | WO 2022/182864 A1 | 9/2022 | | |
| WO | WO 2023/060092 A1 | 4/2023 | | |

OTHER PUBLICATIONS

Alterman et al., "A divalent siRNA chemical scaffold for potent and sustained modulation of gene expression throughout the central nervous system", Nat Biotechnol., Aug. 2019, 37(8): 884-894.
Alvarez-Erviti, et al., "Delivery of siRNA To The Mouse Brain By Systemic Injection Of Targeted Exosomes", Nature Biotechnology, vol. 29, No. 4, pp. 341-345, Apr. 2011.
Ambros, et al., MicroRNAs and Other Tiny Endogenous RNAs in C. elegans, Current Biology, vol. 13, Issue 10, pp. 807-818, May 13, 2003.
Billy et al., "Specific interference with gene expression induced by long, double-stranded RNA in mouse embryonal teratocarcinoma cell lines", PNAS USA, Dec. 4, 2001, 98(25):14428-14433, Epublished Nov. 27, 2001.
Braasch, et al., "RNA Interference in Mammalian Cells by Chemically-Modified RNA", Biochemistry, vol. 42, No. 26, pp. 7967-7975, Jun. 11, 2003.
Brennecke, et al., Towards A Complete Description Of The microRNA Complement Of Animal Genomes, Genome Biology, vol. 4, No. 9, 3 Pages, Aug. 21, 2003.
Calegari, et al., Tissue-Specific RNA Interference In Postimplantation Mouse Embryos With Endoribonuclease-Prepared Short Interfering RNA, Proceedings of the National Academy of Sciences, vol. 99, No. 22, pp. 14236-14240, Oct. 29, 2002.
Doench, et al., siRNAs Can Function As miRNAs, Genes & Development, vol. 17, pp. 438-442, 2003.
Eckstein, Phosphorothioate Oligodeoxynucleotides: What Is Their Origin and What Is Unique About Them?, Antisense and Nucleic Acid Drug Development, vol. 10, Issue 2, pp. 117-121, Jan. 30, 2009.
Egusquiaguirre, et al., "Nanoparticle Delivery Systems For Cancer Therapy: Advances In Clinical And Preclinical Research", Clinical and Translational Oncology, vol. 14, pp. 83-93, 2012.
El Andaloussi, et al., "Exosome-Mediated Delivery of siRNA In Vitro And In Vivo", Nature Protocols, vol. 7, No. 12, pp. 2112-2126, Nov. 15, 2012.
El Andaloussi, et al., "Exosomes For Targeted siRNA Delivery Across Biological Barriers", Advanced Drug Delivery Reviews, vol. 65, pp. 391-397, 2013.
El Andaloussi, et al., "Extracellular Vesicles: Biology And Emerging Therapeutic Opportunities", Nature Reviews Drug Discovery, vol. 12, pp. 347-357, May 2013.
Elmen, et al., Locked Nucleic Acid (LNA) Mediated Improvements in siRNA Stability And Functionality, Nucleic Acids Research, vol. 33, Issue 1, pp. 439-447, Jan. 14, 2005.
Fattal, et al., Biodegradable Polyalkylcyanoacrylate Nanoparticles For The Delivery Of Oligonucleotides, Journal of Controlled Release, vol. 53, pp. 137-143, May 1998.
Godard, et al., "Antisense Effects of Cholesterol-Oligodeoxynucleotide Conjugates Associated with Poly(alkylcyanoacrylate) Nanoparticles", European Journal of Biochemistry banner, vol. 232, pp. 404-410, 1995.
Grad, et al., Computational and Experimental Identification of C. elegans microRNAs, Molecular Cell, vol. 11, Issue 5, pp. 1253-1263, May 2003.
Griffiths-Jones, San, The microRNA Registry, Nucleic Acids Research, vol. 32, Issue Supplement 1, pp. D109-D111, Jan. 1, 2004.
Hutvagner, et al., A microRNA in a Multiple-Turnover RNAi Enzyme Complex, Science, vol. 297, Issue 5589, pp. 2056-2060, Sep. 20, 2002.
International Search Report and Written Opinion for PCT International Patent Application No. PCT/US2025/19501, mailed Jul. 23, 2025.
Karlin et al., "Applications and statistics for multiple high-scoring segments in molecular sequences", PNAS USA, Jun. 1993, 90(12): 5873-5877.
Karlin et al., "Methods for assessing the statistical significance of molecular sequence features by using general scoring schemes", PNAS USA, Mar. 15, 1990, 87(6): 2264-2268.
Lagos-Quintana, et al., Identification of Novel Genes Coding for Small Expressed RNAs, Science, vol. 294, Issue 5543, pp. 853-858, Oct. 26, 2001.
Lagos-Quintana, et al., Identification of Tissue-Specific MicroRNAs from Mouse, Current Biology, vol. 12, Issue 9, pp. 735-739, Apr. 30, 2002.
Lagos-Quintana, et al., New microRNAs From Mouse And Human, RNA, vol. 9, No. 2, pp. 175-179, 2003.
Lai, et al., Computational Identification of *Drosophila* microRNA Genes, Genome Biology, vol. 4, No. 7, pp. 1-20, Jun. 30, 2003.
Lam, et al., "A New Type of Synthetic Peptide Library For Identifying Ligand-Binding Activity", Nature, vol. 354, pp. 82-84, Nov. 7, 1991.
Lambert, et al., "Nanoparticulate Systems For The Delivery Of Antisense Oligonucleotides", Advanced Drug Delivery Reviews, vol. 47, pp. 99-112, 2001.
Lau, et al., An Abundant Class of Tiny RNAs with Probable Regulatory Roles in Caenorhabditis elegans, Science, vol. 294, Issue 5543, pp. 858-862, Oct. 26, 2001.

(56) References Cited

OTHER PUBLICATIONS

Lee, et al., "Recent Developments In Nanoparticle-Based siRNA Delivery For Cancer Therapy", BioMed Research International, vol. 2013, Article ID 782041, 10 Pages, Jun. 2013.
Lee, et al., An Extensive Class of Small RNAs in Caenorhabditis elegans, Science, vol. 294, Issue 5543, pp. 862-864, Oct. 26, 2001.
Lewis et al., "Efficient delivery of siRNA for inhibition of gene expression in postnatal mice", Nature Genetics, Brief Communications, Jul. 29, 2002, 32: 107-108.
Lim, et al., The microRNAs of Caenorhabditis elegans, Genes & Development, vol. 17, No. 8, pp. 991-1008, 2003.
Lim, et al., Vertebrate MicroRNA Genes, Science, vol. 299, Issue 5612, p. 1540, Mar. 7, 2003.
McCaffrey, et al., Gene Expression: RNA Interference in Adult Mice, Nature, vol. 418, No. 6893, pp. 38-39, Jul. 4, 2002.
Mortberg et al. "Regional variability and genotypic and pharmacodynamic effects on PrP concentration in the CNS", JCI Insight., Mar. 22, 2022, 7(6): e156532.
Mourelatos, et al., miRNPs: A Novel Class Of Ribonucleoproteins Containing Numerous microRNAs, Genes & Development, vol. 16, No. 6, pp. 720-728, 2002.
Nielsen, et al., Sequence-Selective Recognition of DNA by Strand Displacement With A Thymine-Substituted Polyamide, Science, vol. 254, Issue 5037, pp. 1497-1500, Dec. 6, 1991.
Pasquinelli, et al., Conservation of The Sequence And Temporal Expression of let-7 Heterochronic Regulatory RNA, Nature, vol. 408, No. 6808, pp. 86-89., Nov. 2, 2000.
Petersen, et al., LNA: A Versatile Tool for Therapeutics and Genomics, Trends in Biotechnology, vol. 21, Issue 2, pp. 74-81, Feb. 2003.
Putnam, David A., Antisense Strategies and Therapeutic Applications, American Journal of Health System Pharmacy, vol. 53, No. 2, pp. 151-160, Jan. 15, 1996.
Reinhart, et al., Small RNAs Correspond to Centromere Heterochromatic Repeats, Science, vol. 297, No. 5588, 1 Page, Sep. 13, 2002.
Rusckowski, et al., Biodistribution and Metabolism of a Mixed Backbone Oligonucleotide (GEM 231) Following Single and Multiple Dose Administration in Mice, Antisense and Nucleic Acid Drug Development, vol. 10, Issue 5, pp. 333-345, Jan. 30, 2009.
Schwab, et al., An Approach For New Anticancer Drugs:Oncogene-Targeted Antisense DNA, Annals of Oncology, vol. 5, Issue 4, pp. 55-58, 1994.
Stein, et al., Inhibition of Vesivirus Infections in Mammalian Tissue Culture with Antisense Morpholino Oligomers, Antisense and Nucleic Acid Drug Development, vol. 11, Issue 5, pp. 317-325, Oct. 2001.
Vorobjev, et al., Nuclease Resistance and RNase H Sensitivity of Oligonucleotides Bridged by Oligomethylenediol and Oligoethylene Glycol Linkers, Antisense and Nucleic Acid Drug Development, vol. 11, No. 2, pp. 77-85, Apr. 2011.
Wang, et al., Nanoparticle-Based Delivery System for Application of siRNA In Vivo, Current Drug Metabolism, vol. 11, No. 2, pp. 182-196, 2010.
Wenborn et al., "A novel and rapid method for obtaining high titre intact prion strains from mammalian brain", Scientific Reports, May 7, 2015, 5: 10062.
Xia, et al., siRNA-Mediated Gene Silencing in Vitroand In Vivo, Nature Biotechnology, vol. 20, No. 10, pp. 1006-1010, Sep. 16, 2002.
Yekta, et al., MicroRNA-Directed Cleavage of HOXB8 mRNA, Science, Apr. 23, 2004, 304(5670): 594-596.
Yuan, et al., Recent Advances of siRNA Delivery By Nanoparticles, Expert Opinion on Drug Delivery vol. 8, Issue 4, pp. 521-536, 2011.
Zeng, et al., Both Natural and Designed Micro RNAs Can Inhibit the Expression of Cognate mRNAs When Expressed in Human Cells, Molecular Cell, vol. 9, pp. 1327-1333, Jun. 2002.
Zeng, et al., Sequence Requirements for Micro RNA Processing and Function in Human Cells, RNA, vol. 9, pp. 112-123, 2003.

* cited by examiner

```
                                SEQUENCE LISTING


Sequence total quantity: 13
SEQ ID NO: 1           moltype = RNA  length = 21
FEATURE                Location/Qualifiers
source                 1..21
                       mol_type = other RNA
                       organism = synthetic construct
SEQUENCE: 1
tgaatactca caaagtgcat t                                            21

SEQ ID NO: 2           moltype = RNA  length = 16
FEATURE                Location/Qualifiers
source                 1..16
                       mol_type = other RNA
                       organism = synthetic construct
SEQUENCE: 2
actttgtgag tattca                                                  16

SEQ ID NO: 3           moltype = RNA  length = 21
FEATURE                Location/Qualifiers
source                 1..21
                       mol_type = other RNA
                       organism = synthetic construct
modified_base          order(1,3,7,9,11,13,15,17..20)
                       mod_base = OTHER
                       note = 2-Prime-O-methyl ribonucleotides
modified_base          order(2,4..6,8,10,12,14,16,21)
                       mod_base = OTHER
                       note = 2-Prime-fluoro ribonucleotides
modified_base          order(1..3,19..21)
                       mod_base = OTHER
                       note = Phosphorothioate internucleotide linkages
modified_base          19..21
                       mod_base = OTHER
                       note = Internucleotide linkages
SEQUENCE: 3
tgaatactca caaagtgcat t                                            21

SEQ ID NO: 4           moltype = RNA  length = 16
FEATURE                Location/Qualifiers
source                 1..16
                       mol_type = other RNA
                       organism = synthetic construct
modified_base          order(1..3,5,7,9,11..13,15..16)
                       mod_base = OTHER
                       note = 2-Prime-O-methyl ribonucleotides
modified_base          order(4,6,8,10,14)
                       mod_base = OTHER
                       note = 2-Prime-fluoro ribonucleotides
modified_base          order(1..3,14..16)
                       mod_base = OTHER
                       note = Phosphorothioate internucleotide linkages
SEQUENCE: 4
actttgtgag tattca                                                  16

SEQ ID NO: 5           moltype = RNA  length = 21
FEATURE                Location/Qualifiers
source                 1..21
                       mol_type = other RNA
                       organism = synthetic construct
modified_base          1
                       mod_base = OTHER
                       note = 5-Prime-vinyl phosphonate
```

-continued

```
modified_base          order(1,3,7,9,11,13,15,17..20)
                       mod_base = OTHER
                       note = 2-Prime-O-methyl ribonucleotides
modified_base          order(2,4..6,8,10,12,14,16,21)
                       mod_base = OTHER
                       note = 2-Prime-fluoro ribonucleotides
modified_base          order(1..3,19..21)
                       mod_base = OTHER
                       note = Phosphorothioate internucleotide linkages
modified_base          19..21
                       mod_base = OTHER
                       note = Internucleotide linkages
SEQUENCE: 5
tgaatactca caaagtgcat t                                              21

SEQ ID NO: 6           moltype = RNA  length = 16
FEATURE                Location/Qualifiers
source                 1..16
                       mol_type = other RNA
                       organism = synthetic construct
modified_base          order(1..3,5,7,9,11..13,15..16)
                       mod_base = OTHER
                       note = 2-Prime-O-methyl ribonucleotides
modified_base          order(4,6,8,10,14)
                       mod_base = OTHER
                       note = 2-Prime-fluoro ribonucleotides
modified_base          order(1..3,14..16)
                       mod_base = OTHER
                       note = Phosphorothioate internucleotide linkages
SEQUENCE: 6
actttgtgag tattca                                                    16

SEQ ID NO: 7           moltype = RNA  length = 21
FEATURE                Location/Qualifiers
source                 1..21
                       mol_type = other RNA
                       organism = synthetic construct
modified_base          order(1,3,7,9,11,13,15,17..20)
                       mod_base = OTHER
                       note = 2-Prime-O-methyl ribonucleotides
modified_base          order(2,4..6,8,10,12,14,16,21)
                       mod_base = OTHER
                       note = 2-Prime-fluoro ribonucleotides
modified_base          order(1..3,15..21)
                       mod_base = OTHER
                       note = Phosphorothioate internucleotide linkages
modified_base          19..21
                       mod_base = OTHER
                       note = Internucleotide linkages
SEQUENCE: 7
tgaatactca caaagtgcat t                                              21

SEQ ID NO: 8           moltype = RNA  length = 21
FEATURE                Location/Qualifiers
source                 1..21
                       mol_type = other RNA
                       organism = synthetic construct
modified_base          1
                       mod_base = OTHER
                       note = 5-Prime-vinyl phosphonate
modified_base          order(1,3,7,9,11,13,15,17..20)
                       mod_base = OTHER
                       note = 2-Prime-O-methyl ribonucleotides
modified_base          order(2,4..6,8,10,12,14,16,21)
                       mod_base = OTHER
                       note = 2-Prime-fluoro ribonucleotides
modified_base          order(1..3,15..21)
                       mod_base = OTHER
                       note = Phosphorothioate internucleotide linkages
modified_base          19..21
                       mod_base = OTHER
                       note = Internucleotide linkages
SEQUENCE: 8
tgaatactca caaagtgcat t                                              21

SEQ ID NO: 9           moltype = RNA  length = 21
FEATURE                Location/Qualifiers
```

```
source                 1..21
                       mol_type = other RNA
                       organism = synthetic construct
modified_base          order(1,3,7,9,11,13,15,17..20)
                       mod_base = OTHER
                       note = 2-Prime-O-methyl ribonucleotides
modified_base          order(2,4..6,8,10,12,14,16,21)
                       mod_base = OTHER
                       note = 2-Prime-fluoro ribonucleotides
modified_base          order(1..3,16..21)
                       mod_base = OTHER
                       note = Phosphorothioate internucleotide linkages
modified_base          19..21
                       mod_base = OTHER
                       note = Internucleotide linkages
SEQUENCE: 9
tgaatactca caaagtgcat t                                            21

SEQ ID NO: 10          moltype = RNA  length = 21
FEATURE                Location/Qualifiers
source                 1..21
                       mol_type = other RNA
                       organism = synthetic construct
modified_base          1
                       mod_base = OTHER
                       note = 5-Prime-vinyl phosphonate
modified_base          order(1,3,7,9,11,13,15,17..20)
                       mod_base = OTHER
                       note = 2-Prime-O-methyl ribonucleotides
modified_base          order(2,4..6,8,10,12,14,16,21)
                       mod_base = OTHER
                       note = 2-Prime-fluoro ribonucleotides
modified_base          order(1..3,16..21)
                       mod_base = OTHER
                       note = Phosphorothioate internucleotide linkages
modified_base          19..21
                       mod_base = OTHER
                       note = Internucleotide linkages
SEQUENCE: 10
tgaatactca caaagtgcat t                                            21

SEQ ID NO: 11          moltype = RNA  length = 21
FEATURE                Location/Qualifiers
source                 1..21
                       mol_type = other RNA
                       organism = synthetic construct
modified_base          order(1,3,7,9,11,13,15,17..20)
                       mod_base = OTHER
                       note = 2-Prime-O-methyl ribonucleotides
modified_base          order(2,4..6,8,10,12,14,16,21)
                       mod_base = OTHER
                       note = 2-Prime-fluoro ribonucleotides
modified_base          order(1..3,17..21)
                       mod_base = OTHER
                       note = Phosphorothioate internucleotide linkages
modified_base          19..21
                       mod_base = OTHER
                       note = Internucleotide linkages
SEQUENCE: 11
tgaatactca caaagtgcat t                                            21

SEQ ID NO: 12          moltype = RNA  length = 21
FEATURE                Location/Qualifiers
source                 1..21
                       mol_type = other RNA
                       organism = synthetic construct
modified_base          1
                       mod_base = OTHER
                       note = 5-Prime-vinyl phosphonate
modified_base          order(1,3,7,9,11,13,15,17..20)
                       mod_base = OTHER
                       note = 2-Prime-O-methyl ribonucleotides
modified_base          order(2,4..6,8,10,12,14,16,21)
                       mod_base = OTHER
                       note = 2-Prime-fluoro ribonucleotides
modified_base          order(1..3,17..21)
                       mod_base = OTHER
                       note = Phosphorothioate internucleotide linkages
```

-continued

```
modified_base          19..21
                       mod_base = OTHER
                       note = Internucleotide linkages
SEQUENCE: 12
tgaatactca caaagtgcat t                                      21

SEQ ID NO: 13          moltype = RNA  length = 37
FEATURE                Location/Qualifiers
source                 1..37
                       mol_type = other RNA
                       organism = synthetic construct
modified_base          order(1..3,5,7,9,11..13,15..17,19,23,25,27,29,31,33..35)
                       mod_base = OTHER
                       note = 2-Prime-O-methyl ribonucleotides
modified_base          order(4,6,8,10,14,18,20..22,24,26,28,30,32)
                       mod_base = OTHER
                       note = 2-Prime-fluoro ribonucleotides
modified_base          36
                       mod_base = OTHER
                       note = 2-Prime-O-methyl extended nucleic acid
modified_base          37
                       mod_base = OTHER
                       note = 2-Prime-fluoro extended nucleic acid
modified_base          order(1..3,14..16,17..19,35..37)
                       mod_base = OTHER
                       note = Phosphorothioate linkages
modified_base          order(3..14,19..35)
                       mod_base = OTHER
                       note = Phosphodiester linkages
modified_base          17
                       mod_base = OTHER
                       note = 5-Prime-vinyl phosphonate
SEQUENCE: 13
actttgtgag tattcatgaa tactcacaaa gtgcatt                     37
```

OLIGONUCLEOTIDES FOR PRNP MODULATION

CROSS-REFERENCE TO RELATED APPLICATIONS

This application is a continuation of International Patent Application No. PCT/US2025/019501, filed Mar. 12, 2025, which claims the benefit of U.S. Provisional Patent Application Ser. No. 63/564,255, filed Mar. 12, 2024. The entire contents of the above-referenced patent applications are incorporated by reference in their entirety herein.

GOVERNMENT SUPPORT CLAUSE

This invention was made with government support under NS119717 and NS132994 awarded by National Institutes of Health. The government has certain rights in the invention.

SEQUENCE LISTING

The instant application contains a Sequence Listing which has been submitted electronically in XML format and is hereby incorporated by reference in its entirety. Said XML file, created on Sep. 19, 2025, is named 769982_UM9-311PCCON_ST26.xml and is 40,621 bytes in size.

FIELD OF THE INVENTION

This disclosure relates to novel PRNP targeting sequences, novel branched oligonucleotides, and novel methods for treating and preventing PRNP-related neurodegeneration.

BACKGROUND

PRNP (prion protein, PrP, CD230) encodes a protein known for its role in the pathogenesis of several neurodegenerative disorders known as prion diseases, which includes Creutzfeldt-Jakob disease (CJD) and Fatal familial insomnia (FFI). In pathological conditions, prion protein misfolds and recruits other prion protein molecules to misfold. The misfolded proteins may spread from cell to cell and in some cases, to a new host. Accordingly, there existing a need to efficiently and potently silence PRNP mRNA expression, which the present application addresses.

SUMMARY

In one aspect, the disclosure provides a double stranded RNA (dsRNA) comprising an antisense strand of UGAAUACUCACAAAGUGCAUU (SEQ ID NO: 1) and a sense strand of ACUUUGUGAGUAUUCA (SEQ ID NO: 2).

In certain embodiments, the antisense strand comprises substantially complementary to a PRNP nucleic acid sequence.

In certain embodiments, the dsRNA comprises at least one modified nucleotide.

In certain embodiments, the modified nucleotide comprises a 2'-O-methyl modified nucleotide, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, or a mixture thereof.

In certain embodiments, the dsRNA comprises at least one modified internucleotide linkage.

In certain embodiments, the modified internucleotide linkage comprises a phosphorothioate internucleotide linkage. In certain embodiments, the dsRNA comprises 4-16 phosphorothioate internucleotide linkages. In certain embodiments, the dsRNA comprises 8-13 phosphorothioate internucleotide linkages.

In certain embodiments, the nucleotides at positions 1-2 to 1-7 from 3' end of the antisense strand are connected to each other via phosphorothioate internucleotide linkages. In certain embodiments, the nucleotides at positions 1-2 from 3' end of the antisense strand are connected to each other via phosphorothioate internucleotide linkages. In certain embodiments, the nucleotides at positions 1-3 from 3' end of the antisense strand are connected to each other via phosphorothioate internucleotide linkages. In certain embodiments, the nucleotides at positions 1-4 from 3' end of the antisense strand are connected to each other via phosphorothioate internucleotide linkages. In certain embodiments, the nucleotides at positions 1-5 from 3' end of the antisense strand are connected to each other via phosphorothioate internucleotide linkages. In certain embodiments, the nucleotides at positions 1-6 from 3' end of the antisense strand are connected to each other via phosphorothioate internucleotide linkages. In certain embodiments, the nucleotides at positions 1-7 from 3' end of the antisense strand are connected to each other via phosphorothioate internucleotide linkages.

In certain embodiments, the nucleotides at positions 1-2 from the 5' end of the antisense strand are connected to each other via phosphorothioate internucleotide linkages.

In certain embodiments, the antisense strand comprises 4 phosphorothioate internucleotide linkages. In certain embodiments, the antisense strand comprises 5 phosphorothioate internucleotide linkages. In certain embodiments, the antisense strand comprises 6 phosphorothioate internucleotide linkages. In certain embodiments, the antisense strand comprises 7 phosphorothioate internucleotide linkages. In certain embodiments, the antisense strand comprises 8 phosphorothioate internucleotide linkages.

In certain embodiments, the nucleotides at positions 1-2 from the 5' end of the sense strand are connected to each other via phosphorothioate internucleotide linkages.

In certain embodiments, the nucleotides at positions 1-2 from 3' end of the sense strand are connected to each other via phosphorothioate internucleotide linkages.

In certain embodiments, the dsRNA comprises at least one modified internucleotide linkage of Formula I:

(I)

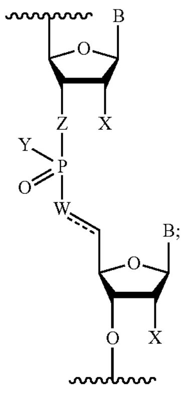

wherein:

- B is a base pairing moiety;
- W is selected from the group consisting of O, $OCH_2$, OCH, $CH_2$, and CH;
- X is selected from the group consisting of halo, hydroxy, and $C_{1-6}$ alkoxy;
- Y is selected from the group consisting of $O^-$, OH, OR, $NH^-$, $NH_2$, $S^-$, and SH;
- Z is selected from the group consisting of O and $CH_2$;
- R is a protecting group; and
- ⎓ is an optional double bond.

In certain embodiments, W is $OCH_2$ and Z is O.

In certain embodiments, the modified internucleotide linkage of Formula (I) is a modified internucleotide linkage of Formula VI:

(VI)

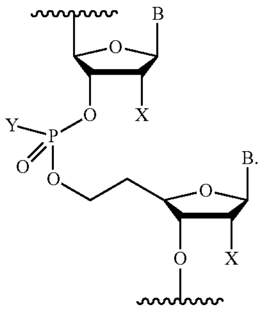

In certain embodiments, the antisense strand comprises at least one modified internucleotide linkage of Formula I or Formula VI. In certain embodiments, the antisense strand comprises the modified internucleotide linkage of Formula I or Formula VI at the antisense strand 3' end. In certain embodiments, the antisense strand comprises 2 to 5 modified internucleotide linkages of Formula I or Formula VI at the antisense strand 3' end.

In certain embodiments, the dsRNA comprises at least 80% chemically modified nucleotides.

In certain embodiments, the dsRNA is fully chemically modified.

In certain embodiments, the antisense strand comprises at least 50% 2'-O-methyl nucleotide modifications.

In certain embodiments, the antisense strand comprises at least 10 2'-O-methyl nucleotide modifications.

In certain embodiments, the sense strand comprises at least 65% 2'-O-methyl nucleotide modifications.

In certain embodiments, the sense strand comprises at least 10 2'-O-methyl nucleotide modifications.

In certain embodiments, the antisense strand comprises a 5' phosphate, a 5'-alkyl phosphonate, a 5' alkylene phosphonate, or a 5' alkenyl phosphonate.

In certain embodiments, the antisense strand comprises a 5' vinyl phosphonate.

In certain embodiments, the dsRNA comprises: an antisense strand of (mU)#(fG)#(mA)(fA)(fU)(fA)(mC)(fU)(mC)(fA)(mC)(fA)(mA)(fA)(mG)(fU)(mG)(mC)(mA)#ex(mU)#ex(fU) (SEQ ID NO: 3); and a sense strand of (mA)#(mC)#(mU)(fU)(mU)(fG)(mU)(fG)(mA)(fG)(mU)(mA)(mU)(fU)#(mC)#(mA) (SEQ ID NO: 4), wherein "m" corresponds to a 2'-O-methyl modification, "f" corresponds to a. 2'-fluoro modification, "#" corresponds to a phosphorothioate internucleotide linkage, and "ex" corresponds to a modified internucleotide linkage of Formula I.

In certain embodiments, the dsRNA comprises: an antisense strand of VP(mU)#(fG)#(mA)(fA)(fU)(fA)(mC)(fU)(mC)(fA)(mC)(fA)(mA)(fA)(mG)(fU)(mG)(mC)(mA)#ex(mU)#ex(fU) (SEQ ID NO: 5); and a sense strand of (mA)#(mC)#(mU)(fU)(mU)(fG)(mU)(fG)(mA)(fG)(mU)(mA)(mU)(fU)#(mC)#(mA) (SEQ ID NO: 6), wherein "m" corresponds to a 2'-O-methyl modification, "f" corresponds to a. 2'-fluoro modification, "#" corresponds to a phosphorothioate internucleotide linkage, "ex" corresponds to a modified internucleotide linkage of Formula I, and "VP" corresponds to a 5' vinyl phosphonate.

In certain embodiments, the dsRNA comprises: an antisense strand of (mU)#(fG)#(mA)(fA)(fU)(fA)(mC)(fU)(mC)(fA)(mC)(fA)(mA)(fA)(mG)#(fU)#(mG)#(mC)#(mA)#ex(mU)#ex(fU) (SEQ ID NO: a sense strand 7); and of (mA)#(mC)#(mU)(fU)(mU)(fG)(mU)(fG)(mA)(fG)(mU)(mA)(mU)(fU)#(mC)#(mA) (SEQ ID NO: 4), wherein "m" corresponds to a 2'-O-methyl modification, "f" corresponds to a. 2'-fluoro modification, "#" corresponds to a phosphorothioate internucleotide linkage, and "ex" corresponds to a modified internucleotide linkage of Formula I.

In certain embodiments, the dsRNA comprises: an antisense strand of VP(mU)#(fG)#(mA)(fA)(fU)(fA)(mC)(fU)(mC)(fA)(mC)(fA)(mA)(fA)(mG)#(fU)#(mG)#(mC)#(mA)#ex(mU)#ex(fU) (SEQ ID NO: 8); and a sense strand of (mA)#(mC)#(mU)(fU)(mU)(fG)(mU)(fG)(mA)(fG)(mU)(mA)(mU)(fU)#(mC)#(mA) (SEQ ID NO: 6), wherein "m" corresponds to a 2'-O-methyl modification, "f" corresponds to a. 2'-fluoro modification, "#" corresponds to a phosphorothioate internucleotide linkage, "ex" corresponds to a modified internucleotide linkage of Formula I, and "VP" corresponds to a 5' vinyl phosphonate.

In certain embodiments, the dsRNA comprises: an antisense strand of (mU)#(fG)#(mA)(fA)(fU)(fA)(mC)(fU)(mC)(fA)(mC)(fA)(mA)(fA)(mG)(fU)#(mG)#(mC)#(mA)#ex(mU)#ex(fU) (SEQ ID NO: 9); and a sense strand of (mA)#(mC)#(mU)(fU)(mU)(fG)(mU)(fG)(mA)(fG)(mU)(mA)(mU)(fU)#(mC)#(mA) (SEQ ID NO: 4), wherein "m" corresponds to a 2'-O-methyl modification, "f" corresponds to a. 2'-fluoro modification, "#" corresponds to a phosphorothioate internucleotide linkage, and "ex" corresponds to a modified internucleotide linkage of Formula I.

In certain embodiments, the dsRNA comprises: an antisense strand of VP(mU)#(fG)#(mA)(fA)(fU)(fA)(mC)(fU)(mC)(fA)(mC)(fA)(mA)(fA)(mG)(fU)#(mG)#(mC)#(mA)#ex(mU)#ex(fU) (SEQ ID NO: 10); and a sense strand of (mA)#(mC)#(mU)(fU)(mU)(fG)(mU)(fG)(mA)(fG)(mU)(mA)(mU)(fU)#(mC)#(mA) (SEQ ID NO: 6), wherein "m" corresponds to a 2'-O-methyl modification, "f" corresponds to a. 2'-fluoro modification, "#" corresponds to a phosphorothioate internucleotide linkage, "ex" corresponds to a modified internucleotide linkage of Formula I, and "VP" corresponds to a 5' vinyl phosphonate.

In certain embodiments, the dsRNA comprises: an antisense strand of (mU)#(fG)#(mA)(fA)(fU)(fA)(mC)(fU)(mC)(fA)(mC)(fA)(mA)(fA)(mG)(fU)(mG)#(mC)#(mA)#ex(mU)#ex(fU) (SEQ ID NO: 11); and a sense strand of (mA)#(mC)#(mU)(fU)(mU)(fG)(mU)(fG)(mA)(fG)(mU)(mA)(mU)(fU)#(mC)#(mA) (SEQ ID NO: 4), wherein "m" corresponds to a 2'-O-methyl modification, "f" corresponds to a. 2'-fluoro modification, "#" corresponds to a phosphorothioate internucleotide linkage, and "ex" corresponds to a modified internucleotide linkage of Formula I.

In certain embodiments, the dsRNA comprises: an antisense strand of VP(mU)#(fG)#(mA)(fA)(fU)(fA)(mC)(fU)(mC)(fA)(mC)(fA)(mA)(fA)(mG)(fU)(mG)#(mC)#(mA)#ex(mU)#ex(fU) (SEQ ID NO: 12); and a sense strand of (mA)#(mC)#(mU)(fU)(mU)(fG)(mU)(fG)(mA)(fG)(mU)(mA)(mU)(fU)#(mC)#(mA) (SEQ ID NO: 6), wherein "m" corresponds to a 2'-O-methyl modification, "f" corresponds to a. 2'-fluoro modification, "#" corresponds to a phosphorothioate internucleotide linkage, "ex" corresponds to a modified internucleotide linkage of Formula I, and "VP" corresponds to a 5' vinyl phosphonate.

In one aspect, the disclosure provides a pharmaceutical composition for inhibiting the expression of prion protein (PRNP) gene in an organism, comprising the dsRNA described herein and a pharmaceutically acceptable carrier.

In certain embodiments, the dsRNA inhibits the expression of said PRNP gene by at least 20%. In certain embodiments, the dsRNA inhibits the expression of said PRNP gene by at least 30%. In certain embodiments, the dsRNA inhibits the expression of said PRNP gene by at least 40%. In certain embodiments, the dsRNA inhibits the expression of said PRNP gene by at least 50%.

expression of said PRNP gene by at least 30%. In certain embodiments, the dsRNA inhibits the expression of said PRNP gene by at least 40%. In certain embodiments, the dsRNA inhibits the expression of said PRNP gene by at least 50%.

In one aspect, the disclosure provides a branched RNA compound comprising two or more dsRNA described herein, wherein the two or more dsRNA are connected to one another by one or more moieties independently selected from a linker, a spacer and a branching point.

In certain embodiments, the linker comprises an ethylene glycol chain, an alkyl chain, a peptide, an RNA, a DNA, a phosphate, a phosphonate, a phosphoramidate, an ester, an amide, a triazole, or combinations thereof.

In certain embodiments, the linker comprises tetra ethylene glycol.

In certain embodiments, the linker is of structure L1:

(L1)

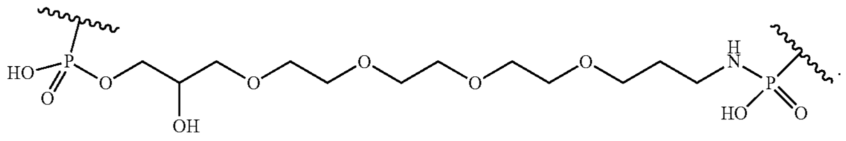

In certain embodiments, the linker is of structure L2:

(L2)

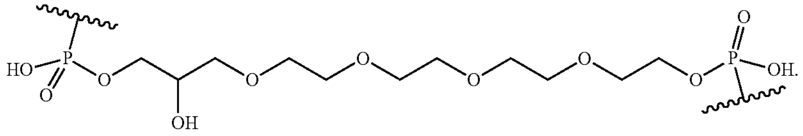

In one aspect, the disclosure provides a method for inhibiting expression of PRNP gene in a cell, the method comprising: (a) introducing into the cell the dsRNA described herein; and (b) maintaining the cell produced in step (a) for a time sufficient to obtain degradation of the mRNA transcript of the PRNP gene, thereby inhibiting expression of the PRNP gene in the cell.

In one aspect, the disclosure provides a method of treating or managing a neurodegenerative disease comprising administering to a patient in need of such treatment or management a therapeutically effective amount of the dsRNA described herein. In certain embodiments, the neurodegenerative disease is a prion disease. In certain embodiments, the prion disease is Creutzfeldt-Jakob disease (CJD). In certain embodiments, the prion disease is Fatal familial insomnia (FFI).

In certain embodiments, the dsRNA is administered to the brain of the patient.

In certain embodiments, the dsRNA is administered by intrathecal (IT) injection, intracerebroventricular (ICV) injection, intrastriatal (IS) injection, intravenous (IV) injection, subcutaneous (SQ) injection or a combination thereof.

In certain embodiments, administering the dsRNA causes a decrease in PRNP gene mRNA in one or more of the hippocampus, striatum, cortex, cerebellum, thalamus, hypothalamus, and spinal cord. In certain embodiments, the dsRNA inhibits the expression of said PRNP gene by at least 20%. In certain embodiments, the dsRNA inhibits the In certain embodiments, the linker is attached to the 3' end of a first sense strand and 3' end of a second sense strand.

In one aspect, the disclosure provides a pharmaceutical composition for inhibiting the expression of prion protein (PRNP) gene in an organism, comprising the branched RNA compound described herein and a pharmaceutically acceptable carrier.

In certain embodiments, the branched RNA compound inhibits the expression of said PRNP gene by at least 20%. In certain embodiments, the branched RNA compound inhibits the expression of said PRNP gene by at least 30%. In certain embodiments, the branched RNA compound inhibits the expression of said PRNP gene by at least 40%. In certain embodiments, the branched RNA compound inhibits the expression of said PRNP gene by at least 50%.

In one aspect, the disclosure provides a method for inhibiting expression of PRNP gene in a cell, the method comprising: (a) introducing into the cell the branched RNA compound described herein; and (b) maintaining the cell produced in step (a) for a time sufficient to obtain degradation of the mRNA transcript of the PRNP gene, thereby inhibiting expression of the PRNP gene in the cell.

In one aspect, the disclosure provides a method of treating or managing a neurodegenerative disease comprising administering to a patient in need of such treatment or management a therapeutically effective amount of the branched RNA compound described herein. In certain embodiments, the neurodegenerative disease is a prion disease. In certain embodiments, the prion disease is Creutzfeldt-Jakob disease (CJD). In certain embodiments, the prion disease is Fatal familial insomnia (FFI).

In certain embodiments, the branched RNA compound is administered to the brain of the patient.

In certain embodiments, the branched RNA compound is administered by intrathecal (IT) injection, intracerebroventricular (ICV) injection, intrastriatal (IS) injection, intravenous (IV) injection, subcutaneous (SQ) injection or a combination thereof.

In certain embodiments, administering the branched RNA compound causes a decrease in PRNP gene mRNA in one or more of the hippocampus, striatum, cortex, cerebellum, thalamus, hypothalamus, and spinal cord. In certain embodiments, the branched RNA compound inhibits the expression of said PRNP gene by at least 20%. In certain embodiments, the branched RNA compound inhibits the expression of said PRNP gene by at least 30%. In certain embodiments, the branched RNA compound inhibits the expression of said PRNP gene by at least 40%. In certain embodiments, the branched RNA compound inhibits the expression of said PRNP gene by at least 50%.

In one aspect, the disclosure provides a pharmaceutical formulation comprising the branched RNA compound described herein and a divalent cation, wherein the branched RNA compound and the divalent cation are present in the formulation at a 25:1 molar ratio of divalent cation to branched RNA compound.

In certain embodiments, the divalent cation is $Mg^{2+}$.

In certain embodiments, the branched RNA compound is present at a concentration of about 0.1 mM to about 1.0 mM.

In certain embodiments, the divalent cation is present at a concentration of about 5.0 mM to about 15.0 mM.

In certain embodiments, the branched RNA compound is present at a concentration of about 0.4 mM and the divalent cation is present at a concentration of about 10 mM.

In one aspect, the disclosure provides a pharmaceutical formulation comprising: i) the branched RNA compound at a concentration of about 1 mg/mL to about 50 mg/mL; ii) potassium phosphate at a concentration of about 0.05 mg/mL to about 0.5 mg/mL; iii) sodium chloride at a concentration of about 5 mg/mL to about 15 mg/mL; iv) sodium phosphate at a concentration of about 0.1 mg/mL to about 2.0 mg/mL; and v) magnesium chloride at a concentration of about 1.0 mg/mL to about 5.0 mg/mL, wherein the branched RNA compound comprises two or more dsRNA comprising an antisense strand of UGAAUACUCACAAAGUGCAUU (SEQ ID NO: 1) and a sense strand of ACUUUGUGAGUAUUCA (SEQ ID NO: 2), wherein the two or more dsRNA are connected to one another by one or more moieties independentlv selected from a linker, a spacer and a branching point.

In certain embodiments, the potassium phosphate is potassium dihydrogen phosphate, the sodium phosphate is sodium phosphate dibasic heptahydrate, and the magnesium chloride is magnesium chloride hexahydrate.

In certain embodiments, the pharmaceutical formulation comprises: i) the branched RNA compound at a concentration of about 10 mg/mL; ii) potassium phosphate at a concentration of about 0.14 mg/mL; iii) sodium chloride at a concentration of about 9 mg/ml; iv) sodium phosphate at a concentration of about 0.8 mg/mL; and v) magnesium chloride at a concentration of about 2.1 mg/mL.

In certain embodiments, the pharmaceutical formulation comprises: i) the branched RNA compound at a concentration of 10 mg/mL; ii) potassium phosphate at a concentration of 0.144 mg/mL; iii) sodium chloride at a concentration of 9.058 mg/mL; iv) sodium phosphate at a concentration of 0.796 mg/mL; and v) magnesium chloride at a concentration of 2.114 mg/mL.

BRIEF DESCRIPTION OF THE DRAWINGS

The foregoing and other features and advantages of the present disclosure will be more fully understood from the following detailed description of illustrative embodiments taken in conjunction with the accompanying drawings.

FIG. 1A depicts an in vitro screen for potent siRNA sequences against mouse Prnp. Sequences were screened in triplicate in N2a cells with Prnp mRNA quantified by a branched DNA (bDNA) assay, normalized to the mean of untreated cells. FIG. 1B depicts an in vivo test of 1682-exNA at 10 nmol (total dose, bilateral ICV) in C57BL/6N mice, whole brain hemisphere PrP by ELISA, 30 days post-dose. FIG. 1C depicts all-cause survival of Rocky Mountain Laboratory (RML) prion-inoculated animals treated with 1682-exNA every 120 days beginning at 75 dpi, triangles indicate doses. N=8 per group. FIG. 1D depicts weight change trajectories versus individual baseline in animals from FIG. 1C, lines indicate means and shaded areas indicate 95% CIs. FIG. 1E depicts all-cause survival of RML prion-inoculated animals treated with a single dose of 1682-exNA at 126 dpi, triangle indicates dose. N=8-11 per group. FIG. 1F depicts weight change trajectories versus individual baseline in animals from FIG. 1E, lines indicate means and shaded areas indicate 95% CIs.

FIG. 2A depicts a screen of 85 human PRNP-targeting siRNAs in human U251-MG glioblastoma cells at 2 μM and 0.5 μM. FIG. 2B depicts dose response curves of siRNAs 1491, 2226, 2522, and 2705. FIG. 2C depicts dose response curves of siRNAs 2439, 2440, 2520, 2710, 2766, and 2768. FIG. 2D depicts all human compounds screened, each in groups of 3-7 Tg26372 humanized mice, whole brain hemisphere PrP quantified by ELISA and normalized to within-cohort, within-plate saline controls. NTC=non-targeting control. hiPS/P3V1=high phosphorothioate backbones, exNA=low phosphorothioate+exNA backbone. Numbers after compound indicate total nmol per animal of divalent compound.

FIG. 3A depicts Prp protein levels from mouse whole brain hemispheres. FIG. 3B depicts Prnp mRNA levels from the prefrontal cortex and hippocampus. FIG. 3C depicts Prnp mRNA levels from the striatum and visual cortex. FIG. 3D depicts Prnp mRNA levels from the thalamus and cerebellum.

FIG. 4A depicts Prp protein levels with 2439-exNA (also referred to as 2439-loPS-exNA and schematically depicted in FIG. 5) and 2439-hiPS-exNA, each administered at 5 nmol. FIG. 4B depicts Prp protein levels with 2439-exNA (also referred to as 2439-loPS-exNA and schematically depicted in FIG. 5) and 2439-hiPS-exNA, each administered at 10 nmol.

DETAILED DESCRIPTION

Figure 1A:
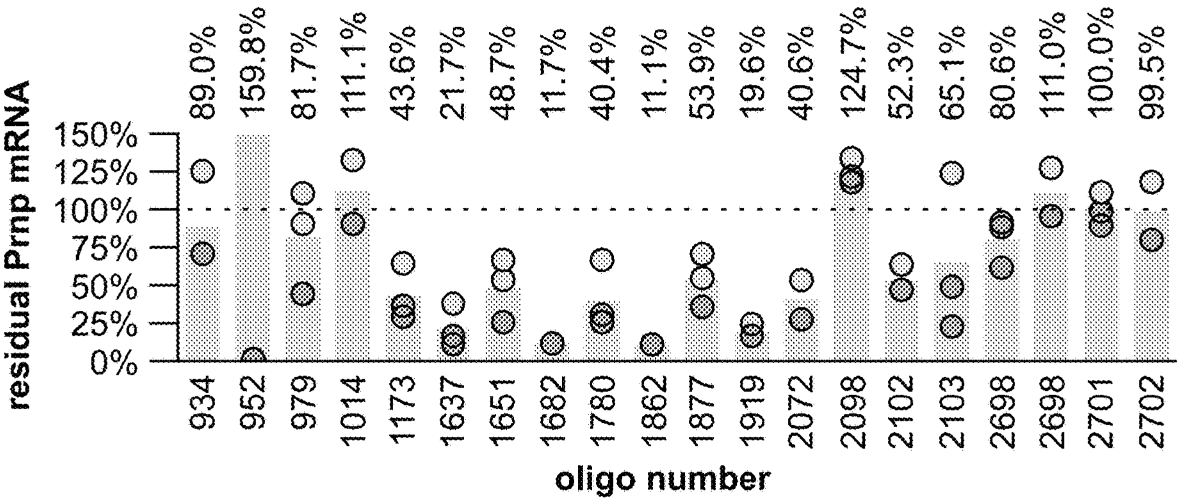
FIG. 1A-FIG. 1F depict efficacy of a divalent siRNA compound in mice with prion disease.

Novel PRNP target sequences are provided. Also provided are novel siRNAs that target the novel PRNP target sequences of the disclosure.

Unless otherwise specified, nomenclature used in connection with cell and tissue culture, molecular biology, immunology, microbiology, genetics and protein and nucleic acid chemistry and hybridization described herein are those well-known and commonly used in the art. Unless otherwise specified, the methods and techniques provided herein are performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and N2,N2-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester or phosphorothioate linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA")(also referred to in the art as "short interfering RNAs") refers to an RNA (or RNA analog) comprising between about 10-50 nucleotides (or nucleotide analogs), which is capable of directing or mediating RNA interference. In certain embodiments, a siRNA comprises between about 15-30 nucleotides or nucleotide analogs, or between about 16-25 nucleotides (or nucleotide analogs), or between about 18-23 nucleotides (or nucleotide analogs), or between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide, which may be derivatized include: the 5 position, e.g., 5-(2-amino)propyl uridine, 5-bromo uridine, 5-propyne uridine, 5-propenyl uridine, etc.; the 6 position, e.g., 6-(2-amino)propyl uridine; and the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs, such as those described in Herdewijn, Antisense Nucleic Acid Drug Dev., 2000 Aug. 10(4):297-310.

Nucleotide analogs may also comprise modifications to the sugar portion of the nucleotides. For example, the 2' OH-group may be replaced by a group selected from H, OR, R, F, Cl, Br, I, SH, SR, $NH_2$, NHR, $NR_2$, COOR, or, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions, which allow the nucleotide to perform its intended function, such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5):317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

The term "oligonucleotide" refers to a short polymer of nucleotides and/or nucleotide analogs.

The term "RNA analog" refers to a polynucleotide (e.g., a chemically synthesized polynucleotide) having at least one altered or modified nucleotide as compared to a corresponding unaltered or unmodified RNA, but retaining the same or similar nature or function as the corresponding unaltered or unmodified RNA. As discussed above, the oligonucleotides may be linked with linkages, which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Some RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA, which direct the degradative mechanism to other similar RNA sequences. Alternatively, RNAi can be initiated by the hand of man, for example, to silence the expression of target genes.

An RNAi agent, e.g., an RNA silencing agent, having a strand, which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules, which are substantially free of other cellular material, or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules, which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence," e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder.

The term "gain-of-function mutation" as used herein, refers to any mutation in a gene in which the protein encoded by said gene (i.e., the mutant protein) acquires a function not normally associated with the protein (i.e., the wild type protein) and causes or contributes to a disease or disorder. The gain-of-function mutation can be a deletion, addition, or substitution of a nucleotide or nucleotides in the gene, which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

As used herein, the term "target gene" is a gene whose expression is to be substantially inhibited or "silenced." This silencing can be achieved by RNA silencing, e.g., by cleaving the mRNA of the target gene or translational repression of the target gene. The term "non-target gene" is a gene whose expression is not to be substantially silenced. In one embodiment, the polynucleotide sequences of the target and non-target gene (e.g. mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homologue (e.g. an orthologue or paralogue) of the target gene.

A "target allele" is an allele (e.g., a SNP allele) whose expression is to be selectively inhibited or "silenced." This silencing can be achieved by RNA silencing, e.g., by cleaving the mRNA of the target gene or target allele by a siRNA. The term "non-target allele" is an allele whose expression is not to be substantially silenced. In certain embodiments, the target and non-target alleles can correspond to the same target gene. In other embodiments, the target allele corresponds to, or is associated with, a target gene, and the non-target allele corresponds to, or is associated with, a non-target gene. In one embodiment, the polynucleotide sequences of the target and non-target alleles can differ by one or more nucleotides. In another embodiment, the target and non-target alleles can differ by one or more allelic polymorphisms (e.g., one or more SNPs). In another embodiment, the target and non-target alleles can share less than 100% sequence identity.

The term "polymorphism" as used herein, refers to a variation (e.g., one or more deletions, insertions, or substitutions) in a gene sequence that is identified or detected when the same gene sequence from different sources or subjects (but from the same organism) are compared. For example, a polymorphism can be identified when the same gene sequence from different subjects are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared. In certain embodiments, the polymorphism is a single nucleotide polymorphism (SNP).

A variation in sequence between two alleles of the same gene within an organism is referred to herein as an "allelic polymorphism." In certain embodiments, the allelic polymorphism corresponds to a SNP allele. For example, the allelic polymorphism may comprise a single nucleotide variation between the two alleles of a SNP. The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene. In exemplary embodiments, the polymorphism is found in a coding region of the gene or in an untranslated region (e.g., a 5' UTR or 3' UTR) of the gene.

As used herein, the term "RNA silencing agent" refers to an RNA, which is capable of inhibiting or "silencing" the expression of a target gene. In certain embodiments, the RNA silencing agent is capable of preventing complete processing (e.g., the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small non-coding RNAs can be generated. Exemplary RNA silencing agents include siRNAs, miRNAs, siRNA-like duplexes, antisense oligonucleotides, GAPMER molecules, and dual-function oligonucleotides, as well as precursors thereof. In one embodiment, the RNA silencing agent is capable of inducing RNA interference. In another embodiment, the RNA silencing agent is capable of mediating translational repression.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, 2N-methylguanosine and 2,2N,N-dimethylguanosine.

The term "engineered," as in an engineered RNA precursor, or an engineered nucleic acid molecule, indicates that the precursor or molecule is not found in nature, in that all or a portion of the nucleic acid sequence of the precursor or molecule is created or selected by a human. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "microRNA" ("miRNA"), also known in the art as "small temporal RNAs" ("stRNAs"), refers to a small (10-50 nucleotide) RNA, which are genetically encoded (e.g., by viral, mammalian, or plant genomes) and are capable of directing or mediating RNA silencing. An "miRNA disorder" shall refer to a disease or disorder characterized by an aberrant expression or activity of a miRNA.

As used herein, the term "dual functional oligonucleotide" refers to a RNA silencing agent having the formula T-L-μ, wherein T is an mRNA targeting moiety, L is a linking moiety, and μ is a miRNA recruiting moiety. As used herein, the terms "mRNA targeting moiety," "targeting moiety," "mRNA targeting portion" or "targeting portion" refer to a domain, portion or region of the dual functional oligonucleotide having sufficient size and sufficient complementarity to a portion or region of an mRNA chosen or targeted for silencing (i.e., the moiety has a sequence sufficient to capture the target mRNA).

As used herein, the term "linking moiety" or "linking portion" refers to a domain, portion or region of the RNA-silencing agent which covalently joins or links the mRNA.

As used herein, the term "antisense strand" of an RNA silencing agent, e.g., an siRNA or RNA silencing agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g., an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "guide strand" refers to a strand of an RNA silencing agent, e.g., an antisense strand of an siRNA duplex or siRNA sequence, that enters into the RISC complex and directs cleavage of the target mRNA.

As used herein, the term "asymmetry," as in the asymmetry of the duplex region of an RNA silencing agent (e.g., the stem of an shRNA), refers to an inequality of bond strength or base pairing strength between the termini of the RNA silencing agent (e.g., between terminal nucleotides on a first strand or stem portion and terminal nucleotides on an opposing second strand or stem portion), such that the 5' end of one strand of the duplex is more frequently in a transient unpaired, e.g., single-stranded, state than 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, van der Waals interactions, and the like, between said nucleotides (or nucleotide analogs).

As used herein, the "5' end," as in 5' end of an antisense strand, refers to the 5' terminal nucleotides, e.g., between one and about 5 nucleotides at the 5' terminus of the antisense strand. As used herein, the "3' end," as in 3' end of a sense strand, refers to the region, e.g., a region of between one and about 5 nucleotides, that is complementary to the nucleotides of 5' end of the complementary antisense strand.

As used herein the term "destabilizing nucleotide" refers to a first nucleotide or nucleotide analog capable of forming a base pair with second nucleotide or nucleotide analog such that the base pair is of lower bond strength than a conventional base pair (i.e., Watson-Crick base pair). In certain embodiments, the destabilizing nucleotide is capable of forming a mismatch base pair with the second nucleotide. In other embodiments, the destabilizing nucleotide is capable of forming a wobble base pair with the second nucleotide. In yet other embodiments, the destabilizing nucleotide is capable of forming an ambiguous base pair with the second nucleotide.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of non-complementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

As used herein, term "universal nucleotide" (also known as a "neutral nucleotide") include those nucleotides (e.g. certain destabilizing nucleotides) having a base (a "universal base" or "neutral base") that does not significantly discriminate between bases on a complementary polynucleotide when forming a base pair. Universal nucleotides are predominantly hydrophobic molecules that can pack efficiently into antiparallel duplex nucleic acids (e.g., double-stranded DNA or RNA) due to stacking interactions. The base portion of universal nucleotides typically comprise a nitrogen-containing aromatic heterocyclic moiety.

As used herein, the terms "sufficient complementarity" or "sufficient degree of complementarity" mean that the RNA silencing agent has a sequence (e.g. in the antisense strand, mRNA targeting moiety or miRNA recruiting moiety), which is sufficient to bind the desired target RNA, respectively, and to trigger the RNA silencing of the target mRNA.

As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

Various methodologies of the instant invention include a step that involves comparing a value, level, feature, characteristic, property, etc. to a "suitable control," referred to interchangeably herein as an "appropriate control." A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and example are illustrative only and not intended to be limiting.

Various aspects of the invention are described in further detail in the following subsections.

I. siRNA Design

In some embodiments, siRNAs are designed as follows. First, a portion of the target gene (e.g., the PRNP gene. Cleavage of mRNA at these sites should eliminate translation of corresponding protein. Antisense strands were designed based on the target sequence and sense strands were designed to be complementary to the antisense strand. Hybridization of the antisense and sense strands forms the siRNA duplex. The antisense strand includes about 19 to 25 nucleotides, e.g., 19, 20, 21, 22, 23, 24 or 25 nucleotides. In other embodiments, the antisense strand includes 20, 21, 22 or 23 nucleotides. The sense strand includes about 14 to 25 nucleotides, e.g., 14, 15, 16, 17, 18, 19, 20, 21, 22, 23, 24 or 25 nucleotides. In other embodiments, the sense strand is 15 nucleotides. In other embodiments, the sense strand is 18 nucleotides. In other embodiments, the sense strand is 20 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention, provided that they retain the ability to mediate RNAi. Longer RNAi agents have been demonstrated to elicit an interferon or PKR response in certain mammalian cells, which may be undesirable. In certain embodiments, the RNAi agents of the invention do not elicit a PKR response (i.e., are of a sufficiently short length). However, longer RNAi agents may be useful, for example, in cell types incapable of generating a PKR response or in situations where the PKR response has been down-regulated or dampened by alternative means.

The sense strand sequence can be designed such that the target sequence is essentially in the middle of the strand. Moving the target sequence to an off-center position can, in some instances, reduce efficiency of cleavage by the siRNA. Such compositions, i.e., less efficient compositions, may be desirable for use if off-silencing of the wild-type mRNA is detected.

The antisense strand can be the same length as the sense strand and includes complementary nucleotides. In one embodiment, the strands are fully complementary, i.e., the strands are blunt-ended when aligned or annealed. In another embodiment, the strands align or anneal such that 1-, 2-, 3-, 4-, 5-, 6-, 7-, or 8-nucleotide overhangs are generated, i.e., 3' end of the sense strand extends 1, 2, 3, 4, 5, 6, 7, or 8 nucleotides further than 5' end of the antisense strand and/or 3' end of the antisense strand extends 1, 2, 3, 4, 5, 6, 7, or 8 nucleotides further than 5' end of the sense strand. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material.

To facilitate entry of the antisense strand into RISC (and thus increase or improve the efficiency of target cleavage and silencing), the base pair strength between 5' end of the sense strand and 3' end of the antisense strand can be altered, e.g., lessened or reduced, as described in detail in U.S. Pat. Nos. 7,459,547, 7,772,203 and 7,732,593, entitled "Methods and Compositions for Controlling Efficacy of RNA Silencing" (filed Jun. 2, 2003) and U.S. Pat. Nos. 8,309,704, 7,750,144, 8,304,530, 8,329,892 and 8,309,705, entitled "Methods and Compositions for Enhancing the Efficacy and Specificity of RNAi" (filed Jun. 2, 2003), the contents of which are incorporated in their entirety by this reference. In one embodiment of these aspects of the invention, the base-pair strength is less due to fewer G:C base pairs between 5' end of the first or antisense strand and 3' end of the second or sense strand than between 3' end of the first or antisense strand and 5' end of the second or sense strand. In another embodiment, the base pair strength is less due to at least one mismatched base pair between 5' end of the first or antisense strand and 3' end of the second or sense strand. In certain exemplary embodiments, the mismatched base pair is selected from the group consisting of G:A, C:A, C:U, G:G, A:A, C:C and U:U. In another embodiment, the base pair strength is less due to at least one wobble base pair, e.g., G:U, between 5' end of the first or antisense strand and 3' end of the second or sense strand. In another embodiment, the base pair strength is less due to at least one base pair comprising a rare nucleotide, e.g., inosine (I). In certain exemplary embodiments, the base pair is selected from the group consisting of an I:A, I:U and I:C. In yet another embodiment, the base pair strength is less due to at least one base pair comprising a modified nucleotide. In certain exemplary embodiments, the modified nucleotide is selected from the group consisting of 2-amino-G, 2-amino-A, 2,6-diamino-G, and 2,6-diamino-A.

The design of siRNAs suitable for targeting the PRNP target is described in detail below. siRNAs can be designed according to the above exemplary teachings for any other target sequences found in the PRNP gene. Moreover, the technology is applicable to targeting any other target sequences, e.g., non-disease-causing target sequences.

To validate the effectiveness by which siRNAs destroy mRNAs (e.g., PRNP mRNA), the siRNA can be incubated with cDNA (e.g., PRNP cDNA) in a *Drosophila*-based in vitro mRNA expression system. Radiolabeled with $^{32}P$, newly synthesized mRNAs (e.g., PRNP mRNA) are detected autoradiographically on an agarose gel. The presence of cleaved mRNA indicates mRNA nuclease activity. Suitable controls include omission of siRNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence. Sites of siRNA-mRNA complementation are selected which result in optimal mRNA specificity and maximal mRNA cleavage.

II. RNAi Agents

The present invention includes siRNA molecules designed, for example, as described above. The siRNA molecules of the invention can be chemically synthesized, or can be transcribed in vitro from a DNA template, or in vivo from e.g., shRNA, or by using recombinant human DICER enzyme, to cleave in vitro transcribed dsRNA templates into pools of 20-, 21- or 23-bp duplex RNA mediating RNAi. The siRNA molecules can be designed using any method known in the art.

In one aspect, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. Thus, RNAi agents of the present invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides (Brummelkamp et al., 2002; Lee et al., 2002, Supra; Miyagishi et al., 2002; Paddison et al., 2002, supra; Paul et al., 2002, supra; Sui et al., 2002 supra; Yu et al., 2002, supra. More information about shRNA design and use can be found on the internet at the following addresses: katandin.cshl.org:9331/RNAi/docs/BseRI-BamHI_Strategy.pdf and katandin.cshl.org:9331/RNAi/docs/Web_version_of_PCR_strategy1.pdf).

Expression constructs of the present invention include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems, such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct. (Tuschl, T., 2002, Supra).

Synthetic siRNAs can be delivered into cells by methods known in the art, including cationic liposome transfection and electroporation. To obtain longer term suppression of the target genes (e.g., PRNP genes) and to facilitate delivery under certain circumstances, one or more siRNA can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T., 2002, supra) capable of expressing functional double-stranded siRNAs; (Bagella et al., 1998; Lee et al., 2002, supra; Miyagishi et al., 2002, supra; Paul et al., 2002, supra; Yu et al., 2002, supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, supra; Miyagishi et al., 2002, supra; Paul et al., 2002, supra; Yu et al., 2002), supra; Sui et al., 2002, supra). Constructs containing siRNA sequence under the control of T7 promoter also make functional siRNAs when co-transfected into the cells with a vector expressing T7 RNA polymerase (Jacque et al., 2002, supra). A single construct may contain multiple sequences coding for siRNAs, such as multiple regions of the gene encoding PRNP, targeting the same gene or multiple genes, and can be driven, for example, by separate PolIII promoter sites.

Animal cells express a range of noncoding RNAs of approximately 22 nucleotides termed micro RNA (miRNAs), which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific mRNA targets in mammalian cells (Zeng et al., 2002, supra). When expressed by DNA vectors containing polymerase III promoters, micro-RNA designed hairpins can silence gene expression (McManus et al., 2002, supra). MicroRNAs targeting polymorphisms may also be useful for blocking translation of mutant proteins, in the absence of siRNA-mediated gene-silencing. Such applications may be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by "high-pressure" delivery technique, a rapid injection (within 5 seconds) of a large volume of siRNA containing solution into animal via the tail vein (Liu et al., 1999, supra; McCaffrey et al., 2002, supra; Lewis et al., 2002. Nanoparticles and liposomes can also be used to deliver siRNA into animals. In certain exemplary embodiments, recombinant adeno-associated viruses (rAAVs) and their associated vectors can be used to deliver one or more siRNAs into cells, e.g., neural cells (e.g., brain cells) (US Patent Applications 2014/0296486, 2010/0186103, 2008/0269149, 2006/0078542 and 2005/0220766).

The nucleic acid compositions of the invention include both unmodified siRNAs and modified siRNAs, such as crosslinked siRNA derivatives or derivatives having non-nucleotide moieties linked, for example to their 3' or 5' ends. Modifying siRNA derivatives in this way may improve cellular uptake or enhance cellular targeting activities of the resulting siRNA derivative, as compared to the corresponding siRNA, and are useful for tracing the siRNA derivative in the cell, or improving the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA, which will be targeted by the siRNA generated from the engineered RNA precursor, and will be depleted from the cell or organism, leading to a decrease in the concentration of the protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability and/or half-life. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules of the present invention can also be labeled using any method known in the art. For instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3H$, $^{32}P$ or another appropriate isotope.

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis), generated (e.g., enzymatically generated), or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, such as about 200-500, for example, about 250, 300, 350, 400 or 450 nucleotides in length) acting as effectors of RNAi. (Brondani et al., Proc Natl Acad Sci USA. 2001 Dec. 4; 98(25):14428-33. Epub 2001 Nov. 27.)

III. Anti-PRNP RNA Silencing Agents

In one embodiment, the present invention provides novel anti-PRNP RNA silencing agents (e.g., siRNA, shRNA, and antisense oligonucleotides), methods of making said RNA silencing agents, and methods (e.g., research and/or therapeutic methods) for using said improved RNA silencing agents (or portions thereof) for RNA silencing of PRNP protein. The RNA silencing agents comprise an antisense strand (or portions thereof), wherein the antisense strand has sufficient complementary to a target PRNP mRNA to mediate an RNA-mediated silencing mechanism (e.g. RNAi).

In certain embodiments, siRNA compounds are provided having one or any combination of the following properties: (1) fully chemically-stabilized (i.e., no unmodified 2'-OH residues); (2) asymmetry; (3) 11-20 base pair duplexes; (4) greater than 50% 2'-methoxy modifications, although an alternating pattern of chemically-modified nucleotides (e.g., 2'-fluoro and 2'-methoxy modifications), are also contemplated; and (5) single-stranded, tails of 2-8 bases with at least two phosphorothioate internucleotide linkages. In certain embodiments, the number of phosphorothioate modifications is varied from 4 to 16 total. In certain embodiments, the number of phosphorothioate modifications is varied from 8 to 13 total.

In certain embodiments, the siRNA compounds described herein can be conjugated to a variety of targeting agents, including, but not limited to, cholesterol, docosahexaenoic acid (DHA), phenyltropanes, cortisol, vitamin A, vitamin D, N-acetylgalactosamine (GalNac), and gangliosides.

Certain compounds of the invention having the structural properties described above and herein may be referred to as "hsiRNA-ASP" (hydrophobically-modified, small interfering RNA, featuring an advanced stabilization pattern). In addition, this hsiRNA-ASP pattern showed a dramatically improved distribution through the brain, spinal cord, delivery to liver, placenta, kidney, spleen and several other tissues, making them accessible for therapeutic intervention.

The compounds of the invention can be described in the following aspects and embodiments.

A double stranded RNA (dsRNA) comprising an antisense strand of UGAAUACUCACAAAGUGCAUU (SEQ ID NO: 1) and a sense strand of ACUUUGUGAGUAUUCA (SEQ ID NO: 2).

In certain embodiments, dsRNA comprises: an antisense strand of (mU)#(fG)#(mA)(fA)(fU)(fA)(mC)(fU)(mC)(fA)(mC)(fA)(mA)(fA)(mG)(fU)(mG)(mC)(mA)#ex(mU)#ex(fU) (SEQ ID NO: 3); and a sense strand of (mA)#(mC)#(mU)(fU)(mU)(fG)(mU)(fG)(mA)(fG)(mU)(mA)(mU)(fU)#(mC)#(mA) (SEQ ID NO: 4), wherein "m" corresponds to a 2'-O-methyl modification, "f" corresponds to a. 2'-fluoro modification, "#" corresponds to a phosphorothioate internucleotide linkage, and "ex" corresponds to a modified internucleotide linkage of Formula I.

In certain embodiments, dsRNA comprises: an antisense strand of VP(mU)#(fG)#(mA)(fA)(fU)(fA)(mC)(fU)(mC)(fA)(mC)(fA)(mA)(fA)(mG)(fU)(mG)(mC)(mA)#ex(mU)#ex(fU) (SEQ ID NO: 5); and a sense strand of (mA)#(mC)#(mU)(fU)(mU)(fG)(mU)(fG)(mA)(fG)(mU)(mA)(mU)(fU)#(mC)#(mA) (SEQ ID NO: 4), wherein "m" corresponds to a 2'-O-methyl modification, "f" corresponds to a. 2'-fluoro modification, "#" corresponds to a phosphorothioate internucleotide linkage, "ex" corresponds to a modified internucleotide linkage of Formula I, and "VP" corresponds to a 5' vinyl phosphonate.

a) Design of Anti-PRNP siRNA Molecules

An siRNA molecule of the application is a duplex made of a sense strand and complementary antisense strand, the antisense strand having sufficient complementary to a PRNP mRNA to mediate RNAi. In certain embodiments, the siRNA molecule has a length from about 10-50 or more nucleotides, i.e., each strand comprises 10-50 nucleotides (or nucleotide analogs). In other embodiments, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementary to a target region. In certain embodiments, the strands are aligned such that there are at least 1, 2, 3, 4, 5, 6, 7, 8, 9, or 10 bases at the end of the strands, which do not align (i.e., for which no complementary bases occur in the opposing strand), such that an overhang of 1, 2, 3, 4, 5, 6, 7, 8, 9, or 10 residues occurs at one or both ends of the duplex when strands are annealed.

Usually, siRNAs can be designed by using any method known in the art, for instance, by using the following protocol:

1. The siRNA should be specific for a target sequence, e.g., a target sequence set forth in the Examples. The first strand should be complementary to the target sequence, and the other strand is substantially complementary to the first strand. (See Examples for exemplary sense and antisense strands.) Exemplary target sequences are selected from any region of the target gene that leads to potent gene silencing. Regions of the target gene include, but are not limited to, 5' untranslated region (5'-UTR) of a target gene, 3' untranslated region (3'-UTR) of a target gene, an exon of a target gene, or an intron of a target gene. Cleavage of mRNA at these sites should eliminate translation of corresponding PRNP protein. Target sequences from other regions of the PRNP gene are also suitable for targeting. A sense strand is designed based on the target sequence.
2. The sense strand of the siRNA is designed based on the sequence of the selected target site. In certain embodiments, the sense strand includes about 15 to 25 nucleotides, e.g., 15, 16, 17, 18, 19, 20, 21, 22, 23, 24 or 25 nucleotides. In certain embodiments, the sense strand includes 15, 16, 17, 18, 19, or 20 nucleotides. In certain embodiments, the sense strand is 15 nucleotides in length. In certain embodiments, the sense strand is 18 nucleotides in length. In certain embodiments, the sense strand is 20 nucleotides in length. The skilled artisan will appreciate, however, that siRNAs having a length of less than 15 nucleotides or greater than 25 nucleotides can also function to mediate RNAi.

Accordingly, siRNAs of such length are also within the scope of the instant invention, provided that they retain the ability to mediate RNAi. Longer RNA silencing agents have been demonstrated to elicit an interferon or Protein Kinase R (PKR) response in certain mammalian cells which may be undesirable. In certain embodiments, the RNA silencing agents of the invention do not elicit a PKR response (i.e., are of a sufficiently short length). However, longer RNA silencing agents may be useful, for example, in cell types incapable of generating a PKR response or in situations where the PKR response has been down-regulated or dampened by alternative means.

The siRNA molecules of the invention have sufficient complementarity with the target sequence such that the siRNA can mediate RNAi. In general, siRNA containing nucleotide sequences sufficiently complementary to a target sequence portion of the target gene to effect RISC-mediated cleavage of the target gene are contemplated. Accordingly, in a certain embodiment, the antisense strand of the siRNA is designed to have a sequence sufficiently complementary to a portion of the target. For example, the antisense strand may have 100% complementarity to the target site. However, 100% complementarity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% complementarity, between the antisense strand and the target RNA sequence is contemplated. The present application has the advantage of being able to tolerate certain sequence variations to enhance efficiency and specificity of RNAi. In one embodiment, the antisense strand has 4, 3, 2, 1, or 0 mismatched nucleotide(s) with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and the percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 7 (e.g., 2, 3, 4, 5, 6 or 7), or 1 to 4, e.g., 2, 3 or 4 nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus, in another embodiment, the nucleic acid molecules may have a 3' overhang of 2 nucleotides, such as TT. The overhanging nucleotides may be either RNA or DNA. As noted above, it is desirable to choose a target region wherein the mutant: wild type mismatch is a purine:purine mismatch.
4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.
5. Select one or more sequences that meet your criteria for evaluation.

Further general information about the design and use of siRNA may be found in "The siRNA User Guide," available at The Max-Plank-Institut fur Biophysikalische Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50 °C. or 70 °C. hybridization for 12-16 hours; followed by washing). Additional hybridization conditions include hybridization at 70 °C. in 1×SSC or 50 °C. in 1×SSC, 50% formamide followed by washing at 70 °C. in 0.3×SSC or hybridization at 70 °C. in 4×SSC or 50 °C. in 4×SSC, 50% formamide followed by washing at 67 °C. in 1×SSC. The hybridization temperature for hybrids anticipated to be less than 50 base pairs in length should be 5-10 °C. less than the melting temperature ($T_m$) of the hybrid, where $T_m$ is determined according to the following equations. For hybrids less than 18 base pairs in length, $T_m$(°C.)=2(# of A+T bases)+4(# of G+C bases). For hybrids between 18 and 49 base pairs in length, $T_m$(°C.)=81.5+16.6(log 10 [Na+])+0.41(% G+C)−(600/N), where N is the number of bases in the hybrid, and [Na+] is the concentration of sodium ions in the hybridization buffer ([$Na^+$] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant PRNP mRNA), the siRNA may be incubated with target cDNA (e.g., PRNP cDNA) in a *Drosophila*-based in vitro mRNA expression system. Radiolabeled with $^{32}P$, newly synthesized target mRNAs (e.g., PRNP mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

Anti-PRNP siRNAs may be designed to target any of the target sequences described supra. Said siRNAs comprise an antisense strand, which is sufficiently complementary with the target sequence to mediate silencing of the target sequence. In certain embodiments, the RNA silencing agent is a siRNA.

Sites of siRNA-mRNA complementation are selected, which result in optimal mRNA specificity and maximal mRNA cleavage.

b) siRNA-Like Molecules siRNA-like molecules of the invention have a sequence (i.e., have a strand having a sequence) that is "sufficiently complementary" to a target sequence of an PRNP mRNA to direct gene silencing either by RNAi or translational repression. siRNA-like molecules are designed in the same way as siRNA molecules, but the degree of sequence identity between the sense strand and target RNA approximates that observed between a miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further embodiment, the "bulge" is centered at nucleotide positions 12 and 13 from the 5' end of the miRNA molecule.

c) Short Hairpin RNA (shRNA) Molecules

In certain featured embodiments, the instant invention provides shRNAs capable of mediating RNA silencing of an PRNP target sequence with enhanced selectivity. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides, which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the present application are artificial constructs based on these naturally occurring pre-miRNAs, but which are engineered to deliver desired RNA silencing agents (e.g., siRNAs of the invention). By substituting the stem sequences of the pre-miRNA with sequence complementary to the target mRNA, a shRNA is formed. The shRNA is processed by the entire gene silencing pathway of the cell, thereby efficiently mediating RNAi.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs (or engineered precursor RNAs) of the instant invention, one portion of the duplex stem is a nucleic acid sequence that is complementary (or anti-sense) to the PRNP target sequence. In certain embodiments, one strand of the stem portion of the shRNA is sufficiently complementary (e.g., antisense) to a target RNA (e.g., mRNA) sequence to mediate degradation or cleavage of said target RNA via RNA interference (RNAi). Thus, engineered RNA precursors include a duplex stem with two portions and a loop connecting the two stem portions. The antisense portion can be on 5' or 3' end of the stem. The stem portions of a shRNA are about 15 to about 50 nucleotides in length. In certain embodiments, the two stem portions are about 18 or 19 to about 21, 22, 23, 24, 25, 30, 35, 37, 38, 39, or 40 or more nucleotides in length. In certain embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. In certain embodiments, a loop consists of or comprises a "tetraloop" sequence. Exemplary tetraloop sequences include, but are not limited to, the sequences GNRA, where N is any nucleotide and R is a purine nucleotide, GGGG, and UUUU.

In certain embodiments, shRNAs of the present application include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA (e.g., PRNP mRNA), for example, from a region 100 to 200 or 300 nucleotides upstream or downstream of the start of translation. In general, the sequence can be selected from any portion of the target RNA (e.g., mRNA) including 5' UTR (untranslated region), coding sequence, or 3' UTR. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include, in the duplex stem, the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro.

In certain embodiments, shRNAs of the invention include miRNA sequences, optionally end-modified miRNA sequences, to enhance entry into RISC. The miRNA sequence can be similar or identical to that of any naturally occurring miRNA (see e.g. The miRNA Registry; Griffiths-Jones S, Nuc. Acids Res., 2004). Over one thousand natural miRNAs have been identified to date and together they are thought to comprise about 1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans*, zebrafish, *Arabidopsis thalania, Mus musculus*, and *Rattus norvegicus* as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex, but only one strand is taken up by the RISC complex to direct gene silencing. Certain miRNAs, e.g., plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between a miRNA and its target mRNA is believed to determine its mechanism of action. For example, perfect or near-perfect complementarity between a miRNA and its target mRNA is predictive of a cleavage mechanism (Yekta et al., Science, 2004), whereas less than perfect complementarity is predictive of a translational repression mechanism. In certain embodiments, the miRNA sequence is that of a naturally-occurring miRNA sequence, the aberrant expression or activity of which is correlated with a miRNA disorder.

d) Dual Functional Oligonucleotide Tethers

In other embodiments, the RNA silencing agents of the present invention include dual functional oligonucleotide tethers useful for the intercellular recruitment of a miRNA. Animal cells express a range of miRNAs, noncoding RNAs of approximately 22 nucleotides which can regulate gene expression at the post transcriptional or translational level. By binding a miRNA bound to RISC and recruiting it to a target mRNA, a dual functional oligonucleotide tether can repress the expression of genes involved e.g., in the arteriosclerotic process. The use of oligonucleotide tethers offers several advantages over existing techniques to repress the expression of a particular gene. First, the methods described herein allow an endogenous molecule (often present in abundance), a miRNA, to mediate RNA silencing. Accordingly, the methods described herein obviate the need to introduce foreign molecules (e.g., siRNAs) to mediate RNA silencing. Second, the RNA-silencing agents and the linking moiety (e.g., oligonucleotides such as the 2'-O-methyl oligonucleotide), can be made stable and resistant to nuclease activity. As a result, the tethers of the present invention can be designed for direct delivery, obviating the need for indirect delivery (e.g. viral) of a precursor molecule or plasmid designed to make the desired agent within the cell. Third, tethers and their respective moieties, can be designed to conform to specific mRNA sites and specific miRNAs. The designs can be cell and gene product specific. Fourth, the methods disclosed herein leave the mRNA intact, allowing one skilled in the art to block protein synthesis in short pulses using the cell's own machinery. As a result, these methods of RNA silencing are highly regulatable.

The dual functional oligonucleotide tethers ("tethers") of the invention are designed such that they recruit miRNAs (e.g., endogenous cellular miRNAs) to a target mRNA so as to induce the modulation of a gene of interest. In certain embodiments, the tethers have the formula T-L-μ, wherein T is an mRNA targeting moiety, L is a linking moiety, and μ is a miRNA recruiting moiety. Any one or more moiety may be double stranded. In certain embodiments, each moiety is single stranded.

Moieties within the tethers can be arranged or linked (in 5' to 3' direction) as depicted in the formula T-L-μ (i.e., 3' end of the targeting moiety linked to the 5' end of the linking moiety and 3' end of the linking moiety linked to the 5' end of the miRNA recruiting moiety). Alternatively, the moieties can be arranged or linked in the tether as follows: μ-T-L (i.e., 3' end of the miRNA recruiting moiety linked to the 5' end of the linking moiety and 3' end of the linking moiety linked to the 5' end of the targeting moiety).

The mRNA targeting moiety, as described above, is capable of capturing a specific target mRNA. According to the invention, expression of the target mRNA is undesirable, and, thus, translational repression of the mRNA is desired. The mRNA targeting moiety should be of sufficient size to effectively bind the target mRNA. The length of the targeting moiety will vary greatly, depending, in part, on the length of the target mRNA and the degree of complementarity between the target mRNA and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a certain embodiment, the targeting moiety is about 15 to about 25 nucleotides in length.

The miRNA recruiting moiety, as described above, is capable of associating with a miRNA. According to the present application, the miRNA may be any miRNA capable of repressing the target mRNA. Mammals are reported to have over 250 endogenous miRNAs (Lagos-Quintana et al. (2002) Current Biol. 12:735-739; Lagos-Quintana et al. (2001) Science 294:858-862; and Lim et al. (2003) Science 299:1540). In various embodiments, the miRNA may be any art-recognized miRNA.

The linking moiety is any agent capable of linking the targeting moieties such that the activity of the targeting moieties is maintained. Linking moieties can be oligonucleotide moieties comprising a sufficient number of nucleotides, such that the targeting agents can sufficiently interact with their respective targets. Linking moieties have little or no sequence homology with cellular mRNA or miRNA sequences. Exemplary linking moieties include one or more 2'-O-methylnucleotides, e.g., 2'-β-methyladenosine, 2'-O-methylthymidine, 2'-O-methylguanosine or 2'-O-methyluridine.

e) Gene Silencing Oligonucleotides

In certain exemplary embodiments, gene expression (i.e., PRNP gene expression) can be modulated using oligonucleotide-based compounds comprising two or more single stranded antisense oligonucleotides that are linked through their 5'-ends that allow the presence of two or more accessible 3'-ends to effectively inhibit or decrease PRNP gene expression. Such linked oligonucleotides are also known as Gene Silencing Oligonucleotides (GSOs). (See, e.g., U.S. Pat. No. 8,431,544 assigned to Idera Pharmaceuticals, Inc., incorporated herein by reference in its entirety for all purposes.)

The linkage at the 5' ends of the GSOs is independent of the other oligonucleotide linkages and may be directly via 5', 3' or 2'hydroxyl groups, or indirectly, via a non-nucleotide linker or a nucleoside, utilizing either the 2' or 3' hydroxyl positions of the nucleoside. Linkages may also utilize a functionalized sugar or nucleobase of a 5' terminal nucleotide.

GSOs can comprise two identical or different sequences conjugated at their 5'-5' ends via a phosphodiester, phosphorothioate or non-nucleoside linker. Such compounds may comprise 15 to 27 nucleotides that are complementary to specific portions of mRNA targets of interest for antisense down regulation of a gene product. GSOs that comprise identical sequences can bind to a specific mRNA via Watson-Crick hydrogen bonding interactions and inhibit protein expression. GSOs that comprise different sequences are able to bind to two or more different regions of one or more mRNA target and inhibit protein expression. Such compounds are comprised of heteronucleotide sequences complementary to target mRNA and form stable duplex structures through Watson-Crick hydrogen bonding. Under certain conditions, GSOs containing two free 3'-ends (5'-5'-attached antisense) can be more potent inhibitors of gene expression than those containing a single free 3'-end or no free 3'-end.

In some embodiments, the non-nucleotide linker is glycerol or a glycerol homolog of the formula HO—$(CH_2)_o$—CH(OH)—$(CH_2)_p$—OH, wherein o and p independently are integers from 1 to about 6, from 1 to about 4 or from 1 to about 3. In some other embodiments, the non-nucleotide linker is a derivative of 1,3-diamino-2-hydroxypropane. Some such derivatives have the formula HO—$(CH_2)$m-C(O)NH—$CH_2$—CH(OH)—$CH_2$—NHC(O)—$(CH_2)_m$—OH, wherein m is an integer from 0 to about 10, from 0 to about 6, from 2 to about 6 or from 2 to about 4.

Some non-nucleotide linkers permit attachment of more than two GSO components. For example, the non-nucleotide linker glycerol has three hydroxyl groups to which GSO components may be covalently attached. Some oligonucleotide-based compounds of the invention, therefore, comprise two or more oligonucleotides linked to a nucleotide or a non-nucleotide linker. Such oligonucleotides according to the invention are referred to as being “branched.”

In certain embodiments, GSOs are at least 14 nucleotides in length. In certain exemplary embodiments, GSOs are 15 to 40 nucleotides long or 20 to 30 nucleotides in length. Thus, the component oligonucleotides of GSOs can independently be 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

These oligonucleotides can be prepared by the art recognized methods, such as phosphoramidate or H-phosphonate chemistry, which can be carried out manually or by an automated synthesizer. These oligonucleotides may also be modified in a number of ways without compromising their ability to hybridize to mRNA. Such modifications may include at least one internucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate hydroxyl, acetamidate, carboxymethyl ester, or a combination of these and other internucleotide linkages between 5' end of one nucleotide and 3' end of another nucleotide, in which 5' nucleotide phosphodiester linkage has been replaced with any number of chemical groups.

V. Modified Anti-PRNP RNA Silencing Agents

In certain aspects of the invention, an RNA silencing agent (or any portion thereof) of the present application, as described supra, may be modified, such that the activity of the agent is further improved. For example, the RNA silencing agents described in Section II supra, may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the present application may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In certain embodiments, the RNA silencing agents of the present application are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is contemplated because it has relatively minor effect on the stability of the RNA duplex or the duplex formed by the guide strand of the RNA silencing agent and the target mRNA. Exemplary universal nucleotides include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In certain embodiments, the universal nucleotide is an inosine residue or a naturally occurring analog thereof.

In certain embodiments, the RNA silencing agents of the invention are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destablilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In certain embodiments, the destabilizing nucleotide is introduced in the same strand or strand portion that contains the specificity-determining nucleotide.

2) Modifications to Enhance Efficacy and Specificity

In certain embodiments, the RNA silencing agents of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the present application or an siRNA produced from a shRNA) into RISC in favor of the sense strand, such that the antisense strand preferentially guides cleavage or translational repression of a target mRNA, and thus increasing or improving the efficiency of target cleavage and silencing. In certain embodiments, the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of an RNA silencing agent of the present application may be enhanced such that there are fewer G:C base pairs between the 5' end of the first or antisense strand and 3' end of the sense strand portion than between 3' end of the first or antisense strand and 5' end of the sense strand portion. In another embodiment, the asymmetry of an RNA silencing agent of the invention may be enhanced such that there is at least one mismatched base pair between 5' end of the first or antisense strand and 3' end of the sense strand portion. In certain embodiments, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). In certain embodiments, the base pair is selected from the group consisting of an I:A, I:U and I:C. In yet another embodiment, the asymmetry of an RNA silencing agent of the invention may be enhanced such that there is at least one base pair comprising a modified nucleotide. In certain embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present application can be modified to improve stability in serum or in growth medium for cell cultures. In order to enhance the stability, 3'-residues may be stabilized against degradation, e.g., they may be selected such that they consist of purine nucleotides, such as adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a one aspect, the present application features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In one aspect, the present application features RNA silencing agents that are at least 80% chemically modified. In certain embodiments, the RNA silencing agents may be fully chemically modified, i.e., 100% of the nucleotides are chemically modified. In another aspect, the present application features RNA silencing agents comprising 2'-OH ribose groups that are at least 80% chemically modified. In certain embodiments, the RNA silencing agents comprise 2'-OH ribose groups that are about 80%, 85%, 90%, 95%, or 100% chemically modified.

In certain embodiments, the RNA silencing agents may contain at least one modified nucleotide analogue. The nucleotide analogues may be located at positions where the target-specific silencing activity, e.g., the RNAi mediating activity or translational repression activity is not substantially affected, e.g., in a region at 5'-end and/or 3'-end of the siRNA molecule. Moreover, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In certain embodiments, the modifications are 2'-fluoro, 2'-amino and/or 2'-thio modifications. Modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a certain embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moities of the instant invention. Additional modified residues include, deoxy-abasic, inosine, N3-methyl-uridine, N6,N6-dimethyl-adenosine, pseudouridine, purine ribonucleoside and ribavirin. In a certain embodiment, the 2' moiety is a methyl group such that the linking moiety is a 2'-O-methyl oligonucleotide.

In a certain embodiment, the RNA silencing agent of the present application comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-O,4'-C-ethylene-bridged nucleic acids, with possible modifications such as 2'-deoxy-2"-fluorouridine. Moreover, LNAs increase the specificity of oligonucleotides by constraining the sugar moiety into 3'-endo conformation, thereby pre-organizing the nucleotide for base pairing and increasing the melting temperature of the oligonucleotide by as much as 10 °C. per base.

In another exemplary embodiment, the RNA silencing agent of the present application comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone, which is highly resistant to nuclease digestion and imparts improved binding specificity to the molecule (Nielsen, et al., Science, (2001), 254: 1497-1500).

Also contemplated are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino) propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the present application includes RNA silencing agents having two complementary strands of nucleic acid, wherein the two strands are crosslinked. The present application also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an 0 with an S, in the phosphate backbone, e.g., the provision of a phosphorothioate modification, on the U or the A or both, especially on an antisense strand; e.g., with the replacement of a O with an S; (c) replacement of the U with a C5 amino linker; (d) replacement of an A with a G (sequence changes can be located on the sense strand and not the antisense strand in certain embodiments); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a O with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

Heavily Modified RNA Silencing Agents

In certain embodiments, the RNA silencing agent comprises at least 80% chemically modified nucleotides. In certain embodiments, the RNA silencing agent is fully chemically modified, i.e., 100% of the nucleotides are chemically modified.

In certain embodiments, the RNA silencing agent is 2'-O-methyl rich, i.e., comprises greater than 50% 2'-O-methyl content. In certain embodiments, the RNA silencing agent comprises at least about 55%, 60%, 65%, 70%, 75%, 80%, 85%, 90%, 95%, or 100% 2'-O-methyl nucleotide content. In certain embodiments, the RNA silencing agent comprises at least about 70% 2'-O-methyl nucleotide modifications. In certain embodiments, the RNA silencing agent comprises between about 70% and about 90% 2'-O-methyl nucleotide modifications. In certain embodiments, the RNA silencing agent is a dsRNA comprising an antisense strand and sense strand. In certain embodiments, the antisense strand comprises at least about 70% 2'-O-methyl nucleotide modifications. In certain embodiments, the antisense strand comprises between about 70% and about 90% 2'-O-methyl nucleotide modifications. In certain embodiments, the sense strand comprises at least about 70% 2'-O-methyl nucleotide modifications. In certain embodiments, the sense strand comprises between about 70% and about 90% 2'-O-methyl nucleotide modifications. In certain embodiments, the sense strand comprises between 100% 2'-O-methyl nucleotide modifications.

2'-O-methyl rich RNA silencing agents and specific chemical modification patterns are further described in U.S. Ser. No. 16/550,076 (filed Aug. 23, 2019) and U.S. Ser. No. 62/891,185 (filed Aug. 23, 2019), each of which is incorporated herein by reference.

Internucleotide Linkage Modifications

In certain embodiments, at least one internucleotide linkage, intersubunit linkage, or nucleotide backbone is modified in the RNA silencing agent. In certain embodiments, all of the internucleotide linkages in the RNA silencing agent are modified. In certain embodiments, the modified internucleotide linkage comprises a phosphorothioate internucleotide linkage. In certain embodiments, the RNA silencing agent comprise 1, 2, 3, 4, 5, 6, 7, 8, 9, 10, 11, 12, 13, 14, 15, 16, 17, 18, 19, 20, 21, 22, 23, 24, or 25 phosphorothioate internucleotide linkages. In certain embodiments, the RNA silencing agent comprises 4-16 phosphorothioate internucleotide linkages. In certain embodiments, the RNA silencing agent comprises 8-13 phosphorothioate internucleotide linkages. In certain embodiments, the RNA silencing agent is a dsRNA comprising an antisense strand and a sense strand, each comprising a 5' end and a 3' end. In certain embodiments, the nucleotides at positions 1 and 2 from the 5' end of sense strand are connected to adjacent ribonucleotides via phosphorothioate internucleotide linkages. In certain embodiments, the nucleotides at positions 1 and 2 from the 3' end of sense strand are connected to adjacent ribonucleotides via phosphorothioate internucleotide linkages. In certain embodiments, the nucleotides at positions 1 and 2 from the 5' end of antisense strand are connected to adjacent ribonucleotides via phosphorothioate internucleotide linkages. In certain embodiments, the nucleotides at positions 1-2 to 1-8 from the 3' end of antisense strand are connected to adjacent ribonucleotides via phosphorothioate internucleotide linkages. In certain embodiments, the nucleotides at positions 1-2, 1-3, 1-4, 1-5, 1-6, 1-7, or 1-8 from 3' end of antisense strand are connected to adjacent ribonucleotides via phosphorothioate internucleotide linkages. In certain embodiments, the nucleotides at positions 1-2 to 1-7 from 3' end of antisense strand are connected to adjacent ribonucleotides via phosphorothioate internucleotide linkages.

In one aspect, the disclosure provides a modified oligonucleotide, said oligonucleotide having a 5' end, a 3' end, that is complementary to a target, wherein the oligonucleotide comprises a sense and antisense strand, and at least one modified intersubunit linkage of Formula (I):

(I)

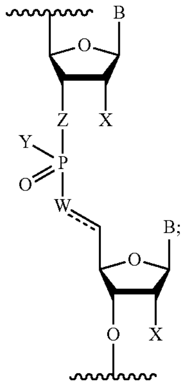

wherein:

B is a base pairing moiety;

W is selected from the group consisting of O, $OCH_2$, OCH, $CH_2$, and CH;

X is selected from the group consisting of halo, hydroxy, and $C_{1-6}$ alkoxy;

Y is selected from the group consisting of $O^-$, OH, OR, $NH^-$, $NH_2$, $S^-$, and SH;

Z is selected from the group consisting of O and $CH_2$;

R is a protecting group; and

⎓ is an optional double bond.

In an embodiment of Formula (I), when W is CH, ⎓ is a double bond.

In an embodiment of Formula (I), when W selected from the group consisting of O, $OCH_2$, OCH, $CH_2$, ⎓ is a single bond.

In an embodiment of Formula (I), when Y is $O^-$, either Z or W is not O.

In an embodiment of Formula (I), Z is $CH_2$ and W is $CH_2$. In another embodiment, the modified intersubunit linkage of Formula (I) is a modified intersubunit linkage of Formula (II):

(II)

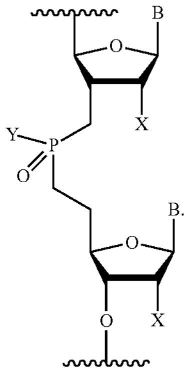

In an embodiment of Formula (I), Z is $CH_2$ and W is O. In another embodiment, wherein the modified intersubunit linkage of Formula (I) is a modified intersubunit linkage of Formula (III):

(III)

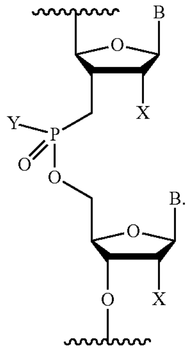

In an embodiment of Formula (I), Z is O and W is $CH_2$. In another embodiment, the modified intersubunit linkage of Formula (I) is a modified intersubunit linkage of Formula (IV):

(IV)

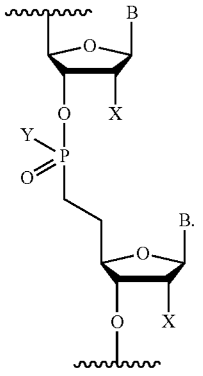

In an embodiment of Formula (I), Z is O and W is CH. In another embodiment, the modified intersubunit linkage of Formula (I) is a modified intersubunit linkage of Formula V:

(V)

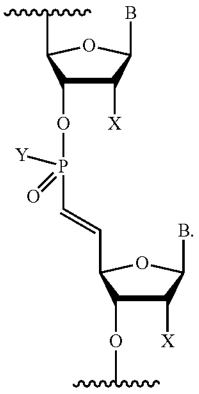

In an embodiment of Formula (I), Z is O and W is $OCH_2$. In another embodiment, the modified intersubunit linkage of Formula (I) is a modified intersubunit linkage of Formula VI:

(VI)

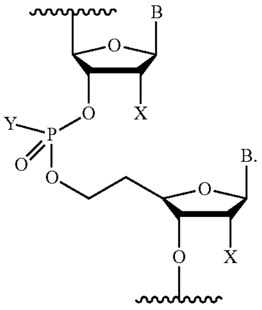

In an embodiment of Formula (I), Z is $CH_2$ and W is CH. In another embodiment, the modified intersubunit linkage of Formula (I) is a modified intersubunit linkage of Formula VII:

(VII)

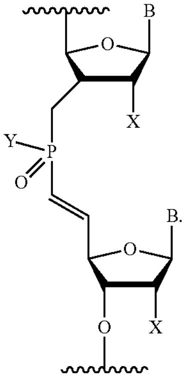

In an embodiment of Formula (I), the base pairing moiety B is selected from the group consisting of adenine, guanine, cytosine, and uracil.

In an embodiment, the modified oligonucleotide is incorporated into siRNA, said modified siRNA having a 5' end, a 3' end, that is complementary to a target, wherein the siRNA comprises a sense and antisense strand, and at least one modified intersubunit linkage of any one or more of Formula (I), Formula (II), Formula (III), Formula (IV), Formula (V), Formula (VI), or Formula (VII).

In an embodiment, the modified oligonucleotide is incorporated into siRNA, said modified siRNA having a 5' end, a 3' end, that is complementary to a target and comprises a sense and antisense strand, wherein the siRNA comprises at least one modified intersubunit linkage is of Formula VIII:

(VIII)

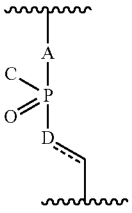

;

wherein:

D is selected from the group consisting of O, $OCH_2$, OCH, CH2, and CH;

C is selected from the group consisting of $O^-$, OH, $OR^1$, $NH^-$, $NH_2$, $S^-$, and SH;

A is selected from the group consisting of O and $CH_2$;

$R^1$ is a protecting group;

is an optional double bond; and the intersubunit is bridging two optionally modified nucleosides.

In an embodiment, when C is $O^-$, either A or D is not O.

In an embodiment, D is $CH_2$. In another embodiment, the modified intersubunit linkage of Formula VIII is a modified intersubunit linkage of Formula (IX):

(IX)

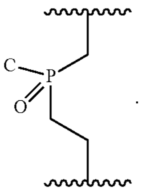

.

In an embodiment, D is O. In another embodiment, the modified intersubunit linkage of Formula VIII is a modified intersubunit linkage of Formula (X):

(X)

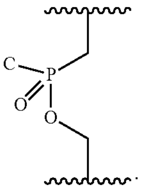

In an embodiment, D is $CH_2$. In another embodiment, the modified intersubunit linkage of Formula (VIII) is a modified intersubunit linkage of Formula (XI):

(XI)

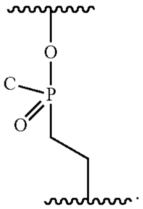

In an embodiment, D is CH. In another embodiment, the modified intersubunit linkage of Formula VIII is a modified intersubunit linkage of Formula (XII):

(XII)

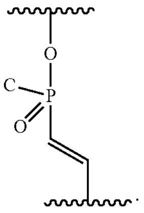

In another embodiment, the modified intersubunit linkage of Formula (VII) is a modified intersubunit linkage of Formula (XIV):

(XIV)

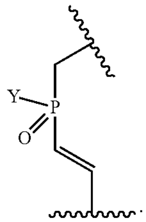

In an embodiment, D is $OCH_2$. In another embodiment, the modified intersubunit linkage of Formula (VII) is a modified intersubunit linkage of Formula (XIII):

(XIII)

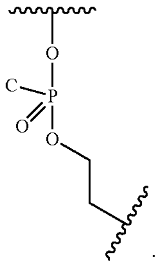

In another embodiment, the modified intersubunit linkage of Formula (VII) is a modified intersubunit linkage of Formula (XXa):

(XXa)

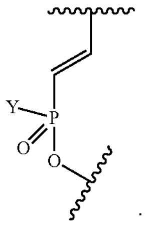

In an embodiment of the modified siRNA linkage, each optionally modified nucleoside is independently, at each occurrence, selected from the group consisting of adenosine, guanosine, cytidine, and uridine.

In certain exemplary embodiments of Formula (I), W is O. In another embodiment, W is $CH_2$. In yet another embodiment, W is CH.

In certain exemplary embodiments of Formula (I), X is OH. In another embodiment, X is $OCH_3$. In yet another embodiment, X is halo.

In a certain embodiment of Formula (I), the modified siRNA does not comprise a 2'-fluoro substituent.

In an embodiment of Formula (I), Y is $O^-$. In another embodiment, Y is OH. In yet another embodiment, Y is OR. In still another embodiment, Y is $NH^-$. In an embodiment, Y is $NH_2$. In another embodiment, Y is $S^-$. In yet another embodiment, Y is SH.

In an embodiment of Formula (I), Z is O. In another embodiment, Z is $CH_2$.

In an embodiment, the modified intersubunit linkage is inserted on position 1-2 of the antisense strand. In another embodiment, the modified intersubunit linkage is inserted on position 6-7 of the antisense strand. In yet another embodiment, the modified intersubunit linkage is inserted on position 10-11 of the antisense strand. In still another embodiment, the modified intersubunit linkage is inserted on position 19-20 of the antisense strand. In an embodiment, the modified intersubunit linkage is inserted on positions 5-6 and 18-19 of the antisense strand.

In an exemplary embodiment of the modified siRNA linkage of Formula (VIII), C is $O^-$. In another embodiment, C is OH. In yet another embodiment, C is $OR^1$. In still another embodiment, C is $NH^-$. In an embodiment, C is $NH_2$. In another embodiment, C is $S^-$. In yet another embodiment, C is SH.

In an exemplary embodiment of the modified siRNA linkage of Formula (VIII), A is O. In another embodiment, A is $CH_2$. In yet another embodiment, C is $OR^1$. In still another embodiment, C is $NH^-$. In an embodiment, C is $NH_2$. In another embodiment, C is $S^-$. In yet another embodiment, C is SH.

In a certain embodiment of the modified siRNA linkage of Formula (VIII), the optionally modified nucleoside is adenosine. In another embodiment of the modified siRNA linkage of Formula (VIII), the optionally modified nucleoside is guanosine. In another embodiment of the modified siRNA linkage of Formula (VIII), the optionally modified nucleoside is cytidine. In another embodiment of the modified siRNA linkage of Formula (VIII), the optionally modified nucleoside is uridine.

In an embodiment of the modified siRNA linkage, wherein the linkage is inserted on position 1-2 of the antisense strand. In another embodiment, the linkage is inserted on position 6-7 of the antisense strand. In yet another embodiment, the linkage is inserted on position 10-11 of the antisense strand. In still another embodiment, the linkage is inserted on position 19-20 of the antisense strand. In an embodiment, the linkage is inserted on positions 5-6 and 18-19 of the antisense strand.

In certain embodiments of Formula (I), the base pairing moiety B is adenine. In certain embodiments of Formula (I), the base pairing moiety B is guanine. In certain embodiments of Formula (I), the base pairing moiety B is cytosine. In certain embodiments of Formula (I), the base pairing moiety B is uracil.

In an embodiment of Formula (I), W is O. In an embodiment of Formula (I), W is $CH_2$. In an embodiment of Formula (I), W is CH.

In an embodiment of Formula (I), X is OH. In an embodiment of Formula (I), X is $OCH_3$. In an embodiment of Formula (I), X is halo.

In an exemplary embodiment of Formula (I), the modified oligonucleotide does not comprise a 2'-fluoro substituent.

In an embodiment of Formula (I), Y is $O^-$. In an embodiment of Formula (I), Y is OH. In an embodiment of Formula (I), Y is OR. In an embodiment of Formula (I), Y is $NH^-$. In an embodiment of Formula (I), Y is $NH_2$. In an embodiment of Formula (I), Y is $S^-$. In an embodiment of Formula (I), Y is SH.

In an embodiment of Formula (I), Z is O. In an embodiment of Formula (I), Z is $CH_2$.

In an embodiment of the Formula (I), the linkage is inserted on position 1-2 of the antisense strand. In another embodiment of Formula (I), the linkage is inserted on position 6-7 of the antisense strand. In yet another embodiment of Formula (I), the linkage is inserted on position 10-11 of the antisense strand. In still another embodiment of Formula (I), the linkage is inserted on position 19-20 of the antisense strand. In an embodiment of Formula (I), the linkage is inserted on positions 5-6 and 18-19 of the antisense strand.

Modified intersubunit linkages are further described in U.S. Ser. No. 62/824,136 (filed Mar. 26, 2019), U.S. Ser. No. 62/826,454 (filed Mar. 29, 2019), and U.S. Ser. No. 62/864,792 (filed Jun. 21, 2019), each of which is incorporated herein by reference.

4) Conjugated Functional Moieties

In other embodiments, RNA silencing agents may be modified with one or more functional moieties. A functional moiety is a molecule that confers one or more additional activities to the RNA silencing agent. In certain embodiments, the functional moieties enhance cellular uptake by target cells (e.g., neuronal cells). Thus, the invention includes RNA silencing agents which are conjugated or unconjugated (e.g., at its 5' and/or 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a certain embodiment, the functional moiety is a hydrophobic moiety. In a certain embodiment, the hydrophobic moiety is selected from the group consisting of fatty acids, steroids, secosteroids, lipids, gangliosides and nucleoside analogs, endocannabinoids, and vitamins. In a certain embodiment, the steroid selected from the group consisting of cholesterol and Lithocholic acid (LCA). In a certain embodiment, the fatty acid selected from the group consisting of Eicosapentaenoic acid (EPA), Docosahexaenoic acid (DHA) and Docosanoic acid (DCA). In a certain embodiment, the vitamin selected from the group consisting of choline, vitamin A, vitamin E, and derivatives or metabolites thereof. In a certain embodiment, the vitamin is selected from the group consisting of retinoic acid and alpha-tocopheryl succinate.

In a certain embodiment, an RNA silencing agent of invention is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, a a cationic dye (e.g., Cy3). In an exemplary embodiment, the lipophilic moiety is cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine.

In certain embodiments, the functional moieties may comprise one or more ligands tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These can be located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or a metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine, has an increased affinity for the HIV Rev-response element (RRE). In some embodiments, the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, either directly or indirectly, via an intervening tether, to a ligand-conjugated carrier. In certain embodiments, the coupling is through a covalent bond. In certain embodiments, the ligand is attached to the carrier via an intervening tether. In certain embodiments, a ligand alters the distribution, targeting or lifetime of an RNA silencing agent into which it is incorporated. In certain embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine (GalNAc) or derivatives thereof, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl) glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, $Eu^{3+}$ complexes of tetraazamacrocycles), dinitrophenyl, HRP or AP. In certain embodiments, the ligand is GalNAc or a derivative thereof.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-kB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNF□), interleukin-1 beta, or gamma interferon. In one aspect, the ligand is a lipid or lipid-based molecule. Such a lipid or lipid-based molecule can bind a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a certain embodiment, the lipid based ligand binds HSA. A lipid-based ligand can bind HSA with a sufficient affinity such that the conjugate will be distributed to a non-kidney tissue. However, it is contemplated that the affinity not be so strong that the HSA-ligand binding cannot be reversed. In another embodiment, the lipid based ligand binds HSA weakly or not at all, such that the conjugate will be distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These can be useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, such as a helical cell-permeation agent. In certain embodiments, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent can be an alpha-helical agent, which may have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

In certain embodiments, the functional moiety is linked to the 5' end and/or 3' end of the RNA silencing agent of the disclosure. In certain embodiments, the functional moiety is linked to the 5' end and/or 3' end of an antisense strand of the RNA silencing agent of the disclosure. In certain embodiments, the functional moiety is linked to the 5' end and/or 3' end of a sense strand of the RNA silencing agent of the disclosure. In certain embodiments, the functional moiety is linked to the 3' end of a sense strand of the RNA silencing agent of the disclosure.

In certain embodiments, the functional moiety is linked to the RNA silencing agent by a linker. In certain embodiments, the functional moiety is linked to the antisense strand and/or sense strand by a linker. In certain embodiments, the functional moiety is linked to the 3' end of a sense strand by a linker. In certain embodiments, the linker comprises a divalent or trivalent linker. In certain embodiments, the linker comprises an ethylene glycol chain, an alkyl chain, a peptide, RNA, DNA, a phosphodiester, a phosphorothioate, a phosphoramidate, an amide, a carbamate, or a combination thereof. In certain embodiments, the divalent or trivalent linker is selected from:

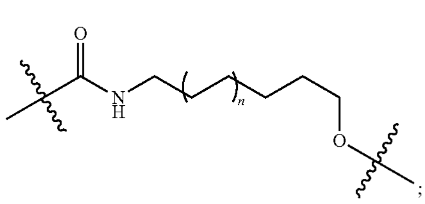

;

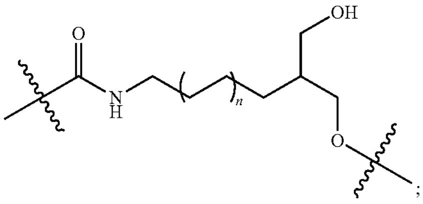

;

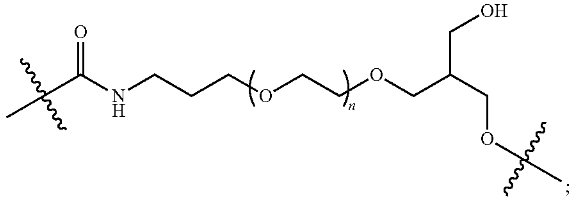

;

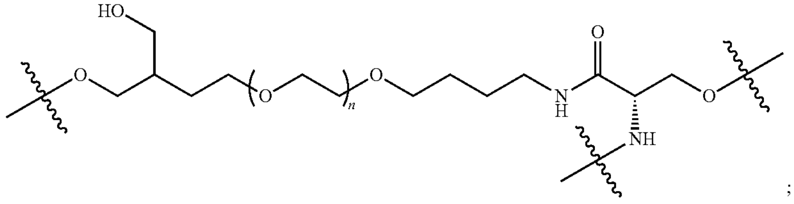

; or

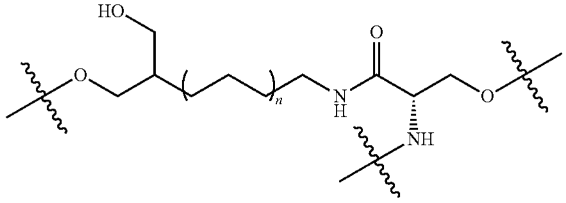

wherein n is 1, 2, 3, 4, or 5.

In certain embodiments, the linker further comprises a phosphodiester or phosphodiester derivative. In certain embodiments, the phosphodiester or phosphodiester derivative is selected from the group consisting of:

(Zc1)

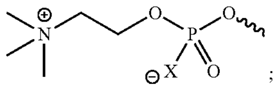

;

(Zc2)

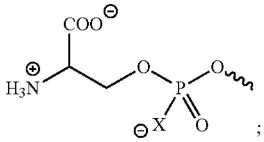

;

(Zc3)

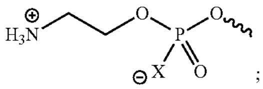

; and (Zc4)

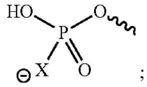

;

wherein X is O, S or $BH_3$.

The various functional moieties of the disclosure and means to conjugate them to RNA silencing agents are described in further detail in WO2017/030973A1 and WO2018/031933A2, incorporated herein by reference.

VI. Branched Oligonucleotides

Two or more RNA silencing agents as disclosed supra, for example oligonucleotide constructs such as anti-PRNP siRNAs, may be connected to one another by one or more moieties independently selected from a linker, a spacer and a branching point, to form a branched oligonucleotide RNA silencing agent. In certain embodiments, the branched oligonucleotide RNA silencing agent consists of two siRNAs to form a di-branched siRNA ("di-siRNA") scaffolding for delivering two siRNAs. In representative embodiments, the nucleic acids of the branched oligonucleotide each comprise an antisense strand (or portions thereof), wherein the antisense strand has sufficient complementarity to a target mRNA (e.g., PRNP mRNA) to mediate an RNA-mediated silencing mechanism (e.g. RNAi).

In exemplary embodiments, the branched oligonucleotides may have two to eight RNA silencing agents attached through a linker. The linker may be hydrophobic. In an embodiment, branched oligonucleotides of the present application have two to three oligonucleotides. In an embodiment, the oligonucleotides independently have substantial chemical stabilization (e.g., at least 40% of the constituent bases are chemically-modified). In an exemplary embodiment, the oligonucleotides have full chemical stabilization (i.e., all the constituent bases are chemically-modified). In some embodiments, branched oligonucleotides comprise one or more single-stranded phosphorothioated tails, each independently having two to twenty nucleotides. In a non-limiting embodiment, each single-stranded tail has two to ten nucleotides.

In certain embodiments, branched oligonucleotides are characterized by three properties: (1) a branched structure, (2) full metabolic stabilization, and (3) the presence of a single-stranded tail comprising phosphorothioate linkers. In certain embodiments, branched oligonucleotides have 2 or 3 branches. It is believed that the increased overall size of the branched structures promotes increased uptake. Also, without being bound by a particular theory of activity, multiple adjacent branches (e.g., 2 or 3) are believed to allow each branch to act cooperatively and thus dramatically enhance rates of internalization, trafficking and release.

Branched oligonucleotides are provided in various structurally diverse embodiments. In some embodiments nucleic acids attached at the branching points are single stranded or double stranded and consist of miRNA inhibitors, gapmers, mixmers, SSOs, PMOs, or PNAs. These single strands can be attached at their 3' or 5' end. Combinations of siRNA and single stranded oligonucleotides could also be used for dual function. In another embodiment, short nucleic acids complementary to the gapmers, mixmers, miRNA inhibitors, SSOs, PMOs, and PNAs are used to carry these active single-stranded nucleic acids and enhance distribution and cellular internalization. The short duplex region has a low melting temperature (Tm ~37 °C.) for fast dissociation upon internalization of the branched structure into the cell.

The Di-siRNA branched oligonucleotides may comprise chemically diverse conjugates, such as the functional moieties described above. Conjugated bioactive ligands may be used to enhance cellular specificity and to promote membrane association, internalization, and serum protein binding. Examples of bioactive moieties to be used for conjugation include DHA, GalNAc, and cholesterol. These moieties can be attached to Di-siRNA either through the connecting linker or spacer, or added via an additional linker or spacer attached to another free siRNA end.

The presence of a branched structure improves the level of tissue retention in the brain more than 100-fold compared to non-branched compounds of identical chemical composition, suggesting a new mechanism of cellular retention and distribution. Branched oligonucleotides have unexpectedly uniform distribution throughout the spinal cord and brain. Moreover, branched oligonucleotides exhibit unexpectedly efficient systemic delivery to a variety of tissues, and very high levels of tissue accumulation.

Branched oligonucleotides comprise a variety of therapeutic nucleic acids, including siRNAs, ASOs, miRNAs, miRNA inhibitors, splice switching, PMOs, PNAs. In some embodiments, branched oligonucleotides further comprise conjugated hydrophobic moieties and exhibit unprecedented silencing and efficacy in vitro and in vivo.

Linkers

In an embodiment of the branched oligonucleotide, each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment, each linker is an ethylene glycol chain. In another embodiment, each linker is an alkyl chain. In another embodiment, each linker is a peptide. In another embodiment, each linker is RNA. In another embodiment, each linker is DNA. In another embodiment, each linker is a phosphate. In another embodiment, each linker is a phosphonate. In another embodiment, each linker is a phosphoramidate. In another embodiment, each linker is an ester. In another embodiment, each linker is an amide. In another embodiment, each linker is a triazole.

In an embodiment of the branched oligonucleotide, the linker has the structure of L1:

(L1)

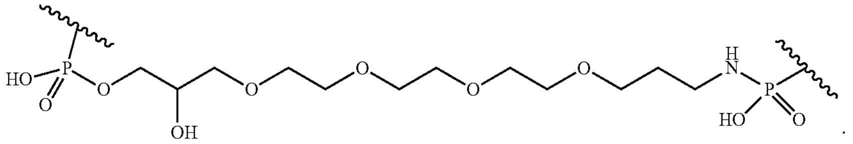

In an embodiment of the branched oligonucleotide, the linker has the structure of L2:

(L2)

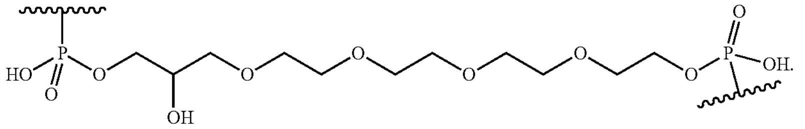

It is to be understood that the methods described in this disclosure are not limited to particular methods and experimental conditions disclosed herein; as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2nd edition).

Branched oligonucleotides, including synthesis and methods of use, are described in greater detail in WO2017/132669, incorporated herein by reference.

Methods of Introducing Nucleic Acids, Vectors and Host Cells

RNA silencing agents of the invention may be directly introduced into the cell (e.g., a neural cell) (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA silencing agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target gene.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus, the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, Enzyme Linked ImmunoSorbent Assay (ELISA), Western blotting, RadioImmunoAssay (RIA), other immunoassays, and Fluorescence Activated Cell Sorting (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of RNAi agent may result in inhibition in a smaller fraction of cells (e.g., at least 10%, 20%, 50%, 75%, 90%, or 95% of targeted cells). Quantization of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In an exemplary aspect, the efficacy of an RNAi agent of the invention (e.g., an siRNA targeting an PRNP target sequence) is tested for its ability to specifically degrade mutant mRNA (e.g., PRNP mRNA and/or the production of PRNP protein) in cells, such as cells in the central nervous system. In certain embodiments, cells in the central nervous system include, but are not limited to, neurons (e.g., striatal or cortical neuronal clonal lines and/or primary neurons), glial cells, and astrocytes. Also suitable for cell-based validation assays are other readily transfectable cells, for example, HeLa cells or COS cells. Cells are transfected with human wild type or mutant cDNAs (e.g., human wild type or mutant PRNP cDNA). Standard siRNA, modified siRNA or vectors able to produce siRNA from U-looped mRNA are co-transfected. Selective reduction in target mRNA (e.g., PRNP mRNA) and/or target protein (e.g., PRNP protein) is measured. Reduction of target mRNA or protein can be compared to levels of target mRNA or protein in the absence of an RNAi agent or in the presence of an RNAi agent that does not target PRNP mRNA. Exogenously-introduced mRNA or protein (or endogenous mRNA or protein) can be assayed for comparison purposes. When utilizing neuronal cells, which are known to be somewhat resistant to standard transfection techniques, it may be desirable to introduce RNAi agents (e.g., siRNAs) by passive uptake.

VII. Methods of Treatment

In one aspect, the present invention provides for both prophylactic and therapeutic methods of treating a subject at risk of (or susceptible to) a disease or disorder caused, in whole or in part, by trinucleotide repeats. In one embodiment, the disease or disorder is such that PRNP levels in the central nervous system (CNS) have been found to be predictive of neurodegeneration progression. In another embodiment, the disease or disorder is a polyglutamine disorder. In a certain embodiment, the disease or disorder one in which reduction of PRNP in the CNS reduces clinical manifestations seen in neurodegenerative diseases such as Huntington's disease.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a CNS cell expressing PRNP with a therapeutic agent (e.g., a RNAi agent or vector or transgene encoding same) that is specific for a target sequence within the gene, such that sequence specific interference with the gene is achieved. These methods can be performed in vitro (e.g., by culturing the cell with the agent) or, alternatively, in vivo (e.g., by administering the agent to a subject).

With regard to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

A pharmaceutical composition containing an RNA silencing agent of the invention can be administered to any patient diagnosed as having or at risk for developing a neurodegenerative disease. In one embodiment, the patient is diagnosed as having a neurological disorder, and the patient is otherwise in general good health. For example, the patient is not terminally ill, and the patient is likely to live at least 2, 3, 5 or more years following diagnosis. The patient can be treated immediately following diagnosis, or treatment can be delayed until the patient is experiencing more debilitating symptoms, such as motor fluctuations and dyskinesis in Parkinson's disease patients. In another embodiment, the patient has not reached an advanced stage of the disease.

In embodiments of this aspect, the prophylactic and therapeutic methods are directed to treating or managing neurodegenerative diseases or disorders in which reduction of PRNP in the CNS reduces abnormal amyloid accumulation. In a non-limiting example, the RNA silencing agent is a branched oligonucleotide as described in sections VI and VII herein, which is administered to a patient diagnosed as having or at risk for developing Huntington's disease or an amyloid-related neurodegenerative disease or disorder such as Alzheimer's disease, cerebral amyloid angiopathy, or mild-to-moderate cognitive impairment. The patient can be treated following diagnosis, at varying stage of the disease, or as a prophylactic measure in instances where genetic traits, family history, or other factors put the patient at risk for the neurodegenerative disease or disorder. Successful dosage amounts and schedules may be established and monitored by metrics indicative of effective treatment, for example the extent of inhibition, delay, prevention or reduction of symptoms such as cognitive decline, beta-amyloid plaque formation in the brain, and neurodegeneration which are detected following the initiation of treatment.

VIII. Pharmaceutical Compositions and Methods of Administration

The invention pertains to uses of the above-described agents for prophylactic and/or therapeutic treatments as described infra. Accordingly, the modulators (e.g., RNAi agents) of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. In certain exemplary embodiments, a pharmaceutical composition of the invention is delivered to the cerebrospinal fluid (CSF) by a route of administration that includes, but is not limited to, intrastriatal (IS) administration, intracerebroventricular (ICV) administration and intrathecal (IT) administration (e.g., via a pump, an infusion or the like). Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

The RNA silencing agents can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

In certain embodiments, a composition that includes an RNA silencing agent of the invention can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection. One route of delivery is directly to the brain, e.g., into the ventricles or the hypothalamus of the brain, or into the lateral or dorsal areas of the brain. The RNA silencing agents for neural cell delivery can be incorporated into pharmaceutical compositions suitable for administration.

For example, compositions can include one or more species of an RNA silencing agent and a pharmaceutically acceptable carrier. The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration. In certain exemplary embodiments, an RNA silencing agent of the invention is delivered across the Blood-Brain-Barrier (BBB) suing a variety of suitable compositions and methods described herein.

The route of delivery can be dependent on the disorder of the patient. For example, a subject diagnosed with a neurodegenerative disease can be administered an anti-PRNP RNA silencing agent of the invention directly into the brain (e.g., into the globus pallidus or the corpus striatum of the basal ganglia, and near the medium spiny neurons of the corpus striatum). In addition to an RNA silencing agent of the invention, a patient can be administered a second therapy, e.g., a palliative therapy and/or disease-specific therapy. The secondary therapy can be, for example, symptomatic (e.g., for alleviating symptoms), neuroprotective (e.g., for slowing or halting disease progression), or restorative (e.g., for reversing the disease process). Other therapies can include psychotherapy, physiotherapy, speech therapy, communicative and memory aids, social support services, and dietary advice.

An RNA silencing agent can be delivered to neural cells of the brain. Delivery methods that do not require passage of the composition across the blood-brain barrier can be utilized. For example, a pharmaceutical composition containing an RNA silencing agent can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The RNA silencing agent can be delivered into multiple regions of the central nervous system (e.g., into multiple regions of the brain, and/or into the spinal cord). The RNA silencing agent can be delivered into diffuse regions of the brain (e.g., diffuse delivery to the cortex of the brain).

In one embodiment, the RNA silencing agent can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of RNA silencing agent. The flow or delivery can be mediated by a pump, e.g., an osmotic pump or minipump, such as an Alzet pump (Durect, Cupertino, CA). In one embodiment, a pump and reservoir are implanted in an area distant from the tissue, e.g., in the abdomen, and delivery is effected by a conduit leading from the pump or reservoir to the site of release. Devices for delivery to the brain are described, for example, in U.S. Pat. Nos. 6,093,180, and 5,814,014.

An RNA silencing agent of the invention can be further modified such that it is capable of traversing the blood brain barrier. For example, the RNA silencing agent can be conjugated to a molecule that enables the agent to traverse the barrier. Such modified RNA silencing agents can be administered by any desired method, such as by intraventricular or intramuscular injection, or by pulmonary delivery, for example.

In certain embodiments, exosomes are used to deliver an RNA silencing agent of the invention. Exosomes can cross the BBB and deliver siRNAs, antisense oligonucleotides, chemotherapeutic agents and proteins specifically to neurons after systemic injection (See, Alvarez-Erviti L, Seow Y, Yin H, Betts C, Lakhal S, Wood M J. (2011). Delivery of siRNA to the mouse brain by systemic injection of targeted exosomes. Nat Biotechnol. 2011 April; 29(4):341-5. doi: 10.1038/nbt.1807; El-Andaloussi S, Lee Y, Lakhal-Littleton S, Li J, Scow Y, Gardiner C, Alvarez-Erviti L, Sargent I L, Wood M J. (2011). Exosome-mediated delivery of siRNA in vitro and in vivo. Nat Protoc. 2012 December; 7(12):2112-26. doi: 10.1038/nprot.2012.131; EL Andaloussi S, Mäger I, Breakefield X O, Wood M J. (2013). Extracellular vesicles: biology and emerging therapeutic opportunities. Nat Rev Drug Discov. 2013 May; 12(5):347-57. doi: 10.1038/nrd3978; El Andaloussi S, Lakhal S, Mäger I, Wood M J. (2013). Exosomes for targeted siRNA delivery across biological barriers. Adv Drug Deliv Rev. 2013 March; 65(3): 391-7. doi: 10.1016/j.addr.2012.08.008).

In certain embodiments, one or more lipophilic molecules are used to allow delivery of an RNA silencing agent of the invention past the BBB (Alvarez-Ervit (2011)). The RNA silencing agent would then be activated, e.g., by enzyme degradation of the lipophilic disguise to release the drug into its active form.

In certain embodiments, one or more receptor-mediated permeabilizing compounds can be used to increase the permeability of the BBB to allow delivery of an RNA silencing agent of the invention. These drugs increase the permeability of the BBB temporarily by increasing the osmotic pressure in the blood which loosens the tight junctions between the endothelial cells ((El-Andaloussi (2012)). By loosening the tight junctions normal intravenous injection of an RNA silencing agent can be performed.

In certain embodiments, nanoparticle-based delivery systems are used to deliver an RNA silencing agent of the invention across the BBB. As used herein, "nanoparticles" refer to polymeric nanoparticles that are typically solid, biodegradable, colloidal systems that have been widely investigated as drug or gene carriers (S. P. Egusquiaguirre, M. Igartua, R. M. Hernandez, and J. L. Pedraz, "Nanoparticle delivery systems for cancer therapy: advances in clinical and preclinical research," Clinical and Translational Oncology, vol. 14, no. 2, pp. 83-93, 2012). Polymeric nanoparticles are classified into two major categories, natural polymers and synthetic polymers. Natural polymers for siRNA delivery include, but are not limited to, cyclodextrin, chitosan, and atelocollagen (Y. Wang, Z. Li, Y. Han, L. H. Liang, and A. Ji, "Nanoparticle-based delivery system for application of siRNA in vivo," Current Drug Metabolism, vol. 11, no. 2, pp. 182-196, 2010). Synthetic polymers include, but are not limited to, polyethyleneimine (PEI), poly(dl-lactide-co-glycolide) (PLGA), and dendrimers, which have been intensively investigated (X. Yuan, S. Naguib, and Z. Wu, "Recent advances of siRNA delivery by nanoparticles," Expert Opinion on Drug Delivery, vol. 8, no. 4, pp. 521-536, 2011). For a review of nanoparticles and other suitable delivery systems, See Jong-Min Lee, Tac-Jong Yoon, and Young-Seok Cho, "Recent Developments in Nanoparticle-Based siRNA Delivery for Cancer Therapy," BioMed Research International, vol. 2013, Article ID 782041, 10 pages, 2013. doi: 10.1155/2013/782041 (incorporated by reference in its entirety.)

Compositions for intrathecal or intraventricular (e.g., intracerebroventricular) administration may include sterile aqueous solutions which may also contain buffers, diluents and other suitable additives. In certain embodiments, compositions for intrathecal or intraventricular administration do not include a transfection reagent or an additional lipophilic moiety besides, for example, the lipophilic moiety attached to the RNA silencing agent.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following example, which is included for purposes of illustration only and is not intended to be limiting.

EXAMPLES

Example 1. Divalent siRNA-Mediated Lowering of PrP

Figure 1B:
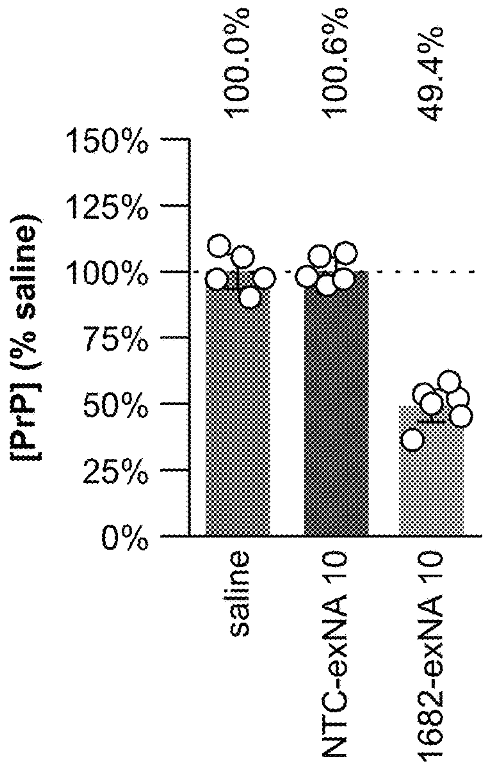

To identify tool compounds for initial studies, a small-scale screen in mouse N2a cells of 20 siRNA sequences targeting mouse Prnp was performed (FIG. 1A). This identified oligo 1682 as promising, with 11.7% residual Prnp mRNA. The oligonucleotide synthesized in divalent format in an exNA internucleotide modification scaffold (see FIG. 5), and the potency was compared versus saline or a non-targeting control compound after a single ICV dose in wild-type C57BL/6N mice (FIG. 1B). For clarity, note that all mouse doses described throughout this Example are in moles of divalent siRNA compound (1 mol di-siRNA=2 mol monovalent siRNA equivalents) and are given as total doses per animal (10 nmol total dose is administered via bilateral ICV, so 5 nmol per side). At 30 days post-dose 1682-exNA at 10 nmol lowered the target by half, leaving 49.4% residual PrP protein in whole brain hemispheres measured by ELISA (Mortberg et al. JCI Insight. 2022. 7(6): e156532). This is similar to the potency of PrP-lowering ASO tool compounds we have tested previously. We advanced this compound into studies in a standard disease model: wild-type mice infected intracerebrally with the RML strain of mouse prions. The Rocky Mountain Laboratory (RML) prion strain is described in further detail in Wenborn et al. 2015. Sci. Rep. 5: 10062.

Divalent siRNA treatment was initiated at different timepoints in two cohorts: 75 days post-inoculation (dpi), corresponding to a pathological disease stage (evinced by elevated neurofilament and astrogliosis), and at 126 dpi, approximately at the onset of symptoms. 75 dpi animals received chronic treatment every 120 days (q120d) while 126 dpi animals received a single dose. At each dosing timepoint, animals received 10 nmol of divalent siRNA (20 nmol monovalent equivalents) split between bilateral doses into CSF via the cerebral ventricle. Control animals received a non-targeting control exNA compound, saline, or no injection.

Figure 1C:
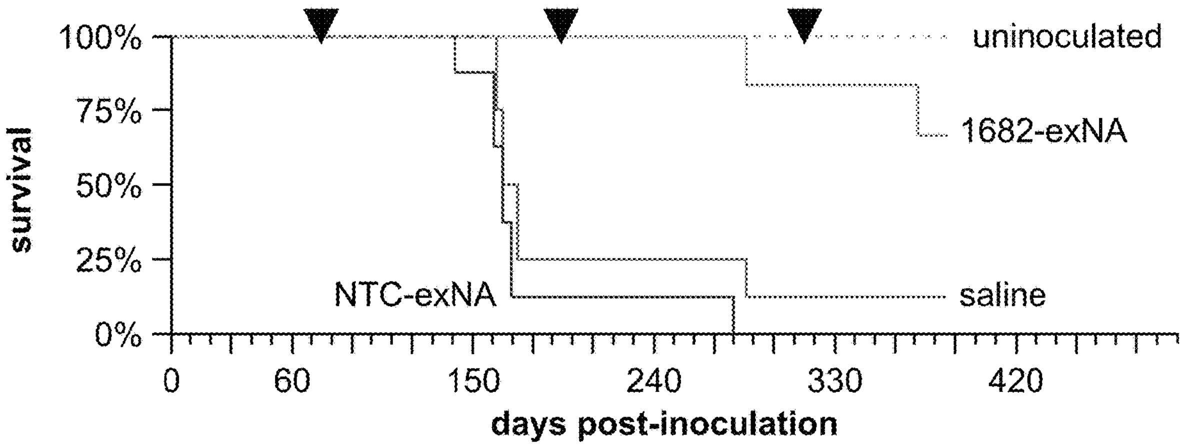
Figure 1D:
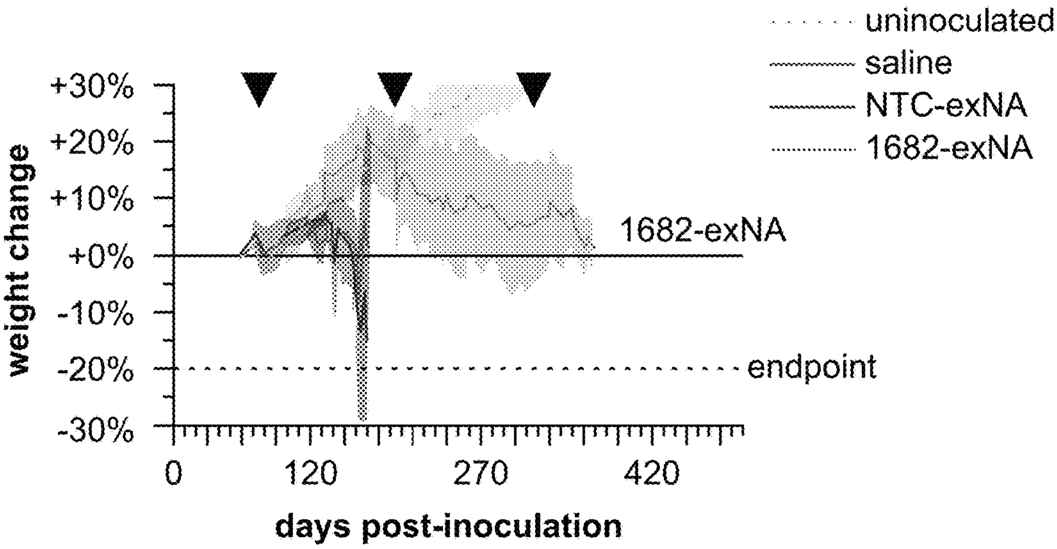
Figure 1E:
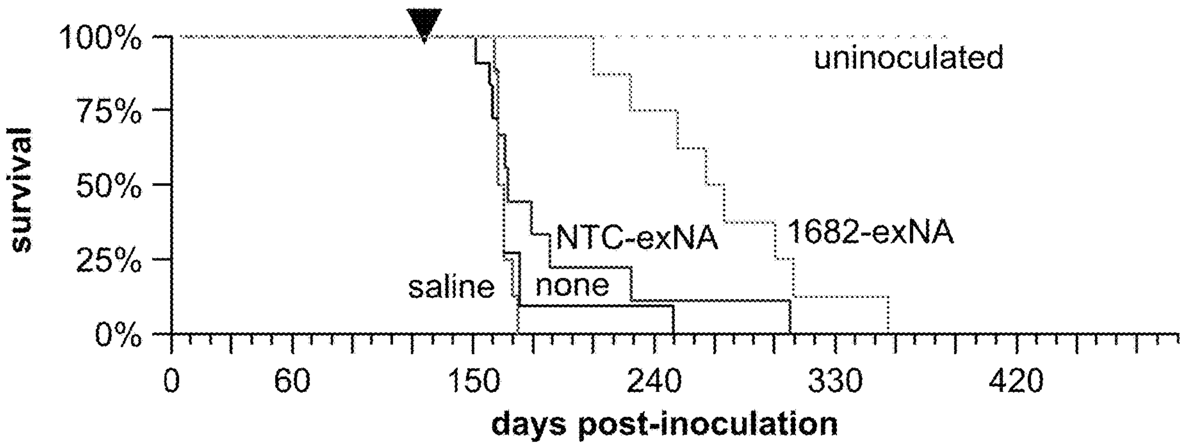
Figure 1F:
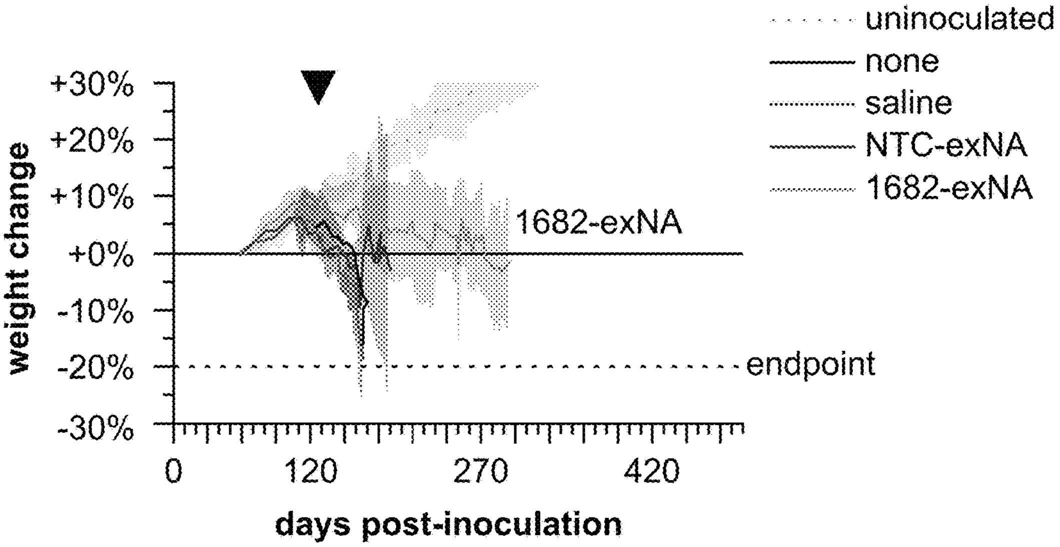

In the ongoing 75 dpi study (FIG. 1C), 1682-exNA animals significantly outlived controls (P=0.0002, log-rank test) and 4/6 animals remain alive as of 372 dpi. As of this writing, remaining animals have lost some weight (FIG. 1D) but remain above baseline. So far, this result is similar to the outcome achieved by chronic ASO administration, where animals chronically treated starting at 78 dpi were likewise losing weight by 250 dpi. That we achieved this outcome with a tool compound of similar potency, despite less frequent dosing (q120d here vs. q90d in the published ASO study) may point to superior durability of di-siRNA. In the 126 dpi single dose cohort, 1682-exNA animals lived 109 days longer than controls (274±47 vs. 165±4 dpi, P=0.0002, log-rank test, FIG. 1E), eventually developing typical prion disease signs and succumbing to weight loss endpoint (FIG. 1F). This amounts to a 67% increase in total survival time, or a 3.8× increase in remaining survival time from the moment of treatment at 126 dpi. Survival time was similar to that of animals that received a single dose of ASO in a published experiment (275±3 dpi) (Minikel et al. Nucleic Acids Res. 2020. 48(19): 10615-10631). In neither cohort of di-siRNA treated animals did we observe premature deaths after dosing, so the treatment appears well tolerated even in prion-infected animals. These results validate di-siRNA as a promising modality for treating prion disease. The benefit of 50% reduction of PrP appears generally similar whether achieved by di-siRNA, ASO, or heterozygous genetic knockout, consistent with our mechanistic understanding of prion disease as strictly dependent upon PrP expression. This confirmed our expectation that for a divalent siRNA to achieve superior therapeutic benefit or superior probability of clinical success in prion disease, compared to an ASO, will depend upon identification of a compound with superior potency, durability, and/or tolerability.

Example 2. A Highly Potent Divalent siRNA-Mediated Lowering of PrP

Figure 2A:
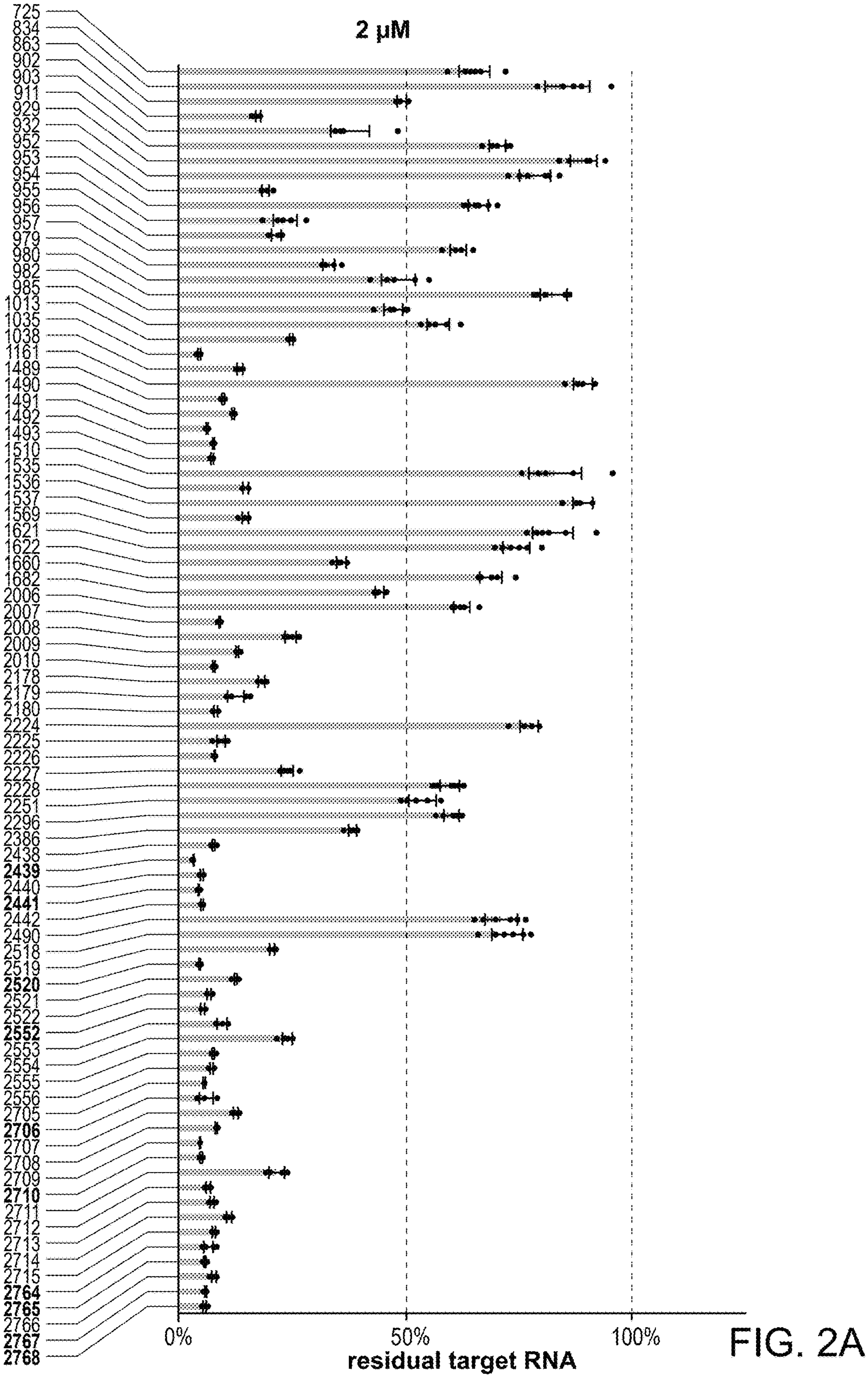
FIG. 2A-FIG. 2D depict the identification of human di-siRNA lead sequence 2439.
Figure 2A:
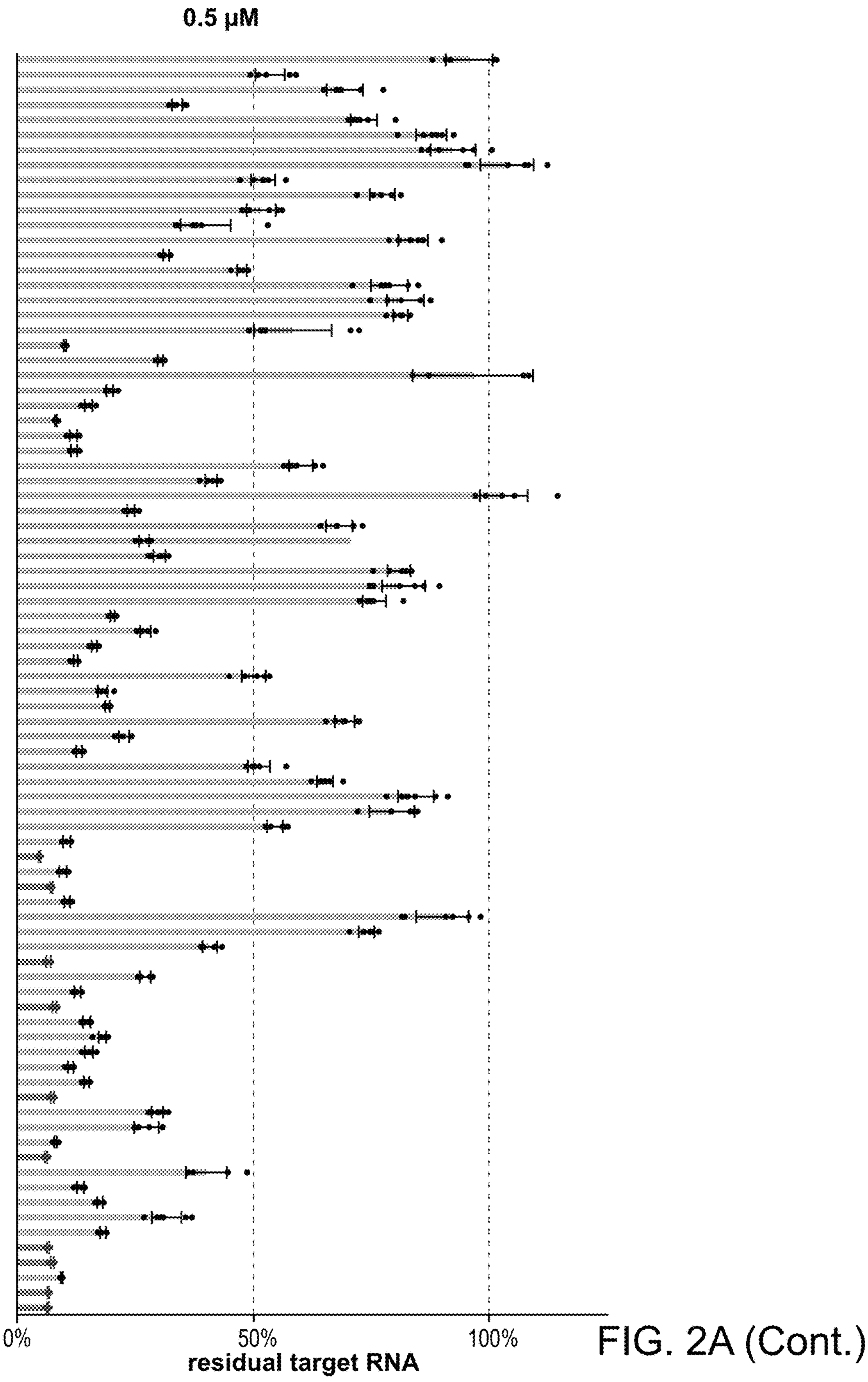
Figure 2B:
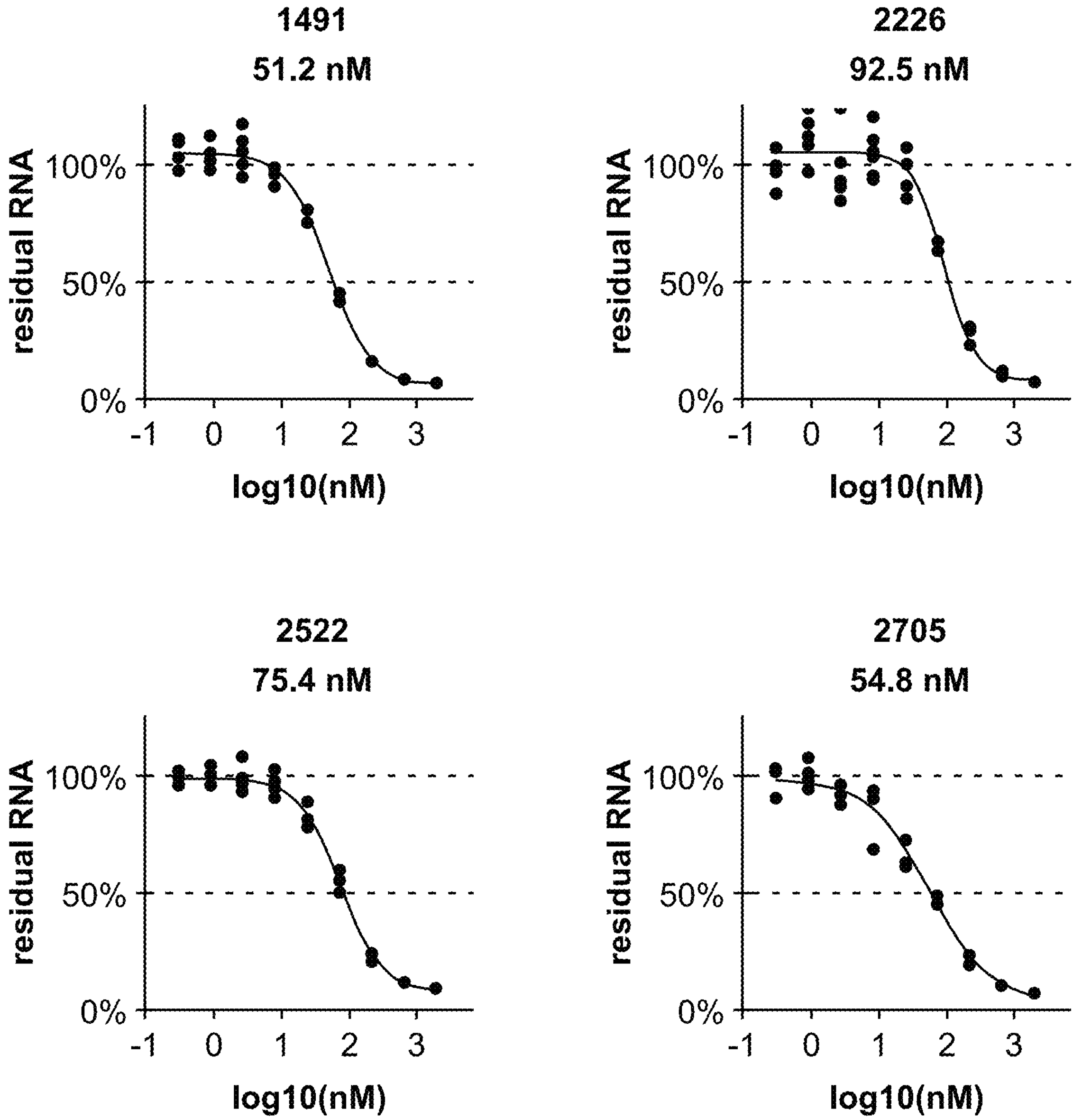
Figure 2C:
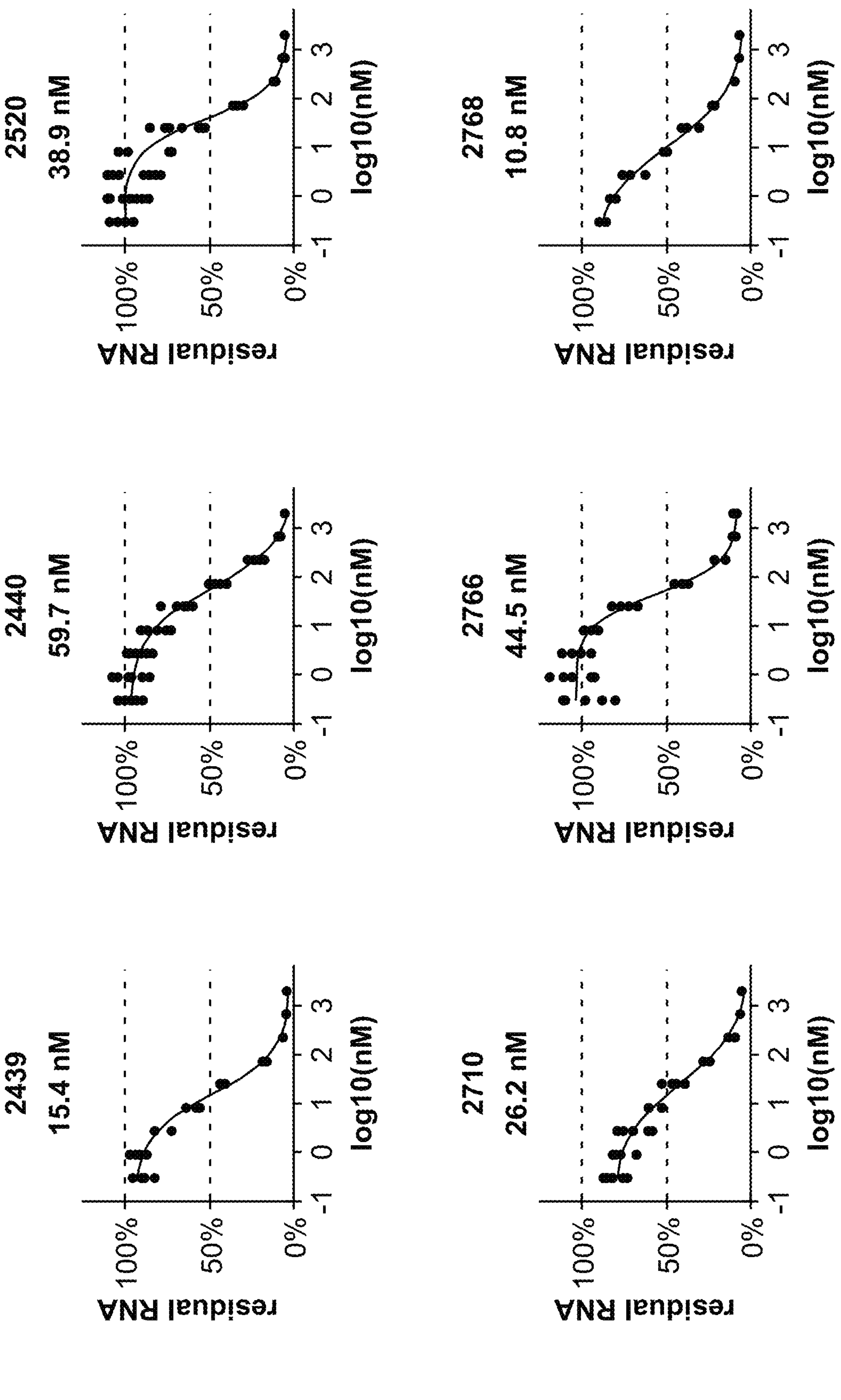

Because our mouse tool compound, above, exhibited similar potency and similar efficacy as a previously reported ASO, we launched a more intensive screen for candidate human PRNP-targeting sequences in order to identify candidates with superior potency. We screened 85 human PRNP-targeting siRNAs in human U251-MG glioblastoma cells. At 2 μM test compound, all tested compounds had at least some potency (>10% knockdown or <90% residual target RNA compared to untreated cells (FIG. 2A), with 34 human compounds resulting in >90% knockdown (<10% residual), a challenge for discrimination of most potent compounds. At 0.5 μM test compound, several human compounds differentiated themselves as most potent, with ten compounds achieving <8% residual (FIG. 2A). 10 hits from the 0.5 μM condition were advanced into in cellulo dose-response to determine IC50 values (FIG. 2B and FIG. 2C), and ultimately 7 sequences were advanced to in vivo potency screening (the most potent compounds plus others prioritized for reasons such as species cross-reactivity).

Figure 2D:
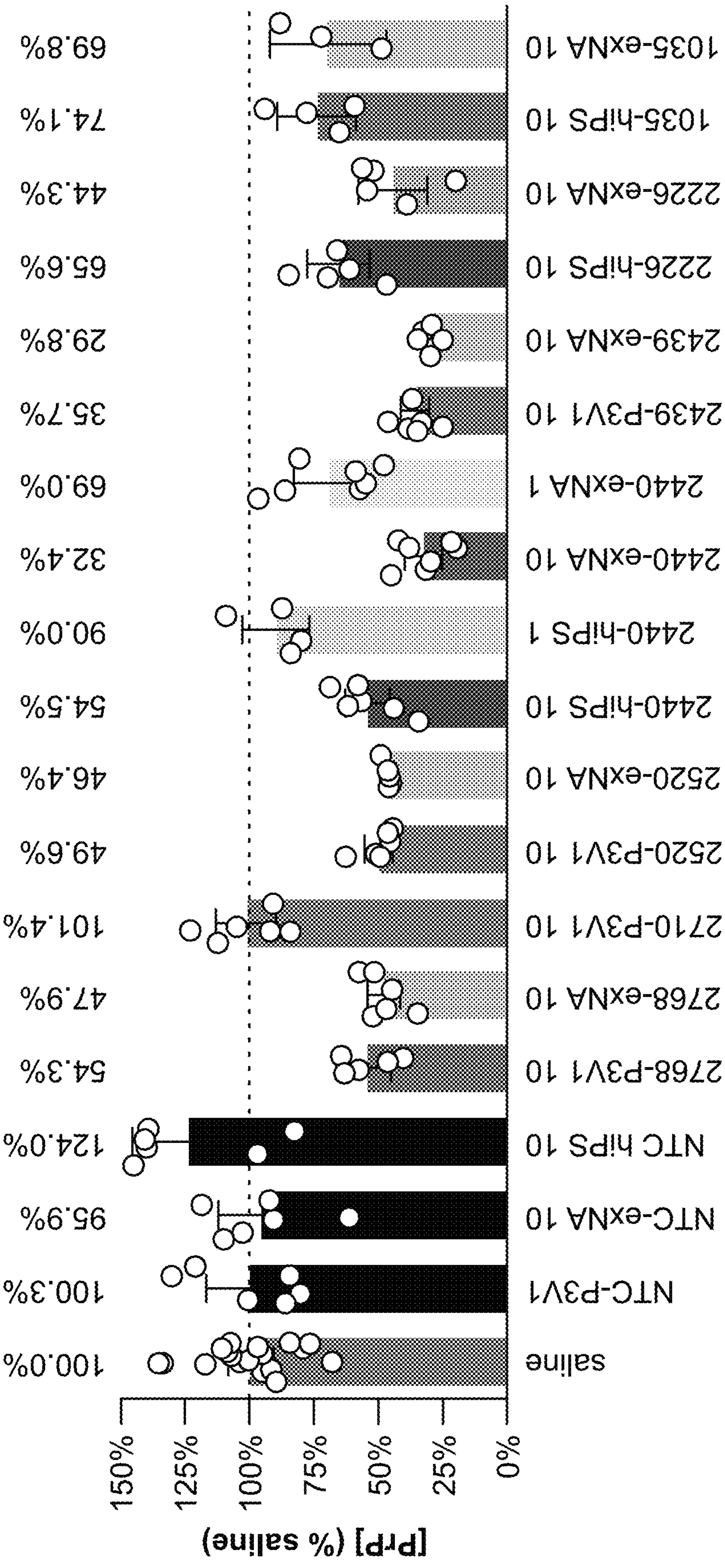

For in vivo potency screening, we tested compounds in either the novel exNA scaffold or in the originally reported high phosphorothioate (hiPS) scaffold (described in Alterman et al. Nat. Biotechnol. 2019. 37(8): 884-894) or a variant thereof (P3V1), along with saline and non-targeting control (NTC) di-siRNAs of each scaffold. Compounds were injected at either 1 or 10 nmol in Tg26372 homozygous mice (FIG. 2D) which possess 20 copies of human PRNP and express ~6-fold human PrP levels, on a background of endogenous PrP knockout. After 30-34 days in-life, animals were sacrificed and whole brain hemispheres homogenized for analysis by a PrP ELISA described in Mortberg et al. JCI Insight. 2022. 7(6): e156532. Compound 2439-exNA emerged as the most potent, with 29.8% residual PrP. Notably, for all 6/6 sequences where both scaffolds were tested, the exNA scaffold provided superior knockdown to the hiPS/P3V1 scaffolds.

Example 3. Screen of Chemical Modification Patterns for Target 2439

Figure 3A:
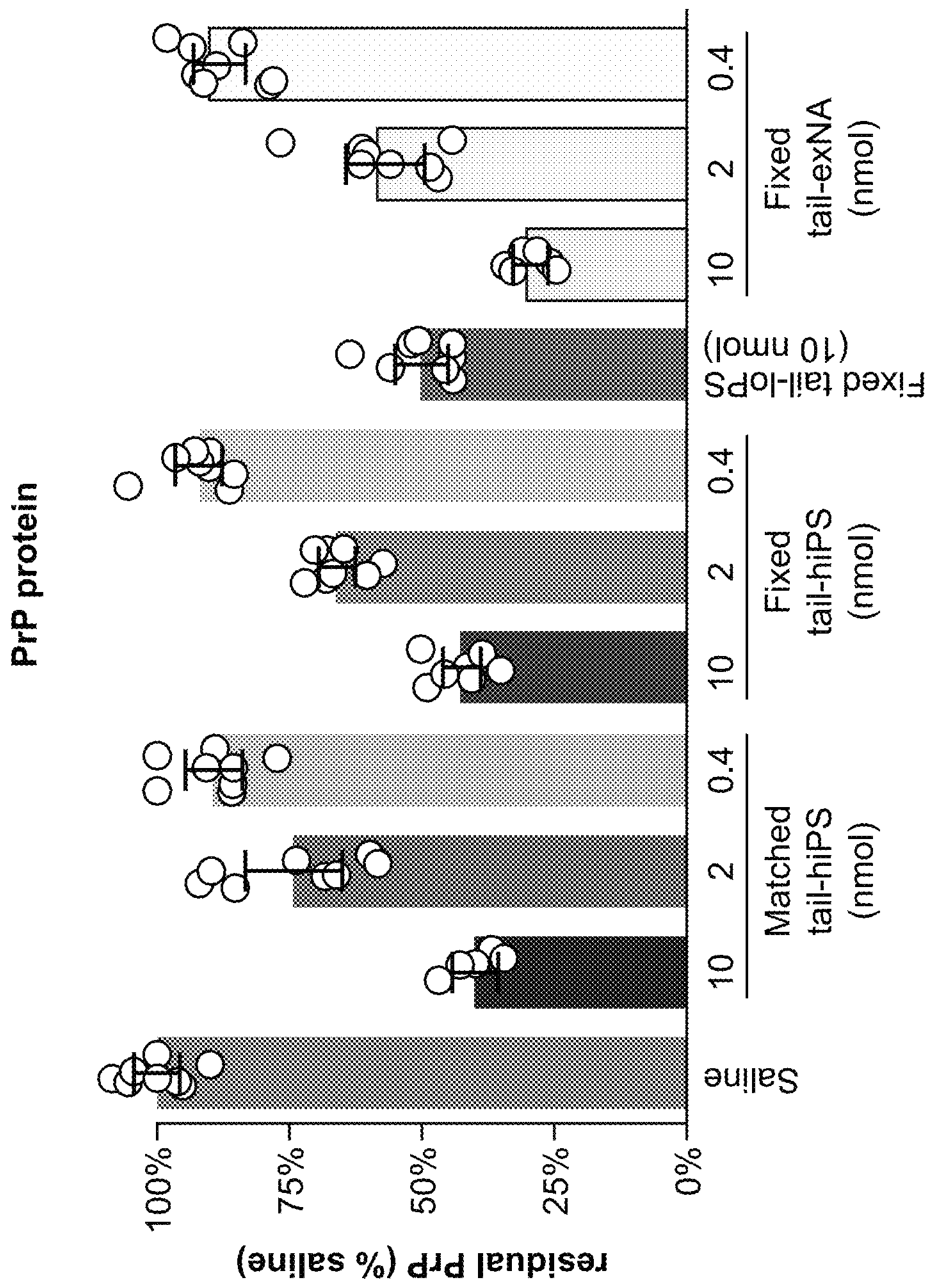
FIG. 3A-FIG. 3D depict screening of chemical modification patterns in human di-siRNA lead sequence 2439. Data for FIG. 3A-FIG. 3D was generated from groups of N=8 Tg26372 humanized mice per cohort receiving any of 11 treatments: saline, 10 nmol fixed tail loPS 2439, or 0.4, 2, or 10 nmol of 2439 with hiPS matched tail, hiPS fixed tail, or exNA fixed tail.

To confirm whether the exNA scaffold was indeed superior, we designed a thorough head-to-head in vivo study using lead sequence 2439. This experiment had the goals of i) confirming whether exNA siRNAs achieve superior knockdown, ii) determining which brain regions drive superiority, and iii) determining whether the exNA nucleotides per se, or the UU "fixed tail", drives the superiority. Groups of N=8 Tg26372 humanized mice per cohort received any of 11 treatments: saline, or sequence 2439 in the form of 10 nmol fixed tail loPS, or 0.4, 2, or 10 nmol of P3V1 matched tail, P3V1 fixed tail, or exNA fixed tail. the 10 nmol dose of the exNA scaffold proved superior on the metric of whole-hemisphere protein level reduction (FIG. 3A).

Figure 3B:
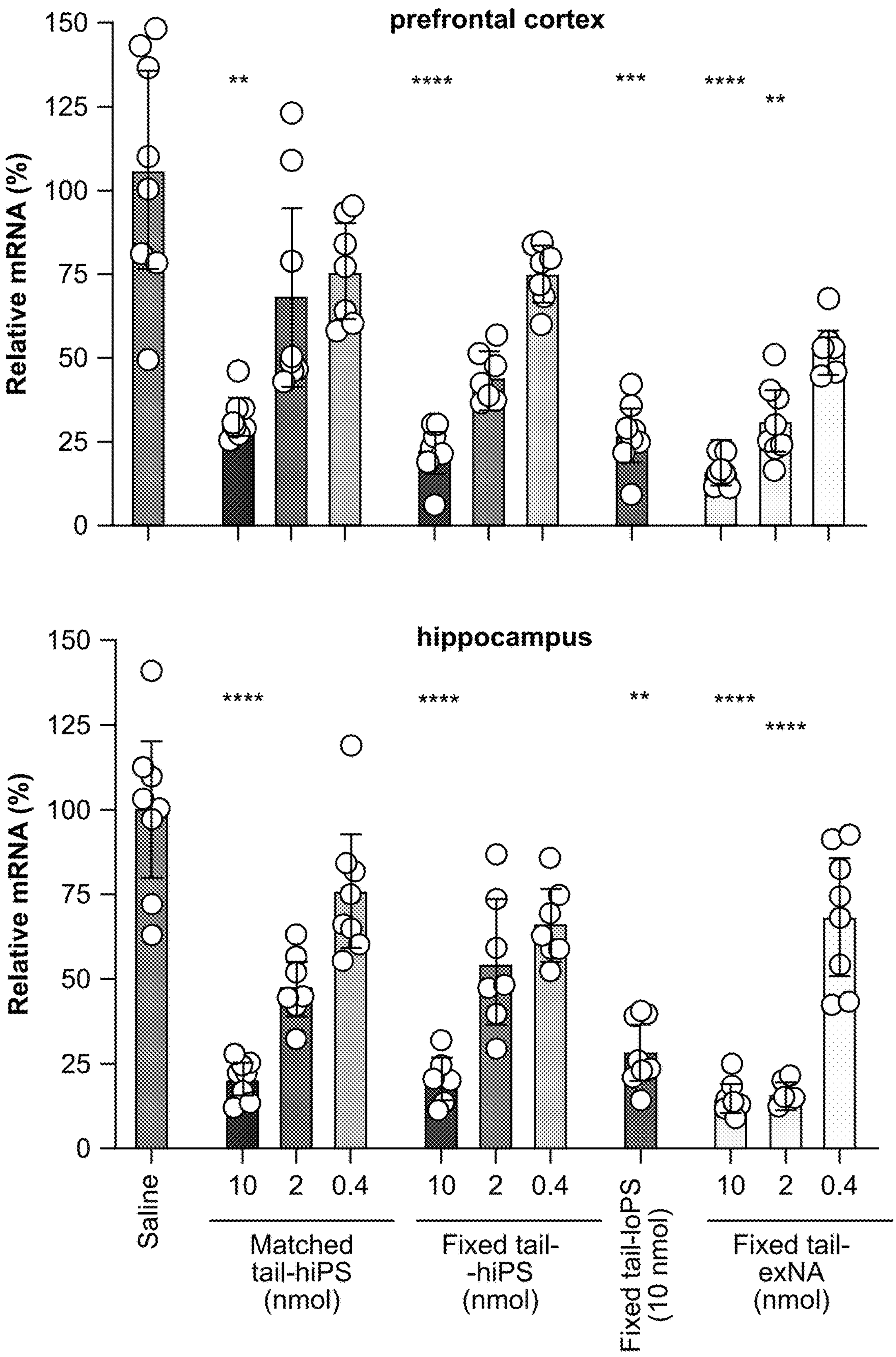
Figure 3C:
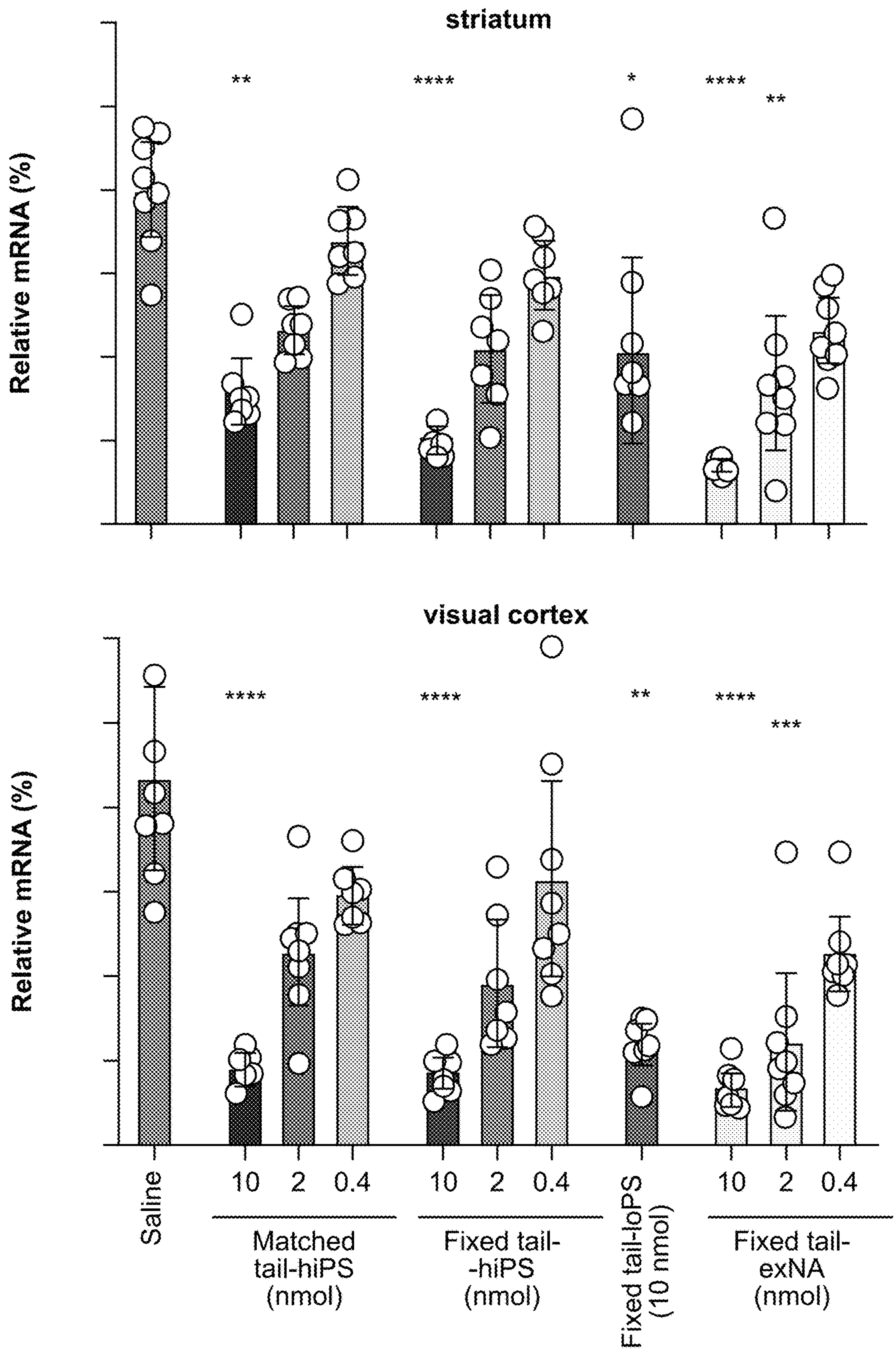
Figure 3D:
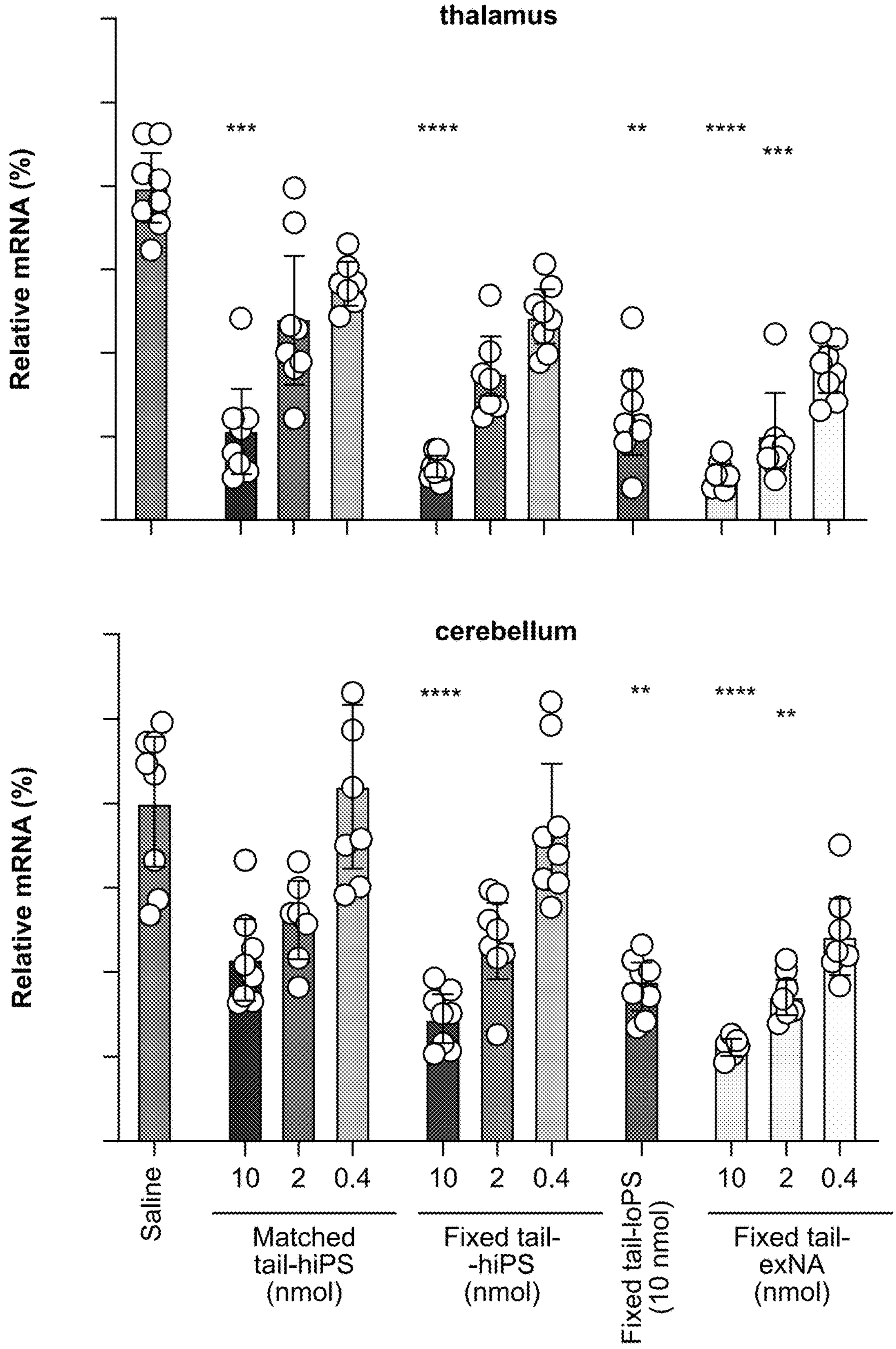

We further analyzed target engagement in 6 brain regions by qPCR (FIG. 3B-FIG. 3D). Across 6/6 regions analyzed, 10 nmol exNA scaffold provided the deepest knockdown. In a combined nested ANOVA model controlling for dose, brain region, and individual animal effects, fixed-tail hiPS compounds outperformed matched-tail hiPS by 6.8 percentage points of knockdown (P=0.0005), while exNA compounds were yet superior to fixed-tail hiPS compounds by an additional 7.7 percentage points (P=6e-15). None of the di-siRNA compounds tested resulted in a change in body weight trajectory over four weeks, and none resulted in a significant increase in neuroinflammatory markers Gfap or Iba1.

Figure 4A:
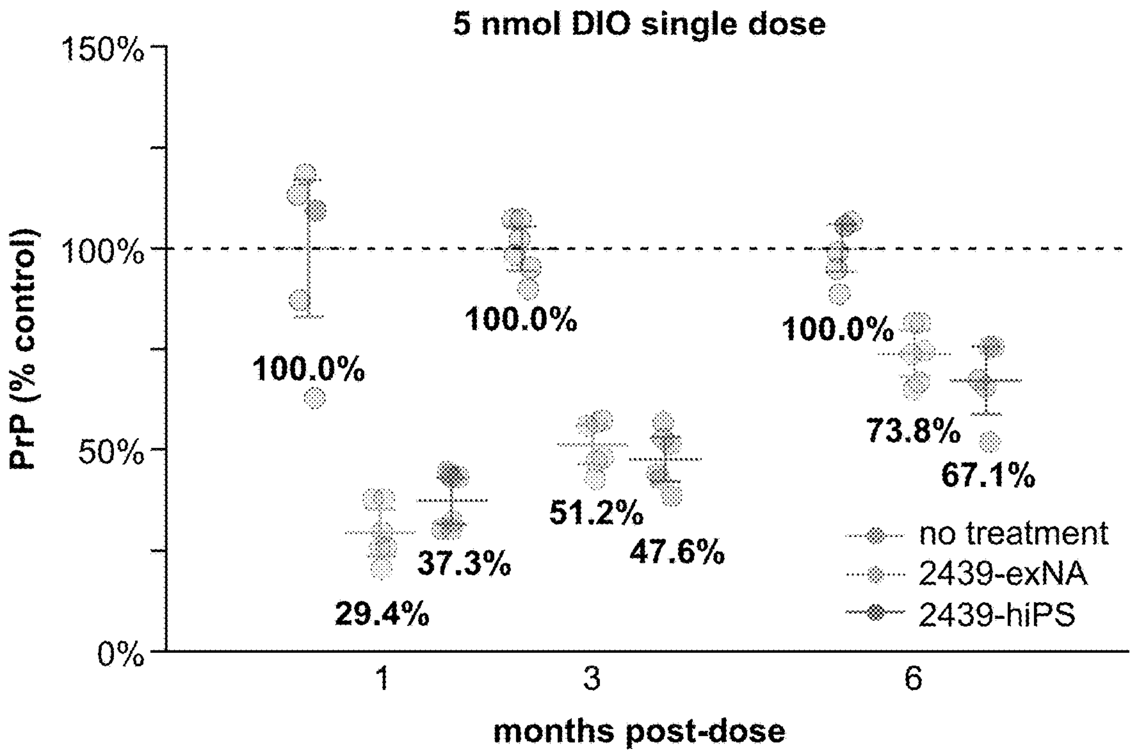
FIG. 4A-FIG. 4B depict Prp protein levels in Tg26372 humanized mice over time after being administered human di-siRNA lead sequence 2439.
Figure 4B:
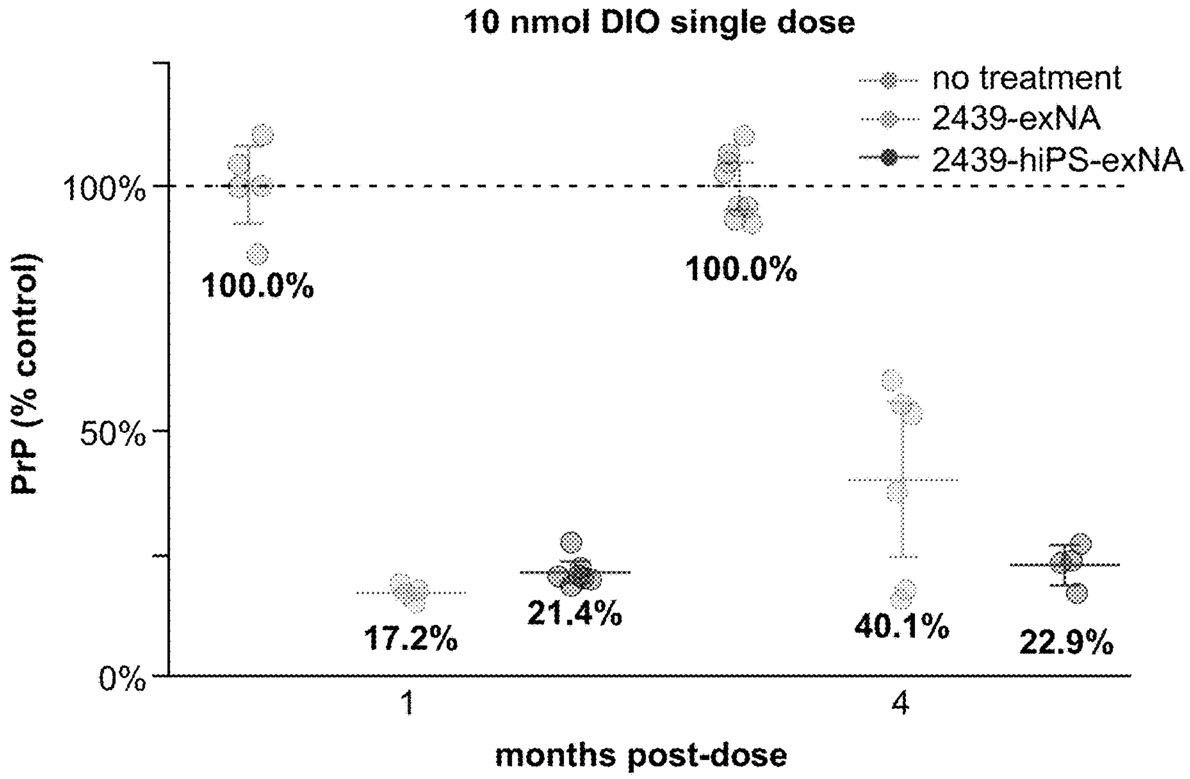

Prp protein levels were also measured in Tg26372 humanized mice administered human di-siRNA lead sequence 2439. FIG. 4A depicts Prp protein levels with 2439-exNA (also referred to as 2439-loPS-exNA and schematically depicted in FIG. 5) and 2439-hiPS-exNA, each administered at 5 nmol. FIG. 4B depicts Prp protein levels with 2439-exNA (also referred to as 2439-loPS-exNA and schematically depicted in FIG. 5) and 2439-hiPS-exNA, each administered at 10 nmol. The results demonstrate that both the low phosphonothioate content 2439 compound and the high phosphonothioate content 2439 compound effectively silenced Prp over a long duration (up to 6 months) after a single injection.

These results confirm 2439-exNA as the lead human compound. See FIG. 5 for a graphical depiction of compound 2439-exNA and the structure of the exNA internucleotide linkage.

Compound 2439-exNA is reproduced below as well.

```
an antisense strand of
                                          (SEQ ID NO: 5)
VP(mU)#(fG)#(mA)(fA)(fU)(fA)(mC)(fU)(mC)(fA)(mC)

(fA)(mA)(fA)(mG)(fU)(mG)(mC)(mA)#ex(mU)#ex(fU);
and

a sense strand of
                                          (SEQ ID NO: 4)
(mA)#(mC)#(mU)(fU)(mU)(fG)(mU)(fG)(mA)(fG)(mU)

(mA)(mU)(fU)#(mC)#(mA),
wherein "m" corresponds to a 2'-O-methyl
modification, "f" corresponds to a. 2'-fluoro
modification, "#" corresponds to a
phosphorothioate internucleotide linkage, "ex"
corresponds to a modified internucleotide
linkage of Formula I (i.e., exNA), and "VP"
corresponds to a 5' vinyl phosphonate.
```

An alternative compound, Compound 2439-hiPS-exNA, with a higher phosphorothioate content, is reproduced below as well.

```
an antisense strand of
                                          (SEQ ID NO: 8)
VP(mU)#(fG)#(mA)(fA)(fU)(fA)(mC)(fU)(mC)(fA)(mC)

(fA)(mA)(fA)(mG)#(fU)#(mG)#(mC)#(mA)#ex(mU)#ex
(fU);
and

a sense strand of
                                          (SEQ ID NO: 4)
(mA)#(mC)#(mU)(fU)(mU)(fG)(mU)(fG)(mA)(fG)(mU)

(mA)(mU)(fU)#(mC)#(mA),
wherein "m" corresponds to a 2'-O-methyl
modification, "f" corresponds to a. 2'-fluoro
modification, "#" corresponds to a
phosphorothioate internucleotide linkage, "ex"
corresponds to a modified internucleotide
linkage of Formula I (i.e., exNA), and "VP"
corresponds to a 5' vinyl phosphonate.
```

Example 4. Toxicology Studies with Divalent siRNA 2439-exNA

PrP lowering divalent siRNA 2439-exNA (hereafter referred to as 2439-exNA) is a fully chemically modified oligonucleotide drug candidate designed to degrade the mRNA encoding PrP and intended for the treatment of human prion disease.

Figure 5:
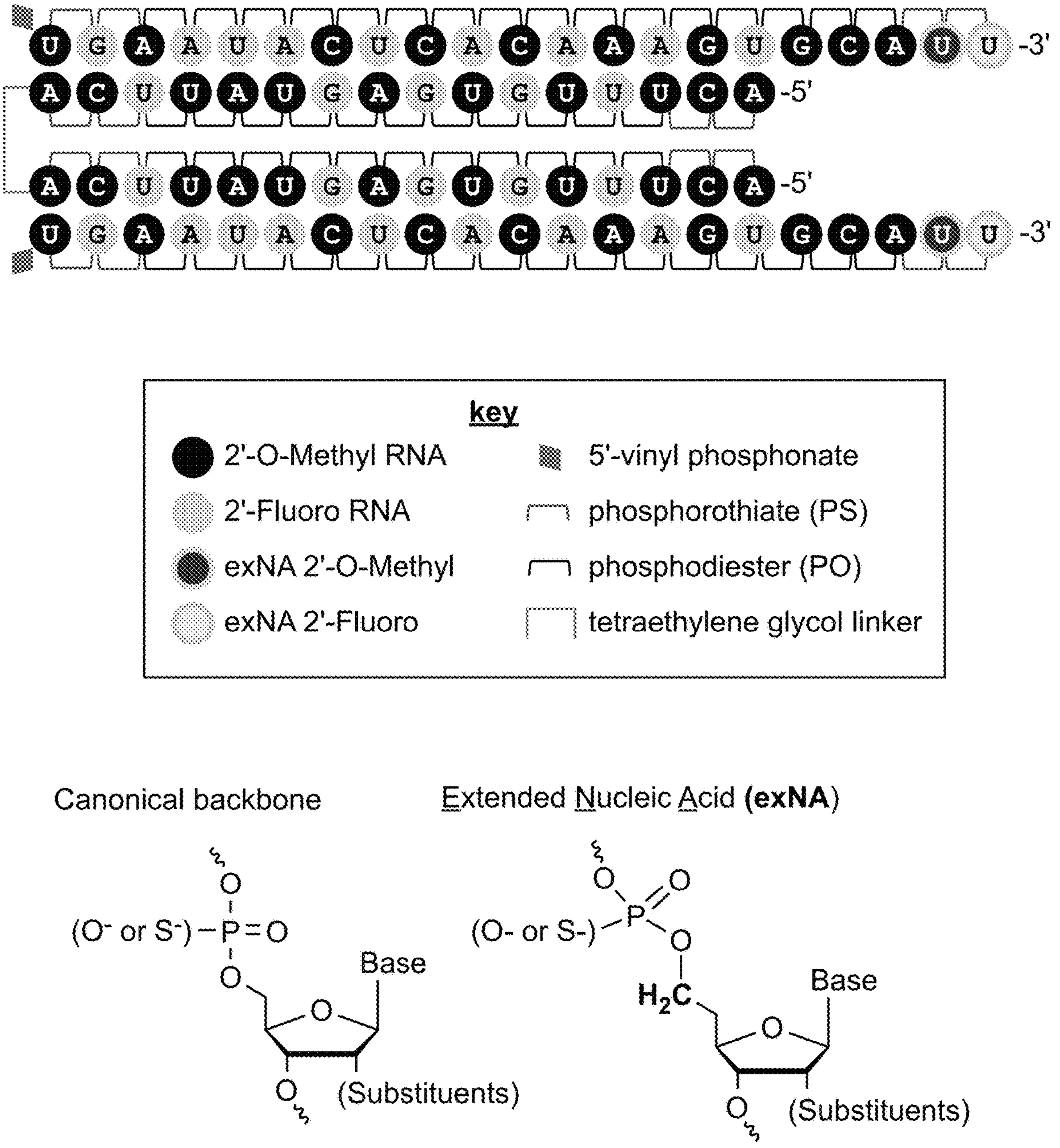
FIG. 5 (SEQ ID NO: 13) graphically depicts compound 2439-exNA.

See FIG. 5 for a graphical depiction of compound 2439-exNA. Compound 2439-exNA is reproduced below as well.

```
an antisense strand of
                                          (SEQ ID NO: 5)
VP(mU)#(fG)#(mA)(fA)(fU)(fA)(mC)(fU)(mC)(fA)(mC)

(fA)(mA)(fA)(mG)(fU)(mG)(mC)(mA)#ex(mU)#ex(fU);
and

a sense strand of
                                          (SEQ ID NO: 4)
(mA)#(mC)#(mU)(fU)(mU)(fG)(mU)(fG)(mA)(fG)(mU)

(mA)(mU)(fU)#(mC)#(mA),
wherein "m" corresponds to a 2'-O-methyl
modification, "f" corresponds to a. 2'-fluoro
modification, "#" corresponds to a
phosphorothioate internucleotide linkage, "ex"
corresponds to a modified internucleotide
linkage of Formula I (i.e., exNA), and "VP"
corresponds to a 5' vinyl phosphonate.
```

The nonclinical testing program included single administration GLP toxicity studies in rats with 28 days post-dosing recovery period and safety pharmacology endpoints, in vitro genetic toxicology studies, primary pharmacology studies and an in-silico analysis of secondary pharmacology targets.

TABLE 1

Clinical formulation of 2439-exNA drug product

| Component | Concentration (mg/mL) | Molarity (mM) |
|---|---|---|
| 2439-exNA (label) | 10 | 0.40 |
| 2439-exNA + oligonucleotide impurities* | 10.369 | 0.42 |
| Potassium dihydrogen phosphate | 0.144 | 1.06 |
| Sodium chloride | 9.058 | 155.00 |
| Sodium phosphate dibasic heptahydrate | 0.796 | 2.97 |
| Magnesium chloride hexahydrate | 2.114 | 10.40 |

*The drug substance was 96.44% pure by non-denaturing SEC, therefore 10 mg/mL label claim means 10.369 mg/mL total oligonucleotide content. Oligonucleotide impurities will also bind divalent cations, hence 10.369 mg/mL is the relevant figure for calculating the divalent cation ratio.

The clinical Drug Product formulation contains 10.40 mM of $Mg^{2+}$ and 0.42 mM of drug plus oligonucleotide impurities, for a 25:1 molar ratio of divalent cation to oligonucleotide. Accordingly, our toxicology studies also utilized a 25:1 molar ratio of divalent cation to oligonucleotide as shown in Table 2.

TABLE 2

| Formulation of 2439-exNA for rat toxicology. | | | | | | |
|---|---|---|---|---|---|---|
| Dose (mg) per animal | Dose volume (mL) | Drug + oligonucleotide impurities (mM) | Magnesium chloride (mM) | Sodium chloride (mM) | Sodium phosphate (mM) | $Mg^{2+}$:oligo ratio |
| 0 | 0.03 | 0 | 0 | 155.0 | 4.03 | — |
| 0.3 | 0.03 | 0.42 | 10.4 | 154.8 | 4.03 | 25.0 |
| 1.0 | 0.03 | 1.39 | 34.6 | 110.7 | 4.03 | 25.0 |
| 3.0 | 0.03 | 4.16 | 103.9 | 0 | 4.03 | 25.0 |

Toxicology Studies Conducted

All pivotal nonclinical safety studies were conducted in accordance with OECD (Organization for Economic Co-operation and Development) Test Guidelines and GLP. No adverse toxicity was identified in the completed 2439-exNA GLP toxicology studies in rats and 2439-exNA was not genotoxic. This package of non-clinical toxicology studies is consistent with ICH M3 guidance and the completed animal studies supports the safety of the proposed clinical investigation with 2439-exNA in patients with or genetically at high risk for prion disease.

TABLE 3

| Toxicology studies with 2439-exNA. | | | |
|---|---|---|---|
| Study type and duration | Dose/Concentration | Dosing Route | Species |
| Single dose toxicity: | | | |
| Single-dose pivotal toxicity study | 0.3, 1.0, and 3.0 mg | IT | Rat |
| Genetic toxicology: | | | |
| Bacterial reverse mutation | 0, 5.0, 16, 50, 160, 500, 1600, and 5000 µg/plate | In vitro | *Salmonella typhimurium* (TA1535, TA1537, TA98, and TA100) and *Escherichia coli* (WP2 trp uvrA) strains |
| In vitro micronucleus assays | 0, 7.5, 15, 30, 60, 122.5, 250 and 500 µg/mL | In vitro | CHO-K1 cells |

Single-Dose Toxicity

Rat

A Single Intrathecal Dose Toxicology and Toxicokinetic Study in Rats with a 28-Day Recovery Period The purpose of this study was to evaluate the potential toxicity and toxicokinetics of 2439-exNA following a single intrathecal injection to Sprague Dawley rats. The reversibility of any toxicological effects were evaluated following a 28-day recovery period.

One hundred sixty-two (81 males/81 females) Sprague Dawley rats were assigned to one of four dose groups: Group 1, Vehicle Control (0 mg), Group 2-Low (0.3 mg), Group 3-Mid (1.0 mg), and Group 4-High (3.0 mg) 2439-exNA. On Day 1, the animals were administered the appropriate test or control article via intrathecal bolus injection. On Days 2 and 29, core and recovery animals, respectively, were humanely terminated and a necropsy with select tissue collection was performed.

The formulation analysis resulted in average concentrations that were outside of the acceptance criteria with results of 116.4 to 122.7% of the nominal concentrations 2439-exNA. Based on the analysis performance, the reported results are considered representative of the concentrations of in the formulation samples, with the exceptions that the study samples are not within proven stability. No indication of sample degradation has been observed and most samples missed the acceptance criteria, showing that the nominal concentrations were exceeded in all analyte-containing formulations.

There were no clinical observations attributed to the administration of 2439-exNA. In addition, there were no changes in body weights, body weight gains, or food consumption attributed to the administration of 2439-exNA.

There were no ocular observations attributed to the intrathecal administration of 2439-exNA in Sprague Dawley rats.

TK parameters were determined and evaluated for 2439-exNA in male and female Sprague Dawley rats following intrathecal administration on Day 1. All control (Group 1) samples were BLOQ. All groups were reanalyzed without concentrations at 48 and 72 hr, except the Group 2 females which BLOQ at those time points, as these concentrations often increased from earlier time points and created apparent biphasic declines that may not be true characterizations of the elimination of 2439-exNA.

Following the dose administration, Tmax occurred at the first target sample collection time of 0.5 hour. There were no apparent sex or dose effects on the TK parameters of siRNA 2439-exNA. Systemic exposure increased in a near dose proportional manner for both males and females as the dose was increased from 0.367 to 3.49 mg.

There were no changes in hematology, coagulation, serum chemistry, and urine parameters attributed to the administration of 2439-exNA. Sporadic statistically significant changes in some parameters relative to same-day Group 1 controls were either not dose-dependent limited in scope and considered due to normal biological variation.

Sprague Dawley rats given up to 3.0 mg 2439-exNA by intrathecal bolus injection on Day 1 and terminated on Day 2 had no increased mortality, no gross findings and no microscopic findings attributed to the administration of 2439-exNA. Similarly, recovery animals terminated on Day 29 had no findings attributed to the administration of 2439-exNA.

One Group 1 core female, one Group 2 core male, and one Group 4 core female had minimal to mild necrosis of deep skeletal muscle of the skin at the injection site. Two of these lesions were perpendicular to the skin surface, suggesting traumatic needle injury from the injection.

Overall, there were no observed adverse effects related to intrathecal administration of 2439-exNA to Sprague Dawley rats across the dose range tested of 0.3 to 3.0 mg. The No Observed Adverse Effect Level (NOAEL) was determined to be 3.0 mg.

Genotoxicity 2439-exNA was evaluated for genotoxic potential in alignment with Option 1 of ICH S2 (R1) (2011). The studies conducted were the in vitro bacterial reverse mutation assay (GLP) and the vitro micronucleus test with the Chinese hamster ovary derived CHO-K1 cells (GLP). The highest concentrations of 2439-exNA used for the in vitro assays, 5000 mcg/plate, were the maximum dose level recommended per ICH S2A(R1).

In Vitro Studies

Bacterial Reverse Mutation Assay

The objective of the study was to evaluate the ability of 2439-exNA to induce reverse mutations in *Salmonella* and *E. coli* strains in the presence or absence of an exogenous mammalian metabolic activation system containing microsomal enzymes (S9). The study was conducted according to the ICH S2 (R1) and OECD-471 test guidelines.

Assay was performed using *Salmonella typhimurium* (TA1535, TA1537, TA98, and TA100) and *Escherichia coli* (WP2 trp uvrA) strains in the presence (+S9) and absence (−S9) of metabolic activation (rat liver homogenate fraction). Seven dose levels of 2439-exNA (5.0, 16, 50, 160, 500, 1600 and 5000 μg/plate) along with the concurrent positive and vehicle/negative controls were tested for the mutation assay. The revertant colony numbers obtained from the vehicle/negative and positive controls in all the five tester strains (TA1535, TA1537, TA98, TA100, and WP2 trp uvrA), met the study plan acceptance criteria. The mean revertant counts obtained from the five bacterial strains treated with SWFI (vehicle/negative control used for 2439-exNA and Vehicle 1 used for SAZ), and DMSO (Vehicle 2 for 2NF, 9AC, NQO, 2AA, and B[a]P) were within the limits of the laboratory's historical control range. The mean revertant counts expressed by the positive controls were within the established laboratory's historical control data range. The positive control items, with or without S9, produced the expected increase in revertant colony counts to at least twice the concurrent vehicle/negative control levels, confirming the sensitivity and validity of the test system. Based on these results, the assay was considered to have met the required criteria for a valid assay in all strains.

No 2439-exNA precipitates were observed, and there was no thinning of the background lawn or significant reduction in revertant colony counts (<0.5-fold) compared to vehicle/negative control observed in any doses or conditions tested. Therefore, 2439-exNA was not considered cytotoxic to the bacterial system.

2439-exNA did not induce an increase in the revertant frequencies (≥2-fold) as compared to that of the vehicle/negative controls, for all concentrations tested under both non-activated as well as S9-activated metabolic conditions.

In conclusion, under the conditions of this study, the test item 2439-exNA was devoid of any mutagenic potential in the bacterial reverse mutation test (Ames test), when tested on *S. typhimurium* strains TA1535, TA1537, TA98, TA100, and on the *E. coli* strain WP2 trp uvrA, with and without metabolic activation (±S9), at dose levels up to the Guideline limit dose of 5000 μg/plate.

Micronucleus Assay

The objective of this study was to evaluate the cytogenetic potential of the test item, 2439-exNA, using the in vitro micronucleus test with the Chinese hamster ovary derived CHO-K1 cells. The study was conducted according to the ICH S2 (R1) and OECD-487 test guidelines.

Exponentially growing CHO-K1 cells were treated in duplicate with 2439-exNA at a range of concentrations up to the highest dose of 500 μg/mL in the presence (4-hour treatment) or absence (4-hour and 26-hour treatments) of metabolic activation (rat liver S9 microsomal fraction [S9]). Concurrent vehicle/negative and positive control items were included for each treatment regimen. Cells were evaluated for cytotoxicity and micronuclei count by flow cytometry (~20,000 nuclei per dose).

The degree of cytotoxicity following treatment was evaluated by determining the Relative Population Doubling (RPD). As recommended by the ICH and OECD-487 test guidelines, the highest concentrations chosen for analysis of micronucleus aimed to achieve cytotoxicity of approximately 55±5% (i.e., reduction in RPD to 45±5% compared to concurrent vehicle/negative control). No 2439-exNA precipitate was observed (checked by visual and microscopic examination) at the beginning and end of the treatment in all 3 regimens.

2439-exNA did not show any significant decrease (i.e., <45±5%) in mean RPD at any tested concentration and conditions, indicating that 2439-exNA was non-cytotoxic to the test system in the absence or presence of S9. Therefore, the highest tested concentration of 500 μg/mL (standard limit dose) was chosen for the micronucleus evaluation. Two additional lower concentrations (250 and 125 μg/mL) were also analyzed for micronucleus evaluation in each of the 3 treatment regimens.

The results obtained with vehicle/negative control groups fell within or close to the 95% confidence limits (CI) of the distribution of the laboratory historical vehicle/negative control data range. At least one dose levels of the positive control induced a statistically significant increase in micronuclei or hypodiploid frequencies (p≤0.01). The results obtained from concurrent positive and vehicle/negative controls confirmed the sensitivity of the test system, the effectiveness of the S9 mix, and the validity of the assay.

Cultures treated with 2439-exNA did not show any statistically significant increase in the incidence of micronuclei. The numbers of micronuclei were comparable with the concurrent vehicle/negative control and were within or close to the historical control range. There was no significant increase in hypodiploid cells, indicative of numerical aberrations, in either the short-duration or extended treatments with 2439-exNA, in the absence or presence of S9.

In conclusion, 2439-exNA was considered negative for clastogenic or aneugenic activity in the in vitro micronucleus assay based on the lack of increased micronuclei or hypodiploid frequencies in CHO-K1 cells following 4-hour incubation with and without metabolic activation and 26-hour incubation without metabolic activation at dose levels up to the Guideline limit dose of 500 μg/mL.

Discussion and Conclusion

The toxicology studies conducted with 2439-exNA adequately characterized the safety of 2439-exNA.

Single dose GLP nonclinical toxicology studies were conducted in the rat. The studies used intrathecal administration, which is the intended route of administration for patients. The toxicology assessment did not identify adverse toxicity following a single IT dose of 2439-exNA of up to 3.0 mg in rat GLP toxicology studies.

2439-exNA was not genotoxic; 2439-exNA was negative in both the bacterial reverse mutation assay (i.e., non-mutagenic) and in the chromosomal aberration assay in cultured Chinese hamster lung fibroblast with or without metabolic activation (i.e., non-clastogenic).

Incorporation by Reference

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed:

1. A branched RNA compound consisting of a first dsRNA molecule and a second dsRNA molecule, wherein each dsRNA molecule comprises:

an antisense strand of (SEQ ID NO: 5)
VP(mU)#(fG)#(mA)(fA)(fU)(fA)(mC)(fU)(mC)(fA)(mC)(fA)(mA)(fA)(mG)(fU)(mG)(mC)(mA)#ex(mU)#ex(fU);
and a sense strand of (SEQ ID NO: 6)
(mA)#(mC)#(mU)(fU)(mU)(fG)(mU)(fG)(mA)(fG)(mU)(mA)(mU)(fU)#(mC)#(mA),
wherein "m" corresponds to a 2'-O-methyl modification, "f" corresponds to a 2'-fluoro modification, "#" corresponds to a phosphorothioate internucleotide linkage, "ex" corresponds to a modified internucleotide linkage of Formula VIII, (VIII)

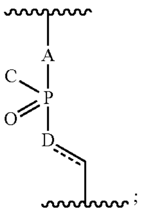

;

wherein:

D is selected from the group consisting of O, $OCH_2$, OCH, $CH_2$, and CH;

C is $S^-$;

A is selected from the group consisting of O and $CH_2$, wherein when D is O, A is $CH_2$;

$\equiv$ is an optional double bond;

and "VP" corresponds to a 5' vinyl phosphonate, and wherein the first and second dsRNA molecules are connected to one another by a linker and the linker is attached to the 3' end of each sense strand.

2. A pharmaceutical formulation comprising:

i) the branched RNA compound of claim 1 at a concentration of 1 mg/ml to 50 mg/mL;

ii) potassium phosphate at a concentration of 0.05 mg/mL to 0.5 mg/ml;

iii) sodium chloride at a concentration of 5 mg/mL to 15 mg/ml;

iv) sodium phosphate at a concentration of 0.1 mg/mL to 2.0 mg/ml; and v) magnesium chloride at a concentration of 1.0 mg/mL to 5.0 mg/mL.

3. The pharmaceutical formulation of claim 2, wherein:

i) the concentration of the branched RNA compound is 10 mg/mL;

ii) the concentration of potassium phosphate is 0.14 mg/ml;

iii) the concentration of sodium chloride is 9 mg/ml;

iv) the concentration of sodium phosphate is 0.8 mg/mL; and v) the concentration of magnesium chloride is 2.1 mg/mL.

4. The branched RNA compound of claim 1, wherein the modified internucleotide linkage of Formula VIII has the structure of Formula XIII:

(XIII)
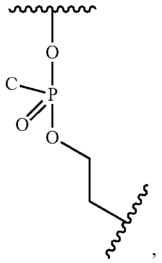
wherein C is $S^-$.
5. The branched RNA compound of claim 1, wherein the linker has the structure of L2:
(L2)
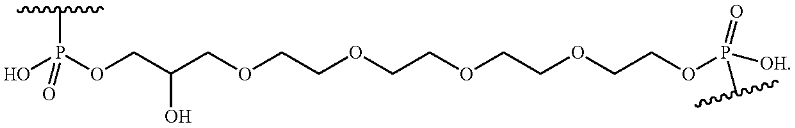
* * * * *